(12) United States Patent
Li et al.

(10) Patent No.: US 11,241,407 B2
(45) Date of Patent: Feb. 8, 2022

(54) COMPOSITIONS, METHODS, KITS AND SYSTEMS FOR CANCER TREATMENT AND METABOLIC INTERVENTION THERAPY

(71) Applicant: Filtricine, Inc., Mountain View, CA (US)

(72) Inventors: Xiyan Li, Mountain View, CA (US); Xin Wang, Palo Alto, CA (US); Xiaolu Yang, Menlo Park, CA (US)

(73) Assignee: Filtricine, Inc., Mountain View, CA (US)

( * ) Notice: Subject to any disclaimer, the term of this patent is extended or adjusted under 35 U.S.C. 154(b) by 0 days.

(21) Appl. No.: 16/897,152

(22) Filed: Jun. 9, 2020

(65) Prior Publication Data
US 2020/0297679 A1    Sep. 24, 2020

Related U.S. Application Data

(63) Continuation of application No. PCT/US2018/065045, filed on Dec. 11, 2018.

(60) Provisional application No. 62/597,392, filed on Dec. 11, 2017.

(51) Int. Cl.

| | | |
|---|---|---|
| A61K 31/198 | (2006.01) | |
| A61K 31/7004 | (2006.01) | |
| A61K 31/375 | (2006.01) | |
| A61K 33/26 | (2006.01) | |
| A61K 33/34 | (2006.01) | |
| A61K 33/24 | (2019.01) | |
| A61K 33/16 | (2006.01) | |
| A61K 33/18 | (2006.01) | |
| A61K 33/32 | (2006.01) | |
| A61K 33/04 | (2006.01) | |
| A61K 33/30 | (2006.01) | |
| A61K 31/714 | (2006.01) | |
| A61K 31/07 | (2006.01) | |
| A61K 31/675 | (2006.01) | |
| A61K 31/355 | (2006.01) | |
| A61K 31/519 | (2006.01) | |
| A61K 31/593 | (2006.01) | |
| A61K 31/51 | (2006.01) | |
| A61K 31/525 | (2006.01) | |
| A61K 31/455 | (2006.01) | |
| A61K 31/4188 | (2006.01) | |
| A61K 31/14 | (2006.01) | |

(52) U.S. Cl.
CPC .......... *A61K 31/198* (2013.01); *A61K 31/07* (2013.01); *A61K 31/14* (2013.01); *A61K 31/355* (2013.01); *A61K 31/375* (2013.01); *A61K 31/4188* (2013.01); *A61K 31/455* (2013.01); *A61K 31/51* (2013.01); *A61K 31/519* (2013.01); *A61K 31/525* (2013.01); *A61K 31/593* (2013.01); *A61K 31/675* (2013.01); *A61K 31/7004* (2013.01); *A61K 31/714* (2013.01); *A61K 33/04* (2013.01); *A61K 33/16* (2013.01); *A61K 33/18* (2013.01); *A61K 33/24* (2013.01); *A61K 33/26* (2013.01); *A61K 33/30* (2013.01); *A61K 33/32* (2013.01); *A61K 33/34* (2013.01)

(58) Field of Classification Search
None
See application file for complete search history.

(56) References Cited

U.S. PATENT DOCUMENTS

| | | | | |
|---|---|---|---|---|
| 3,024,167 | A * | 3/1962 | Damaskus | ........... A61K 38/014 530/354 |
| 3,697,287 | A | 10/1972 | Winitz et al. | |
| 4,988,724 | A | 1/1991 | Ajani et al. | |
| 5,108,767 | A | 4/1992 | Mulchandani et al. | |
| 5,597,805 | A | 1/1997 | Breborowicz | |
| 5,776,503 | A * | 7/1998 | Martis | .................... A61K 31/40 424/663 |
| 6,214,802 | B1 * | 4/2001 | Nakamura | .............. A61K 38/38 514/15.2 |
| 6,274,103 | B1 * | 8/2001 | Taylor | ................. A61M 1/1656 422/261 |
| 6,399,381 | B1 | 6/2002 | Blum et al. | |

(Continued)

FOREIGN PATENT DOCUMENTS

| | | |
|---|---|---|
| AU | 2016326347 A1 | 5/2018 |
| CA | 3033333 A1 | 3/2017 |

(Continued)

OTHER PUBLICATIONS

Baron, D.N. and McIntyre, N. Glucose is dextrose is glucose. British Medical Journal. Jul. 3, 1976, 41-42. Downloaded Jul. 14, 2020 from https://www.ncbi.nlm.nih.gov/pmc/articles/PMC1687736/pdf/brmedj00524-0047d.pdf (Year: 1976).*
Google patent search_7-14-2020_dialysis solution glucose vitamin arginine (Year: 2020).*
Google scholar search_7-14-2020_dialysis solution glucose vitamin arginine (Year: 2020).*
English machine translation of WO-2013011166-A2. (Year: 2020).*
Prior_Art_Web_Search_Printable_History_Generator_7-15-20.pdf (Year: 2020).*

(Continued)

*Primary Examiner* — Michael P Cohen
(74) *Attorney, Agent, or Firm* — Wilson Sonsini Goodrich & Rosati

(57) ABSTRACT

The present disclosure provides compositions and methods for treating cancer with nutritionally modified diets and/or dialysis treatment, such as through amino acid depletion of one or more nonessential amino acids. In some aspects, the present disclosure provides compositions and methods for treating obesity with such modified diets and/or dialysis treatment. Furthermore, in some aspects, the present disclosure provides compositions and methods for treating renal disease with such modified diets and/or dialysis treatment.

26 Claims, 17 Drawing Sheets

(56) References Cited

U.S. PATENT DOCUMENTS

| | | | |
|---|---|---|---|
| 8,927,505 B2* | 1/2015 | Moore | A61K 31/20 514/23 |
| 8,952,040 B2 | 2/2015 | Yue et al. | |
| 9,872,844 B2 | 1/2018 | Zemel et al. | |
| 10,973,251 B1 | 4/2021 | Li et al. | |
| 2003/0013765 A1 | 1/2003 | Veech | |
| 2008/0221497 A1 | 9/2008 | Haik, Jr. | |
| 2008/0255499 A1* | 10/2008 | Kim | A61P 43/00 604/28 |
| 2010/0187476 A1* | 7/2010 | Yugari | A61K 45/06 252/184 |
| 2010/0317602 A1 | 12/2010 | Moore | |
| 2011/0229521 A1 | 9/2011 | Schiffrin et al. | |
| 2014/0235569 A1 | 8/2014 | Halevie-Goldman | |
| 2016/0278415 A1 | 9/2016 | Marsland | |

FOREIGN PATENT DOCUMENTS

| | | | |
|---|---|---|---|
| CN | 102164595 A | 8/2011 | |
| CN | 102215837 A | 10/2011 | |
| CN | 103652926 A | 3/2014 | |
| CN | 108777999 A | 11/2018 | |
| EP | 0259167 A2 | 3/1988 | |
| EP | 2374452 A1 | 10/2011 | |
| EP | 3352586 A1 | 8/2018 | |
| GB | 1263336 A | 2/1972 | |
| JP | 2018532398 A | 11/2018 | |
| SG | 190649 A1 | 6/2013 | |
| WO | WO-2013011166 A2 * | 1/2013 | A61K 33/06 |
| WO | WO-2014197533 A2 | 12/2014 | |
| WO | WO-2015031735 A1 | 3/2015 | |
| WO | WO-2017053328 A1 | 3/2017 | |
| WO | WO-2017144877 A1 | 8/2017 | |
| WO | WO-2019118519 A1 | 6/2019 | |
| WO | WO-2021016132 A1 | 1/2021 | |

OTHER PUBLICATIONS

Google search_why omit cysteine from peritoneal dialysis patient_ 11-20-2020 (Year: 2020).*

H.L. Tjiong, et al. Dialysate as food as an option for automated peritoneal dialysis. NDT Plus (2008) I [Suppl 4]: iv36-iv40. (Year: 2008).*

Anderson, et al. Design and Evaluation by Nitrogen Balance and Blood Aminograms of an Amino Acid Mixture for Total Parenteral Nutrition of Adults with Gastrointestinal Disease. J Clin Invest. Mar. 1974; 53(3): 904-912. doi: 10.1172/JCI107631.

ATCC Product Catalog MDA-MB-453 (ATCC® HTB-131™) Retrieved Online at URL: https://www.atcc.org/products/all/HTB-131.aspx#characteristics.

Baxter Corporation. Product Monograph Nutrineal™ PD4 (1.1% Amino Acid Peritoneal Dialysis Solution). Date of Revision: Jul. 30, 2012. 31 pages.

Cairns, et al. Regulation of cancer cell metabolism. Nat Rev Cancer. Feb. 2011. 11 (2):85-95. doi: 10.1038/nrc2981.

Co-pending U.S. Appl. No. 15/762,032, inventors Li; Xiyan et al., filed on Mar. 21, 2018.

Courtney-Martin, et al. Methionine-adequate cysteine-free diet does not limit erythrocyte glutathione synthesis in young healthy adult men. J Nutr. Nov. 2008;138(11):2172-8. doi: 10.3945/jn.108.093302.

Courtney-Martin, et al. Sulfur amino acid metabolism and requirements. Nutr Rev. Mar. 2012. 70(3):170-175. doi: 10.1111/j.1753-4887.2011.00466.x.

Drexler, et al. Malignant hematopoietic cell lines: in vitro models for the study of MLL gene alterations. Leukemia. Feb. 2004. 18(2):227-232. DOI: 10.1038/sj.leu.2403236.

Durando, et al. Dietary methionine restriction with FOLFOX regimen as first line therapy of metastatic colorectal cancer: a feasibility study. Oncology. 2010. 78(3-4):205-209. doi: 10.1159/000313700. Epub Apr. 26, 2010. Abstract Only.

European search report and opinion dated Apr. 12, 2019 for EP Application No. 16849444.1.

Gazdar, et al. Lung cancer cell lines as tools for biomedical discovery and research. J Natl Cancer Inst. Sep. 8, 2010. 102(17): 1310-1321. doi: 10.1093/jnci/djq279. Epub Aug. 2, 2010.

Goseki, et al. Inhibitory effect of L-methionine-deprived amino acid imbalance using total parenteral nutrition on growth of ascites hepatoma in rats. Tohoku J Exp Med. Feb. 1987. 151 (2):191-200. DOI: 10.1620/tjem.151.191.

Hall, et al. MDA-MB-453, an androgen-responsive human breast carcinoma cell line with high level androgen receptor expression. Eur J Cancer. 1994;30A(4):484-90.

Hanahan, et al. Hallmarks of cancer: the next generation. Cell. Mar. 4, 2011. 144(5):646-74. doi: 10.1016/j.cell.2011.02.013.

International Preliminary Report on Patentability dated Apr. 5, 2018 for PCT/US2016/052720.

International search report with written opinion dated Apr. 30, 2019 for PCT/US2018/065045.

International search report with written opinion dated Oct. 15, 2020 for PCT/US2020/042677.

International search report with written opinion dated Dec. 9, 2016 for PCT/US2016/052720.

Lauterberg, et al. Depletion of total cysteine, glutathione, and homocysteine in plasma by ifosfamide/mesna therapy. Cancer Chemother Pharmacol. 1994;35(2):132-136.

Linnoila. Spectrum of neuroendocrine differentiation in lung cancer cell lines featured by cytomorphology, markers, and their corresponding tumors. J Cell Biochem. 63: 92-106. doi:10.1002/jcb.240630506.

Maddocks, et al. Serine starvation induces stress and p53-dependent metabolic remodelling in cancer cells. Nature. Jan. 24, 2013;493(7433):542-6. doi: 10.1038/nature11743. Epub Dec. 16, 2012.

Miller, et al. Oxidation of the glutathione/glutathione disulfide redox state is induced by cysteine deficiency in human colon carcinoma HT29 cells. J Nutr. Aug. 2002;132(8):2303-6.

Miller, et al. Reduction of human blood asparagine by hemodialysis. Cancer. May 1972;29(5):1347-51. doi: 10.1002/1097-0142(197205)29:5 1347::aid-cncr28202905333.0.co;2-j.

Mitra, et al. Technologies for deriving primary tumor cells for use in personalized cancer therapy. Trends Biotechnol. Jun. 2013. 31(6):347-354. doi: 10.1016/j.tibtech.2013.03.006. Epub Apr. 16, 2013.

Moore, et al. An androgen receptor mutation in the MDA-MB-453 cell line model of molecular apocrine breast cancer compromises receptor activity. Endocr Relat Cancer. Jul. 22, 2012;19(4):599-613. doi: 10.1530/ERC-12-0065. Print Aug. 2012.

Mouradov, et al. Colorectal cancer cell lines are representative models of the main molecular subtypes of primary cancer. Cancer Res. Jun. 15, 2014. 74(12):3238-3247. doi: 10.1158/0008-5472.CAN-14-0013. Epub Apr. 22, 2014.

Murtas, et al. Differences in Amino Acid Loss Between High-Efficiency Hemodialysis and Postdilution and Predilution Hemodiafiltration Using High Convection Volume Exchange—A New Metabolic Scenario? A Pilot Study. J Ren Nutr. Mar. 2019;29(2):126-135. doi: 10.1053/j.jrn.2018.07.005. Epub Oct. 16, 2018.

Neve, et al. A collection of breast cancer cell lines for the study of functionally distinct cancer subtypes. Cancer Cell. Dec. 2006. 10(6):515-527. DOI: 10.1016/j.ccr.2006.10.008.

Office action dated Apr. 27, 2020 for U.S. Appl. No. 15/762,032.

Oh, et al. Micronutrient and Amino Acid Losses During Renal Replacement Therapy for Acute Kidney Injury. Kidney Int Rep. Aug. 2019; 4(8): 1094-1108. Published online May 23, 2019. doi: 10.1016/j.ekir.2019.05.001.

Ooi, et al. Adequate nourishment through total parenteral nutrition treatment may augment immune function in patients with colon cancer. Arch Med Res. Jul.-Aug. 2004 35(4):289-293. DOI: 10.1016/j.arcmed.2004.03.004.

Pittard J. Chapter 13—Safety Monitors in Hemodialysis. Handbook of Dialysis Therapy (Fifth Edition) 2017. pp. 162-190.e2. https://doi.org/10.1016/B978-0-323-39154-2.00013-8.

(56) References Cited

OTHER PUBLICATIONS

Saiselet, et al. Thyroid cancer cell lines: an overview. Front Endocrinol (Lausanne). Nov. 16, 2012. 3:133. doi: 10.3389/fendo.2012.00133. eCollection 2012.

Samel, et al. Peritoneal cancer treatment with CYP2B1 transfected, microencapsulated cells and ifosfamide. Cancer Gene Ther. Jan. 1, 2006. 13(1):65-73. DOI: 10.1038/sj.cgt.7700849.

Scott, et al. Single amino acid (arginine) deprivation: rapid and selective death of cultured transformed and malignant cells. Br J Cancer. Sep. 2000;83(6):800-810.

Sheen, et al. Defective regulation of autophagy upon leucine deprivation reveals a targetable liability of human melanoma cells in vitro and in vivo. Cancer Cell. May 17, 2011. 19(5):613-628. doi: 10.1016/j.ccr.2011.03.012.

Sigma-Aldrich. L-Methionine. www.sigmaaldrich.com [online], [retrieved Sep. 21, 2020], Retrieved from the Internet, https://www.sigmaaldrich.com/content/dam/sigma-aldrich/docs/Sigma/Product_Information_Sheet/1/m9625pis.pdf.

Sobel, et al. Cell lines used in prostate cancer research: a compendium of old and new lines—part 1. J Urol. Feb. 2005. 173(2):342-359. DOI: 10.1097/01.ju.0000141580.30910.57.

Street, et al. Some Effects Produced by Long-Continued Subminimal Intakes of Vitamin B(1). Yale J Biol Med. Jan. 1941; 13(3): 293-308.1.

Tang, et al. Cystine Deprivation Triggers Programmed Necrosis in VHL-Deficient Renal Cell Carcinomas. Cancer Res. Apr. 1, 2016;76(7):1892-903. doi: 10.1158/0008-5472.CAN-15-2328. Epub Feb. 1, 2016.

Tjiong, et al. Dialysate as food as an option for automated peritoneal dialysis. NDT Plus. Oct. 2008;1(Suppl 4):iv36-iv40. doi: 10.1093/ndtplus/sfn122.

Vander Heiden Mg. Targeting cancer metabolism: a therapeutic window opens. Nat Rev Drug Discov. Aug. 31, 2011. 10(9):671-684. doi: 10.1038/nrd3504.

Young Vr. Adult amino acid requirements: the case for a major revision in current recommendations. J Nutr. Aug. 1994. 124(8 Suppl):1517S-1523S. doi: 10.1093/jn/124.suppl_8.1517S.

Zheng, et al. Establishment and characterization of primary lung cancer cell lines from Chinese population. Acta Pharmacol Sin. Mar. 2011. 32(3):385-392. doi: 10.1038/aps.2010.214.

European search report and opinion dated Aug. 11, 2021 for EP Application No. 18887730.2.

Co-pending U.S. Appl. No. 17/178,979, inventors LI; Xiyan et al., filed Feb. 18, 2021.

Hou, et al. Dietary essentiality of "nutritionally non-essential amino acids" for animals and humans. Exp Biol Med (Maywood). Aug. 2015; 240(8): 997-1007. Published online Jun. 2, 2015. doi: 10.1177/1535370215587913.

Hou, et al. Nutritionally Nonessential Amino Acids: A Misnomer in Nutritional Sciences. Adv Nutr. Jan. 17, 2017;8(1):137-139. doi: 10.3945/an.116.012971. Print Jan. 2017.

Maddocks, et al. Modulating the therapeutic response of tumours to dietary serine and glycine starvation. Nature. Apr. 19, 2017;544(7650):372-376. doi: 10.1038/nature22056.

Meléndez-Hevia, et al. A weak link in metabolism: the metabolic capacity for glycine biosynthesis does not satisfy the need for collagen synthesis. J Biosci. Dec. 2009;34(6):853-872. doi: 10.1007/S12038-009-0100-9.

Notice of Allowance dated Nov. 18, 2020 for U.S. Appl. No. 15/762,032.

* cited by examiner

| Diet Only Xenograft (blind to CROs) | | | |
|---|---|---|---|
| Cancer Model | Design | Arms | CRO |
| Colon | HCT116 in athymic nude mice | 4 | Aragen |
| Breast | MDA-MB-231 in NOD-SCID | 2 | Aragen |
| Breast | MDA-MB-231 in athymic nude mice | 4 | WBI |
| Prostate | PC-3 in athymic nude mice | 2 | WBI |
| Pancreatic | MIAPaCa-2 in athymic nude mice | 2 | Noble Biosci |

FIG. 2

| Overview of Rodent Diets | | | | | | |
|---|---|---|---|---|---|---|
| | Designed control | Designed control 2 | Natural food | MEAD201 | MEAD202 | MEAD203 |
| Complete | ✔ | ✔ | ✔ | | | |
| MEAD | | | | ✔ (-5) | ✔ (-3.5) | ✔ (-9) |
| Protein % (w) | 17 AA | 17 AA + Protein Y | 21 or 16 Protein Y/Z | 17 AA | 17 AA + protein X | 17 AA |
| Carbohydrates % (w) | 70.3 | 70.3 | 72.8 | 70.3 | 70.3 | 70.3 |
| Fat % (w) | 4 | 4 | 6.8 or 4 | 4 | 4 | 4 |
| Gross Energy (kcal/kg) | 3.8 | 3.9 | 4.1 | 3.8 | 3.8 | 3.9 |
| Vitamins | ✔ | ✔ | ✔ | ✔ | ✔ | ✔ |
| Minerals | ✔ | ✔ | ✔ | ✔ | ✔ | ✔ |
| Fiber % (w) | 5.0 | 5.0 | 4.6 | 5.0 | 5.0 | 5.0 |
| Food restriction | ✖ | ✖ | ✖ | ✖ | ✖ | ✖ |

FIG. 3

Dialysis Fluid

|  | MEAD101 | MEAD102 | MEAD103 | MEAD104 |
|---|---|---|---|---|
| Dextrose Na, Mg, Ca, Cl, Lactate (Baxter) | ✓ | ✓ | ✓ | ✓ |
| Essential Amino Acids | ✗ | ✓ | ✓ | ✓ |
| Arg/Glu | ✗ | ✓ | ✓ | ✓ |
| Vitamins | ✗ | 8 | 10 | 10 (B2 at 50x) |
| Mineral nutrients | ✗ | ✗ | ✗ | ✗ |

FIG. 8

Body Weight Loss Stabilized

Blood Sugar Not Increased

Ketosis Not Triggered

COMPOSITIONS, METHODS, KITS AND SYSTEMS FOR CANCER TREATMENT AND METABOLIC INTERVENTION THERAPY

CROSS-REFERENCE

This application is a continuation application of International Application No. PCT/US2018/065045, filed Dec. 11, 2018, which claims the benefit of U.S. Provisional Application No. 62/597,392, filed on Dec. 11, 2017, each of which is entirely incorporated herein by reference for all purposes.

BACKGROUND

Cancer and obesity are major public health problems. Cancer is the second leading cause of death globally, and was responsible for 8.8 million deaths in 2012. Globally, approximately 1 in 6 deaths is due to cancer. Cancer arises from the transformation of normal cells into tumor cells in a multistage process that generally progresses from a pre-cancerous lesion to a malignant tumor. One defining feature of cancer is the rapid creation of abnormal cells that grow beyond their usual boundaries, and which can then invade adjoining parts of the body and spread to other organs.

Cancer cells adopt a distinctive type of metabolism, the "Warburg effect," to promote growth, survival, proliferation, and long-term maintenance. This altered metabolism involves uncoupled cellular glycolysis and mitochondrial aerobic respiration, which may lead to the requirement of certain nutrients that are not necessary for normal cells.

The currently available treatments suffer from a number of profound drawbacks. For instance, the current cancer treatments available to patients are expensive. The economic impact of cancer is significant and continues to increase. In 2010, the total annual economic cost of cancer was estimated at approximately 1.16 trillion US dollars. Also, the traditional methods of treating cancer, such as chemotherapy and radiation therapy, tend to be highly toxic and/or non-specific to cancer, which results in limited efficacy and harmful side effects.

Obesity is a medical condition in which excess body fat has accumulated to the extent that it may have a negative impact on health. This condition is commonly caused by a combination of excessive food intake, lack of physical activity, and genetic susceptibility. Obesity increases the likelihood of various diseases and conditions, such as, cardiovascular diseases, type 2 diabetes, obstructive sleep apnea, cancer, osteoarthritis and depression.

Many of the current treatments for obesity, such as calorie restrictive dietary modification, behavior modification, exercise, medication and surgery face a number of drawbacks. Many obesity treatments are ineffective and provide only short-term results, particularly those who are morbidly obese.

Accordingly, there remains a considerable need for new cancer treatments and treatments for obesity.

SUMMARY

Cancer and metabolic diseases, such as obesity, remain as major health issues in which new, alternative, and effective treatment are currently needed. The present disclosure addresses such needs and provides a number of advantages. The present disclosure relates to providing a subject with a treatment that includes the control of a subject's nutritional diet and/or dialysis. For example, treating a patient in need thereof may comprise placing the patient on a cysteine depleted diet and placing the patient under dialysis. The present disclosure provides solid and liquid compositions that are depleted with one or more nutrients, such as nonessential amino acids, and methods of treating cancer, renal disease, and metabolic diseases, such as obesity, with the compositions. The present disclosure provides for facilities, systems and kits that relate to the distribution and/or performance of the described compositions and methods.

The present disclosure utilizes hemodialysis and peritoneal dialysis as a way to deplete one or more nutrients in the subject by administering compositions that are lacking in such nutrients. Hemodialysis involves withdrawing blood from the body and cleaning it in an extracorporeal blood circuit and then returning the cleansed blood to the body. The extracorporeal blood circuit includes a dialyzer which comprises a semipermeable membrane. Within this dialyzer waste substances and excess fluid is removed through the semipermeable membrane, and the semipermeable membrane within the dialyzer has a blood side and a dialysate side. Peritoneal dialysis involves the use of the peritoneum in a person's abdomen as the membrane through which fluid and dissolved substances are exchanged with the blood. Peritoneal dialysis is used to remove excess fluid, correct electrolyte problems, and remove toxins in those with kidney failure. In peritoneal dialysis, a solution is introduced through a permanent tube in the lower abdomen and then removed. This may either occur at regular intervals throughout the day, known as continuous ambulatory dialysis, or at night with the assistance of a machine, known as automated peritoneal dialysis. Furthermore, the present disclosure envisions utilizing hemodialysis and peritoneal dialysis as way to provide a subject in need thereof with a particular nutritional makeup by depleting and/or restoring one or more nutrients in the subject. The present disclosure provides dialysis systems and equipment thereof.

In some aspects, the present disclosure provides, a liquid composition comprising: (a) carbohydrate; (b) at least one vitamin; (c) at least one ion selected from a group consisting of sodium, calcium, magnesium, chloride, and lactate; (d) at least one essential amino acid; and (e) an aqueous solution, wherein the liquid composition optionally comprises glutamate, wherein the liquid composition comprises 0-5 µM of cysteine and/or cystine, wherein said liquid composition has a pH of 4.0-6.5, and wherein said liquid composition has an osmolarity of 300-720 mOsmol/L.

In some aspects, the present disclosure provides a liquid composition comprising: (a) carbohydrate; (b) at least one vitamin; (c) at least one ion selected from a group consisting of sodium, calcium, magnesium, chloride, and lactate; (d) at least one essential amino acid; and (e) an aqueous solution, wherein the liquid composition optionally comprises glutamate, wherein the liquid composition is substantially free of nonessential amino acids selected from alanine, asparagine, aspartate, cysteine, glycine, proline, glutamine, serine, and tyrosine, wherein the liquid composition comprises 0-5 µM of cysteine and/or cystine, wherein said liquid composition has a pH of 4.0-6.5, and wherein said liquid composition has an osmolarity of 300-720 mOsmol/L.

In some aspects, the present disclosure provides a liquid composition comprising: (a) dextrose; (b) at least one ion selected from a group consisting of sodium, calcium, magnesium, chloride, and lactate; (c) at least one essential amino acid; and (d) an aqueous solution, wherein the liquid composition comprises at least 10 µM of essential amino acid, wherein the liquid composition comprises 0-5 µM of cysteine and/or cystine, wherein the liquid composition has a pH of 4.0-6.5, and wherein the liquid composition has an osmolarity of 300-720 mOsmol/L.

In some embodiments, the carbohydrate is selected from a group consisting of dextrose and glucose. The carbohydrate may be dextrose. In certain embodiments, the amount of dextrose is 1.0-4.5% w/v. The amount of dextrose may be 1.5-4.25% w/v. The amount of dextrose may be 1.7-4.0% w/v. In another embodiment, the amount of dextrose is 0.05-0.50% w/v. The amount of dextrose may be 0.05-0.25% w/v. The amount of dextrose may be 0.08-0.22% w/v. The amount of dextrose may be 0.1-0.2% w/v.

For the liquid composition, in certain embodiments, the liquid composition comprises at least 10 µM of said essential amino acid. In some embodiments, the amount of at least one of the essential amino acid is 10-300 µM. For example, the amount of at least one of the essential amino acid is 20-250 µM. The essential amino acid may be selected from a group consisting of histidine, isoleucine, leucine, lysine, methionine, phenylalanine, threonine, tryptophan, valine, and arginine. In some embodiments, at least one of the essential amino acid is methionine. In some embodiments, at least one of the essential amino acid is arginine. The liquid composition may comprise at least two essential amino acids. The liquid composition may comprise at least three essential amino acids. The liquid composition may comprise at least four essential amino acids. The liquid composition may comprise at least five essential amino acids. The liquid composition may comprise at least six essential amino acids. The liquid composition may comprise at least seven essential amino acids. The liquid composition may comprise at least eight essential amino acids. The liquid composition may comprise at least nine essential amino acids. The liquid composition may comprise at least ten essential amino acids.

The liquid composition may further comprise at least one vitamin. The vitamin may be selected from a group consisting of vitamin A, vitamin B, vitamin C, vitamin D, vitamin E, vitamin K, and choline, such as for example, the vitamin is vitamin C. In some embodiments, the amount of the vitamin is about 0.000010 to 200 µM. In some embodiments, the liquid composition comprises at least 1 µM of vitamin C. For example, the liquid composition may comprise at least 7 µM of vitamin C. In some embodiments, the vitamin is vitamin B. The liquid composition may comprise 0.000003 to 1500 µM of said vitamin B.

The liquid composition may further comprise an essential fatty acid. The essential amino acid may be an omega-3 fatty acid.

In some embodiments, the amount of glutamate is approximately 2-500 µM. the amount of glutamate may increase glutamate in the blood by at least 150 µM.

In certain embodiments, the liquid composition further comprises at least one mineral. The mineral may be selected from a group consisting of iron, copper, chromium, fluoride, iodine, manganese, molybdenum, selenium, and zinc. The liquid composition may comprise at least 5 nM of the mineral. In some embodiments, the amount of at least one mineral is 5 nM-5 µM.

In certain embodiments, the liquid composition is stored in a container. The container may be a dialysis bag. The dialysis bag may be intended for single-use. In some embodiments, the container holds 1500 to 5000 mL of the liquid composition. For example, approximately 2000 mL of the liquid composition is a single unit. In another embodiment, approximately 2500 mL of the liquid composition is a single unit.

For the liquid composition, in certain embodiments, the amount of at least one ion is at least approximately 0.1 mEq/L. The amount of at least one ion may be 0.1-150 mEq/L.

In some embodiments, liquid composition is free of nonessential amino acids other than glutamate. Alternatively, the liquid composition may further comprise at least one nonessential amino acid. In some embodiments, the amount of the nonessential amino acid is at least approximately 5 µM. The amount of the nonessential amino acid may be 5-600 µM. The nonessential amino acid may be selected from a group consisting of alanine, asparagine, aspartate, glutamic acid, glycine, proline, glutamine, serine, and tyrosine.

In certain embodiments, the liquid composition comprises 0-4 µM of cysteine and/or cystine. For example, the liquid composition may comprise 0-1 µM of cysteine and/or cystine.

In certain embodiments, the liquid composition has a pH of approximately 5.0-6.5. The liquid composition may have a pH of approximately 5.5-6.0. The liquid composition may have a pH of approximately 6.0. The liquid composition may have a pH of approximately 5.5. The liquid composition may have a pH of approximately 5.0.

In certain embodiments, the liquid composition has an osmolarity of 300-500. For example, the liquid composition may have an osmolarity of 300-400. The liquid composition may have an osmolarity of 400-500. The liquid composition may have an osmolarity of 300-350.

For the liquid composition, in certain embodiments, the aqueous solution is sterile. In another embodiment, the aqueous solution is nonsterile. In some embodiments, the liquid composition is a dialysis solution.

In some aspects, the present disclosure provides, a dry composition comprising: (a) carbohydrate; (b) at least one vitamin; (c) at least one ion selected from a group consisting of sodium, calcium, magnesium, chloride, and lactate; (d) at least one essential amino acid; and (e) an aqueous solution, wherein the dry composition optionally comprises glutamate, wherein the dry composition comprises 0-5 µM of cysteine and/or cystine.

In some aspects, the present disclosure provides a dry composition comprising: (a) carbohydrate; (b) at least one vitamin; (c) at least one ion selected from a group consisting of sodium, calcium, magnesium, chloride, and lactate; (d) at least one essential amino acid; and (e) an aqueous solution, wherein the dry composition optionally comprises glutamate, wherein the dry composition is substantially free of nonessential amino acids selected from alanine, asparagine, aspartate, cysteine, glycine, proline, glutamine, serine, and tyrosine, and wherein the dry composition comprises 0-5 µM of cysteine and/or cystine.

In some embodiments, the carbohydrate is selected from a group consisting of dextrose, glucose, sucrose, fructose, and lactose. The carbohydrate may be dextrose.

In some aspects, the present disclosure provides a dry composition comprising: (a) dextrose; (b) at least one ion selected from a group consisting of sodium, calcium, magnesium, chloride, and lactate; and (c) at least one essential amino acid, wherein the dry composition comprises at least 2 µg of essential amino acid, and wherein the dry composition comprises 0-10 mg of cysteine and/or cystine.

For the dry composition, in certain embodiments, the amount of dextrose is at least approximately 10 g. The amount of dextrose may be 10-50 g, such as approximately 50 g. In another embodiment, the amount of dextrose is at least approximately 0.5 g. The amount of dextrose may be 0.5-2.5 g, such as approximately 2 g.

For the dry composition, in certain embodiments, the essential amino acid is selected from a group consisting of histidine, isoleucine, leucine, lysine, methionine, phenylalanine, threonine, tryptophan, valine, and arginine. In some embodiments, at least one essential amino acid is methionine. In some embodiments, at least one essential amino acid is arginine. In some embodiments, the dry composition comprises at least two essential amino acids. The dry composition may comprise at least four essential amino acids. The dry composition may comprise at least five essential amino acids. The dry composition may comprise at least six essential amino acids. The dry composition may comprise at least seven essential amino acids. The dry composition may comprise at least eight essential amino acids. The dry composition may comprise at least nine essential amino acids. The dry composition may comprise at least ten essential amino acids. In some embodiments, the dry composition comprises at least 2 µg of the essential amino acid.

The dry composition may comprise at least one vitamin. The vitamin may be selected from a group consisting of vitamin A, vitamin B, vitamin C, vitamin D, vitamin E, vitamin K, and choline. In some embodiments, the amount of the vitamin is about 0.01-1500 µg. For example, the vitamin is vitamin C. The dry composition may comprise at least 1000 µg of vitamin C. In some embodiments, the dry composition comprises at least 2500 µg of vitamin C. In some embodiments, the dry composition comprises at least 0.01 µg of said vitamin B. The dry composition may comprise at least 1 µg of vitamin B.

In some embodiments, the amount of said glutamate is approximately 0.1 mg to 50 mg. The liquid composition may be free of nonessential amino acids other than glutamate.

The dry composition may further comprise an essential fatty acid, such as an omega-3 fatty acid.

The dry composition may further comprise at least one mineral. The mineral may be selected from a group consisting of iron, copper, chromium, fluoride, iodine, manganese, molybdenum, selenium, and zinc. In some embodiments, the dry composition comprises at least 0.3 µg of mineral. For example, the dry composition may comprise at least 1 µg of mineral.

In certain embodiments, the dry composition is stored in a container. The container may be a dialysis bag. The dialysis bag may be intended for single-use. The dry composition may be a dialysis mixture. In some embodiments, the dry composition further comprises an aqueous solution in the container, thereby producing a mixture. The container may comprise approximately 2000 mL of aqueous solution. The container may comprise approximately 2500 mL of aqueous solution. The mixture may have a pH of 4.0-6.5. The mixture may have an osmolarity of 300-720 mOsmol/L.

In certain embodiments, the amount of at least one ion is at least 100 µmol.

In certain embodiments, the dry composition further comprises at least one nonessential amino acid. The amount of nonessential amino acid may be at least 1 µg. In some embodiments, the amount of nonessential amino acid is 1-100 µg.

The dry composition may comprise 0-5 mg of cysteine and/or cystine. In some embodiments, the dry composition comprises 0-1 mg of cysteine and/or cystine.

In some aspects, the present disclosure provides a concentrated composition comprising a dry composition described herein, and an initial aqueous solution, wherein the dry composition is dissolved in the initial aqueous solution.

In some aspects, the present disclosure provides a food composition comprising: (a) a cysteine devoid protein source; (b) at least one essential amino acid; and (c) at least one nonessential amino acid selected from a group consisting of alanine, asparagine, aspartate, glutamic acid, glycine, and proline, wherein each nonessential amino acid is 0-1% wt/wt of protein in the food composition, wherein the food composition comprises 0-1% cysteine and/or cystine wt/wt of protein in the food composition, and wherein the food composition comprises at least 6% wt/wt of protein.

For the food composition, in certain embodiments, the amount of nonessential amino acid selected from a group consisting of alanine, asparagine, aspartate, glutamic acid, glycine, and proline is 0-0.1% wt/wt of protein in the food composition. In some aspects, the food composition comprises at least two nonessential amino acid selected from a group consisting of alanine, asparagine, aspartate, glutamic acid, glycine, and proline. The food composition may comprise at least three nonessential amino acid selected from a group consisting of alanine, asparagine, aspartate, glutamic acid, glycine, and proline. The food composition may comprise at least four nonessential amino acid selected from a group consisting of alanine, asparagine, aspartate, glutamic acid, glycine, and proline. The food composition may comprise at least five nonessential amino acid selected from a group consisting of alanine, asparagine, aspartate, glutamic acid, glycine, and proline. The food composition may comprise at least six nonessential amino acid selected from a group consisting of alanine, asparagine, aspartate, glutamic acid, glycine, and proline. In some embodiments, the nonessential amino acid is glycine. In some embodiments, the nonessential amino acid is proline.

In certain embodiments, the amount of cysteine is 0-0.1% wt/wt of protein in the food composition.

In some aspects, the present disclosure provides a food composition comprising: (a) a cysteine devoid protein source; (b) at least one essential amino acid; and (c) at least six nonessential amino acids selected from the group consisting of alanine, asparagine, aspartate, glutamic acid, glycine, proline, glutamine, serine, tyrosine, and cysteine, wherein each nonessential amino acid is 0-1% wt/wt of protein in the food composition, and wherein the food composition comprises at least 6% wt/wt of protein.

For the food composition, in certain embodiments, the amount of each nonessential amino acid selected from a group consisting of alanine, asparagine, aspartate, glutamic acid, glycine, proline, glutamine, serine, tyrosine, and cysteine is 0-50%. In some embodiments, the food composition comprises at least seven nonessential amino acid selected from a group consisting of alanine, asparagine, aspartate, glutamic acid, glycine, proline, glutamine, serine, tyrosine, and cysteine. The food composition may comprise at least eight nonessential amino acid selected from a group consisting of alanine, asparagine, aspartate, glutamic acid, glycine, proline, glutamine, serine, tyrosine, and cysteine. The food composition may comprise at least nine of the nonessential amino acid selected from a group consisting of alanine, asparagine, aspartate, glutamic acid, glycine, proline, glutamine, serine, tyrosine, and cysteine. The food composition may comprise at least ten nonessential amino acid selected from a group consisting of alanine, asparagine, aspartate, glutamic acid, glycine, proline, glutamine, serine, tyrosine, and cysteine. In some embodiments, at least six nonessential amino acids are selected from the group consisting of glycine, proline, glutamine, serine, tyrosine, and cysteine. In an exemplary embodiment, at least one nonessential acid is cysteine. The amount of cysteine and/or cystine may be 0-0.04% wt/wt of protein in the food composition.

In some aspects, the present disclosure provides a food composition comprising: (a) at least one essential amino acid; and (b) glutamate, wherein the food composition is substantially free of nonessential amino acids other than glutamate.

In any of the food compositions disclosed herein, the amount of the cysteine devoid protein source is at least 1 wt/wt of the food composition. The amount of the cysteine devoid protein source may be 1-5% of the food composition. In an exemplary embodiment, the cysteine devoid protein source is gelatin.

In any of the food compositions disclosed herein, further comprising glutamate. In some embodiments, the food composition comprises approximately 0.1 mg to 50 mg of glutamate.

In any of the food compositions disclosed herein, the essential amino acid is selected from a group consisting of arginine, histidine, isoleucine, leucine, lysine, methionine, phenylalanine, threonine, tryptophan, and valine. In an exemplary embodiment, the essential amino acid is methionine. The essential amino acid may be at least 1.0% wt/wt of the food composition. For example, the amount of essential amino acid may be 2.0-75% wt/wt of the food composition. In some embodiments, the food composition comprises at least two essential amino acids. The food composition may comprise at least three essential amino acids. The food composition may comprise at least four essential amino acids. The food composition may comprise at least five essential amino acids. The food composition may comprise at least six essential amino acids. The food composition may comprise at least seven essential amino acids. The food composition may comprise at least eight essential amino acids.

In certain embodiments, any food composition described herein further comprises a pharmaceutically active agent. The pharmaceutically active agent may be an anti-cancer therapeutic.

In any of the food compositions disclosed herein, the food composition is packaged as a solid food, semi-solid food, or beverage. The food composition is packaged as a food product selected from a group consisting of a snack bar, cereal product, bakery product, and dairy product. For example, the food composition may be baby formula. The food composition may be a soft drink. The food composition may be a nutritional shake. The food composition is a granola bar.

In some embodiments, the food composition comprises 10-20% w/w of total amino acids. The food composition may comprise approximately 17% w/w of total amino acids.

In some aspects, the present disclosure provides a facility comprising a plurality of the liquid compositions described herein. The facility may be a pharmaceutical manufacturing site. The facility may be a distribution center. The facility may be a hospital or clinic.

In some aspects, the present disclosure provides a plurality of the dry compositions described herein. The facility may be a pharmaceutical manufacturing site. The facility may be a distribution center. The facility may be a hospital or clinic.

In some aspects, the present disclosure provides a plurality of the food composition described herein. The facility may be a food manufacturing site. The facility may be a distribution center. The facility may be a commercial kitchen, restaurant or eating facility.

In some aspects, the present disclosure provides a kit comprising: (a) a pre-packaged liquid composition described herein; and (b) instructions for using the pre-packaged liquid composition. In some embodiments, the kit provides complete treatments for at least one week. For example, the kit may provide complete treatments for at least four weeks.

In some aspects, the present disclosure provides a kit comprising: (a) a pre-packaged dry composition or concentrated composition described herein; and (b) instructions for using the pre-packaged dry composition or concentrated composition. In some embodiments, the kit provides complete treatments for at least one week. For example, the kit provides complete treatments for at least four weeks.

In some aspects, the present disclosure provides a kit comprising: (a) a pre-packaged food composition described herein; and (b) instructions for using the pre-packaged food composition. In some embodiments, the kit provides complete meals for at least one day. For example, the kit may provide complete meals for at least five days. In some embodiments, the kit further comprises a pre-packaged liquid composition described herein. The kit may further comprise instructions for using the pre-packaged liquid composition. In another embodiment, the kit further comprises a pre-packaged dry composition described herein. The kit further comprises instructions for using the pre-packaged dry composition.

In some aspects, the present disclosure provides a method for treating cancer in a subject in need thereof, the method comprising administering to the subject any food composition described herein, and administering to the subject a liquid composition, a concentrated composition or a dry composition described herein.

In some aspects, the present disclosure provides a method for treating cancer in a subject in need thereof, the method comprising administering to the subject a liquid composition, a concentrated composition or a dry composition described herein.

In some aspects, the present disclosure provides a method for treating cancer in a subject in need thereof, the method comprising administering to the subject any food composition described herein.

In any of the methods for treating cancer, the cancer may be selected from the group consisting of liver cancer, breast cancer, lung cancer, leukemia, prostate, and colon cancer. The subject may be human. The subject may be an animal. In some embodiments, the subject has a genetic predisposition for cancer. The subject may have elevated cysteine biosynthetic gene expression levels.

In certain embodiments, treating cancer is characterized by a reduction in tumor size. The tumor may be reduced by at least 30%. The tumor may be reduced by at least 50%. The tumor may be reduced by at least 80%.

In some embodiments, treating cancer is characterized by decreased levels of plasma cysteine. The levels of plasma cysteine may be reduced by at least 30%. The levels of plasma cysteine may be reduced by at least 50%. The levels of plasma cysteine may be reduced by at least 80%. The levels of plasma cysteine may be reduced by at least 90%. In an exemplary embodiment, the levels of plasma cysteine are reduced by at least 95%.

In some aspects, the present disclosure provides a method for reducing tumor size in a subject in need thereof, the method comprising administering to the subject any food composition described herein, and administering to the subject a liquid composition, a concentrated composition or a dry composition described herein.

In some aspects, the present disclosure provides a method for reducing tumor size in a subject in need thereof, the method comprising administering to the subject a liquid composition, a concentrated composition or a dry composition described herein.

In some aspects, the present disclosure provides a method for reducing tumor size in a subject in need thereof, the method comprising administering to the subject any food composition described herein.

In any of the methods for reducing tumor size, the subject may be human. The subject may be an animal. In some embodiments, the subject has a genetic predisposition for cancer. The subject may have elevated cysteine biosynthetic gene expression levels.

In certain embodiments, reducing tumor size is characterized by a reduction in tumor size. The tumor may be reduced by at least 30%. The tumor may be reduced by at least 50%. The tumor may be reduced by at least 80%.

In some aspects, the present disclosure provides a method for treating obesity, the method comprising administering to the subject any food composition described herein.

In any of the methods for treating obesity, the subject may be human. The subject may be an animal. In some embodiments, the subject has a genetic predisposition for obesity.

In some embodiments, treating obesity is characterized by the subject losing at least 10% of the subject's initial body weight. Treating obesity may be characterized by the subject losing at least 20% of the subject's initial body weight. Treating obesity may be characterized by the subject losing at least 30% of the subject's initial body weight.

In some aspects, the present disclosure provides a method for treating renal disease, the method comprising administering to the subject a liquid composition, a concentrated composition or a dry composition described herein.

In any of the methods for treating renal disease, the subject may be human. The subject may be an animal. In an exemplary embodiment, the subject is diagnosed with chronic kidney disease.

In any of the methods comprising administering to the subject a liquid composition, a concentrated composition or a dry composition described herein, the methods further comprise utilizing a membrane. In certain embodiments, the membrane comprises modified cellulose diacetate or polysulfone. In an exemplary embodiment, the membrane is a low-flux membrane. The low-flux membrane may permit small molecule exchange. In some embodiments, the low-flux membrane comprises a plurality of pores, and the plurality of pores comprises a first end and a second end. The plurality of pores may have an average pore diameter of approximately 1.8 nm.

In certain embodiments, the low-flux membrane permits approximately 50% or higher of a molecule weighing approximately 500 Daltons or less to move through the plurality of pores, from the first end to the second end. The low-flux membrane may permit approximately 75% or higher of a molecule weighing approximately 500 Daltons or less to move through the plurality of pores, from the first end to the second end. The low-flux membrane may permit approximately 90% or higher of a molecule weighing approximately 500 Daltons or less to move through the plurality of pores, from the first end to the second end. The low-flux membrane may permit approximately 95% or higher of a molecule weighing approximately 500 Daltons or less to move through the plurality of pores, from the first end to the second end.

In certain embodiments, approximately 20% of a molecule of at least 1000 Daltons passes through the plurality of pores, from the first end to the second end. For example, approximately 10% of a molecule of at least 1000 Daltons may pass from the first side to the second side. Approximately 1% of a molecule of at least 1000 Daltons may pass from the first side to the second side.

In any of the methods comprising administering the liquid composition, concentrated composition, or dry composition, in certain embodiments, the composition is administered to the subject at least once a week. The composition may be administered to the subject at least three times a week. The composition may be administered to the subject at least five times a week. In certain embodiments, the liquid composition, concentrated composition, or dry composition is administered to the subject over the course of at least one week. The composition may be administered to the subject over the course of at least four weeks. The composition may be administered to the subject over the course of at least 2 months. In an exemplary embodiment, the composition is administered to the subject over the course of at least 3 months.

In any of the methods comprising administering any food composition described herein, in certain embodiments, the food composition is administered to the subject at least once a week. The food composition may be administered to the subject at least three times a week. The food composition may be administered to the subject at least five times a week. The food composition may be administered to the subject at least twenty-one times a week.

In certain embodiments, the food composition is administered to the subject over the course of at least one week. The food composition may be administered to the subject over the course of at least four weeks. The food composition may be administered to the subject over the course of at least 2 months. The food composition may be administered to the subject over the course of at least 3 months.

In any of the methods comprising administering a liquid composition, concentrated composition or dry composition, and any food composition, the compositions may be administered to the subject sequentially. In another embodiment, the compositions may be administered to the subject simultaneously. In some embodiments, the compositions are administered to the subject at least once a week. For example, the compositions may be administered to the subject at least three times a week. In some embodiments, the compositions are administered to the subject over the course of at least one week. For example, the compositions may be administered to the subject over the course of at least four weeks.

In any of the methods described herein, in certain embodiments, the methods further comprise administering a pharmaceutically active agent. The pharmaceutically active agent may be an anti-cancer therapeutic. The pharmaceutically active agent may be provided in a subtherapeutic amount.

In any of the methods described herein, in certain embodiments, the methods further comprise administering a nutritional supplement. The nutritional supplement may comprise at least one amino acid selected from a group consisting of arginine, histidine, isoleucine, lysine, methionine, phenylalanine, threonine, tryptophan, and valine. In some embodiments, the nutritional supplement provides the subject with nutrients at levels in accordance with the Recommended Dietary Allowances (RDAs), Adequate Intakes (AIs), and/or Daily Value (DV).

In some aspects, the disclosure provides a method of treating cancer in a subject that has been placed on a low-cysteine diet, comprising: placing the subject under dialysis, wherein the dialysis reduces or depletes cysteine from the subject's body.

In some aspects, the disclosure provides a method of depleting cysteine in a subject that has been placed on a low-cysteine diet, comprising: placing the subject under dialysis, wherein the dialysis reduces or depletes cysteine from the subject's body.

In some aspects, the disclosure provides a method of treating cancer in a subject that has been placed on a dialysis procedure to reduce cysteine in the blood, comprising: placing the subject on a low-cysteine diet.

In some embodiments, the dialysis comprises administering a liquid composition disclosed herein, a concentrated composition disclosed herein or a dry composition disclosed herein. In some embodiments, the low-cysteine diet is a food composition disclosed herein.

In some aspects, the disclosure provides a dialysis system, comprising: a dialysis container comprising a liquid composition disclosed herein, a concentrated composition disclosed herein or a dry composition disclosed herein.

In some aspects, the disclosure provides a dialysis system, comprising: a dialysis container comprising a liquid composition disclosed herein, a concentrated composition disclosed herein or a dry composition disclosed herein, and a dialysis machine configured to administer the liquid composition, the concentrated composition or the dry composition. In some embodiments, the dialysis machine comprises a pump, a pressure monitor, air trap, air detector, a clamp, and/or a filter.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

A description of various aspects, features, embodiments, and examples is provided herein with reference to the accompanying drawings, which are briefly described below. The drawings may illustrate one or more aspect(s), feature(s), embodiment(s), and/or example(s) in whole or in part. The drawings are illustrative and are not necessarily drawn to scale.

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2 shows an overview of the diets used in colon, breast, prostate, and pancreatic cancer studies.

FIG. 3 shows an overview of the diet compositions used in the studies of the present disclosure. The mice used for the study were normal and active (other than tumor-bearing.)

FIG. 8 shows an overview of the dialysis compositions used in the studies of the present disclosure.

DETAILED DESCRIPTION

Figure 1:
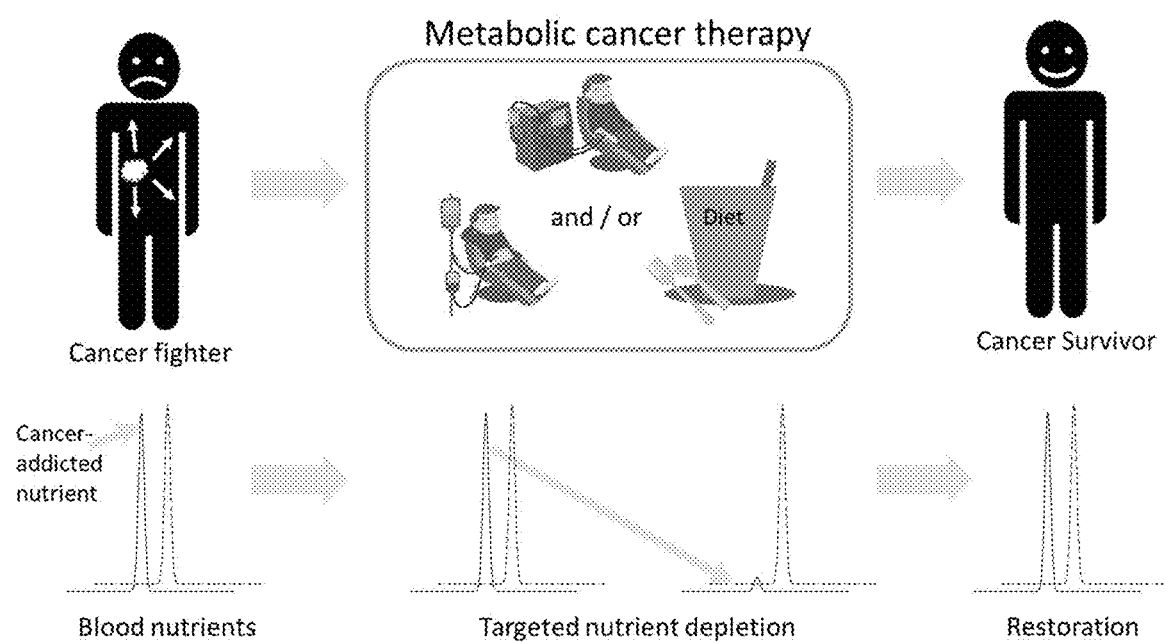
FIG. 1 depicts a metabolic cancer therapy in which a cancer patient is treated with dialysis and/or a nutritional diet in order to deplete targeted nutrient(s).

Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. Unless stated otherwise, the present invention is not limited by the illustrated ordering of acts or events, as some acts may occur in different orders and/or concurrently with other acts or events. Furthermore, not all illustrated acts or events are required to implement a methodology in accordance with the present invention. The concentration of various components in the disclosed compositions is exemplary and not meant to be limited to the recited concentration per se.

It will be understood that a word appearing herein in the singular encompasses its plural counterpart, and a word appearing herein in the plural encompasses its singular counterpart, unless implicitly or explicitly understood or stated otherwise. Further, it will be understood that for any given component described herein, any of the possible candidates or alternatives listed for that component, may generally be used individually or in any combination with one another, unless implicitly or explicitly understood or stated otherwise. Additionally, it will be understood that any list of such candidates or alternatives, is merely illustrative, not limiting, unless implicitly or explicitly understood or stated otherwise. Still further, it will be understood that any figure or number or amount presented herein is approximate, and that any numerical range includes the minimum number and the maximum number defining the range, whether the word "inclusive" or the like is employed or not, unless implicitly or explicitly understood or stated otherwise. Generally, the term "approximately" or "about" or the symbol "~" in reference to a figure or number or amount includes numbers that fall within a range of ±5% of same, unless implicitly or explicitly understood or stated otherwise. Yet further, it will be understood that any heading employed is by way of convenience, not by way of limitation. Additionally, it will be understood that any permissive, open, or open-ended language encompasses any relatively permissive to restrictive language, less open to closed language, or less open-ended to closed-ended language, respectively, unless implicitly or explicitly understood or stated otherwise. Merely by way of example, the word "comprising" may encompass "comprising", "consisting essentially of", and/or "consisting of" type language.

As used herein, unless otherwise indicated, some inventive embodiments herein contemplate numerical ranges. A variety of aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range as if explicitly written out. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. When ranges are present, the ranges include the range endpoints.

Definitions

The terms "administer", "administered", "administers" and "administering" are defined as the providing a composition to a subject via a route known in the art, including but not limited to intravenous, intraarterial, oral, parenteral, buccal, topical, transdermal, rectal, intramuscular, subcutaneous, intraosseous, transmucosal, or intraperitoneal routes of administration. In certain embodiments of the subject application, oral routes of administering a composition may be preferred. In certain embodiments, administering a composition through dialysis may be preferred.

As used herein, "agent" or "biologically active agent" refers to a biological, pharmaceutical, or chemical compound or other moiety. Non-limiting examples include simple or complex organic or inorganic molecule, a peptide, a protein, a peptide nucleic acid (PNA), an oligonucleotide (including e.g., aptamer and polynucleotides), an antibody, an antibody derivative, antibody fragment, a vitamin derivative, a carbohydrate, a toxin, a branched chain amino acid in free amino acid form or metabolite thereof, or a chemotherapeutic compound. As used herein, the term protein includes an amino acid mixture comprising one or more amino acids. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like. A skilled artisan can readily recognize that there is no limit as to the structural nature of the agents of the present invention.

As used herein, the terms "co-administration", "administered in combination with" and their grammatical equivalents are meant to encompass administration of the invention composition and additional therapeutic agent to a single subject. Co-administration can encompass administration of two or more agents to an animal so that both agents and/or their metabolites are present in the subject at the same time. Co-administration can encompass treatment regimens in which the composition and additional therapeutic agent are administered by the same or different route of administration or at the same or different times. Co-administration includes simultaneous administration in separate compositions, administration at different times in separate compositions, or administration in a composition in which both agents are present. Co-administration can include simultaneous administration of the agents in separate compositions, administration at different times in separate compositions, and/or administration in a single composition comprising each of the agents to be co-administered.

The terms "determining", "measuring", "evaluating", "assessing," "assaying," "interrogating," and "analyzing" are used interchangeably herein to refer to any form of measurement, and include determining if an element is present or not. These terms include both quantitative and/or qualitative determinations. Assessing may be relative or absolute.

The term "effective amount" or "therapeutically effective amount" refers to that amount of a compound described herein that is sufficient to effect the intended application including but not limited to disease treatment, as defined below. The therapeutically effective amount may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of proliferation or down regulation of activity of a target protein. The specific dose will vary depending on the particular compounds chosen, the dosing regimen to be followed, whether it is administered in combination with other compounds, timing of administration, the tissue to which it is administered, and the physical delivery system in which it is carried.

The term "essential amino acid" or "indispensable amino acid" refers to an amino acid that cannot be synthesized de novo by the organism. Essential amino acids include arginine, histidine, isoleucine, leucine, lysine, methionine, phenylalanine, threonine, tryptophan, and valine. Essential amino acids may include salts thereof.

The term "free", as used herein, refers to compositions that have about 0% of a specific component.

The term "nonessential amino acid" or "dispensable amino acid" refers to an amino acid that can be synthesized de novo by the organism. Nonessential amino acids include alanine, asparagine, aspartate, cysteine (or cystine), glutamic acid, glutamine, glycine, proline, serine, and tyrosine. The terms "cysteine" and "cystine" are used interchangeably herein. Nonessential amino acids may also include salts thereof.

The term "prevention" refers to providing treatment prior to the onset of a condition. If treatment is commenced in subjects with a condition, such treatment is expected to prevent, or to prevent the progression of, the medical sequelae of the condition.

As used herein, the term "subject" or "individual" includes mammals. Non-limiting examples of mammals include humans and animals, such as mice, including transgenic and non-transgenic mice. The methods described herein can be useful in both human therapeutics, pre-clinical, and veterinary applications. In some embodiments, the subject is an animal, and in some embodiments, the subject is human. Other mammals include, and are not limited to, apes, chimpanzees, orangutans, monkeys; domesticated animals (pets) such as dogs, cats, guinea pigs, hamsters, mice, rats, rabbits, and ferrets; domesticated farm animals such as cows, buffalo, bison, horses, donkey, swine, sheep, and goats; or exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, pandas, giant pandas, hyena, seals, sea lions, and elephant seals.

The term "substantially free", as used herein, refers to compositions that have less than about 10%, less than about 5%, less than about 1%, less than about 0.5%, less than 0.1% or even less of a specified component.

A "subtherapeutic amount" or "sub-therapeutic amount" of an agent, an activator or a therapy is an amount less than the effective amount for that agent, activator or therapy, but when combined with an effective or sub-therapeutic amount of another agent or therapy can produce a desired result, due to, for example, synergy in the resulting efficacious effects, and/or reduced side effects. A sub-therapeutic amount of the agent or component can be such that it is an amount below which would be considered therapeutic. For example, FDA guidelines can suggest a specified level of dosing to treat a particular condition, and a sub-therapeutic amount would be any level that is below the FDA suggested dosing level. The sub-therapeutic amount can be about 1, 5, 10, 15, 20, 25, 30, 35, 50, 75, 90, or 95% less than the amount that is considered to be a therapeutic amount. The therapeutic amount can be assessed for individual subjects, or for groups of subjects. The group of subjects can be all potential subjects, or subjects having a particular characteristic such as age, weight, race, gender, or physical activity level.

Compositions

As used herein "composition" refers to a dry composition, a concentrated composition, a liquid composition, and/or a food composition. The present disclosure provides for compositions, such as dry compositions, concentrated compositions, liquid compositions, and food compositions, effective for treating cancer, other metabolic diseases, including obesity, and renal disease. The compositions can be depleted or reduced with respect to one or more amino acids or other nutrients and/or supplemented with respect to one or more other amino acids or nutrients. The depleted or reduced nutrients can be certain nutrients acids that are demanded at a higher degree by cancerous cells as compared to non-cancerous cells. For example, cancerous cells may have a higher nutritional or metabolic requirement for certain non-essential amino acids as compared to non-cancerous cells and so a composition may formulated to be depleted or reduced with respect to those non-essential amino acids while maintaining the normal or supplemented amounts of other nutrients. The compositions may be a composition for dialysis or for a nutritional diet. As used herein, a dry composition, a concentrated composition, or a liquid composition may also be referred as a "dialysate composition," "dialysate," a "dialysis solution," or a "dialysis composition. As used herein, a food composition may also be referred to as a "nutritional diet" or a "diet."

Liquid Composition

The present disclosure provides dialysis compositions. The dialysis composition may be in the form of a liquid composition. In some aspects, the present disclosure provides a liquid composition comprising glutamate. In some embodiments, the liquid composition comprises glutamate and at least one essential amino acid. The present disclosure also provides a dialysis composition comprising at least one vitamin. In some embodiments, the liquid composition comprises at least one vitamin and at least one essential amino acid. In some embodiments, the liquid composition is substantially free of cysteine and/or cystine.

In some aspects, the present disclosure provides, a liquid composition comprising: (a) carbohydrate; (b) glutamate; (c) at least one vitamin; (d) at least one ion selected from a group consisting of sodium, calcium, magnesium, chloride, and lactate; (e) at least one essential amino acid; and (f) an aqueous solution, wherein the liquid composition comprises 0-5 µM of cysteine and/or cystine, wherein said liquid composition has a pH of 4.0-6.5, and wherein said liquid composition has an osmolarity of 300-720 mOsmol/L. In some aspects, the present disclosure provides, a liquid composition comprising: (a) carbohydrate; (b) at least one vitamin; (c) at least one ion selected from a group consisting of sodium, calcium, magnesium, chloride, and lactate; (d) at least one essential amino acid; and (e) an aqueous solution, wherein the liquid composition optionally comprises glutamate, wherein the liquid composition comprises 0-5 µM of cysteine and/or cystine, wherein said liquid composition has a pH of 4.0-6.5, and wherein said liquid composition has an osmolarity of 300-720 mOsmol/L.

In some aspects, the present disclosure provides, a liquid composition comprising: (a) carbohydrate; (b) glutamate; (c) at least one ion selected from a group consisting of sodium, calcium, magnesium, chloride, and lactate; (d) at least one essential amino acid; and (e) an aqueous solution, wherein the liquid composition is substantially free of nonessential amino acids other than glutamate, wherein the liquid composition comprises 0-5 µM of cysteine and/or cystine, wherein said liquid composition has a pH of 4.0-6.5, and wherein said liquid composition has an osmolarity of 300-720 mOsmol/L. In some aspects, the present disclosure provides a liquid composition comprising: (a) carbohydrate; (b) at least one vitamin; (c) at least one ion selected from a group consisting of sodium, calcium, magnesium, chloride, and lactate; (d) at least one essential amino acid; and (e) an aqueous solution, wherein the liquid composition optionally comprises glutamate, wherein the liquid composition is substantially free of nonessential amino acids selected from alanine, asparagine, aspartate, cysteine, glycine, proline, glutamine, serine, and tyrosine, wherein the liquid composition comprises 0-5 µM of cysteine and/or cystine, wherein said liquid composition has a pH of 4.0-6.5, and wherein said liquid composition has an osmolarity of 300-720 mOsmol/L.

In some aspects, the present disclosure provides a liquid composition comprising: (a) carbohydrate; (b) at least one ion selected from a group consisting of sodium, calcium, magnesium, chloride, and lactate; (c) at least one essential amino acid; and an aqueous solution, wherein the liquid composition comprises 0-50 µM of cysteine and/or cystine, wherein liquid composition has a pH of 4.0-6.5, and wherein the liquid composition has an osmolarity of 300-720 mOsmol/L.

In some aspects, the present disclosure provides a liquid composition comprising: (a) dextrose; (b) at least one ion selected from a group consisting of sodium, calcium, magnesium, chloride, and lactate; (c) at least one essential amino acid; and an aqueous solution, wherein the liquid composition comprises at least 10 µM of essential amino acid, wherein the liquid composition comprises 0-50 µM of cysteine and/or cystine, wherein liquid composition has a pH of 4.0-6.5, and wherein the liquid composition has an osmolarity of 300-720 mOsmol/L.

In some aspects, the present disclosure provides a liquid composition comprising: (a) carbohydrate; (b) at least one essential amino acid; and an aqueous solution, wherein the liquid composition comprises 0-50 µM of cysteine and/or cystine, and wherein the liquid composition is substantially free of nonessential amino acids.

In some embodiments, the carbohydrate is selected from a group consisting of dextrose, glucose, sucrose, fructose, and lactose. In an exemplary embodiment, the carbohydrate is dextrose. The liquid composition disclosed herein may comprise amount of dextrose that is 0.1-4.5% w/v. In certain embodiments, the amount of the dextrose is 1.0-4.5% w/v. The amount of the dextrose may be 1.5-4.25% w/v. In an exemplary embodiment, the amount of the dextrose is 1.7-4.0% w/v. In another embodiment, the amount of dextrose is 0.05-0.25% w/v. The amount of the dextrose may be 0.08-0.22% w/v. In an exemplary embodiment, the amount of the dextrose is 0.1-0.2% w/v. The amount of dextrose in the liquid composition may be at least, approximately, or no more than 0.05, 0.1, 0.5, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0% w/v. The amount of dextrose in the liquid composition may depend on its intended application, such as use in peritoneal dialysis (PD) or use in hemodialysis (HD). For example, when used for peritoneal dialysis, the amount of dextrose in the liquid composition may be 1.0-4.5% w/v, such as 1.5-4.25% w/v or 1.7-4.0% w/v. When used for hemodialysis, the amount of dextrose in the liquid composition may be 0.05-0.50% w/v, such as 0.08-0.25% w/v or 0.1-0.25% w/v.

In certain embodiments, the liquid composition comprises at least one essential amino acid selected from a group consisting of histidine, isoleucine, leucine, lysine, methionine, phenylalanine, threonine, tryptophan, valine, and arginine. In an exemplary embodiment, at least one of the essential amino acids is methionine. In an exemplary embodiment, at least one of the essential amino acids is arginine. In certain embodiments, the amount of at least one of the essential amino acid is at least 10 µM. The amount of at least one of the essential amino acid may be 10-300 µM. The amount of at least one of the essential amino acid may be 20-250 µM. The amount of at least one of the essential amino acid may be at least, approximately, or no more than 1, 5, 10, 20, 30, 40, 50, 60, 70, 80, 90, 100, 110, 120, 130, 140, 150, 160, 170, 180, 190, 200, 210, 220, 230, 240, 250, 260, 270, 280, 290, or 300 µM.

In certain embodiments, the liquid composition comprises at least two essential amino acids. The liquid composition may comprise at least three essential amino acids. The liquid composition may comprise at least four essential amino acids. The liquid composition may comprise at least five essential amino acids. The liquid composition may comprise at least six essential amino acids. The liquid composition may comprise at least seven essential amino acids. The liquid composition may comprise at least eight essential amino acids. The liquid composition may comprise at least nine essential amino acids. The liquid composition may comprise at least ten essential amino acids.

In certain embodiments, the liquid composition comprises at least one vitamin. The vitamin may be selected from a group consisting of vitamin A, vitamin B, vitamin C, vitamin D, vitamin E, vitamin K, and choline. In some embodiments, the amount of vitamin is at least, approximately, or no more than about 0.00001, 0.0001, 0.001, 0.01, 0.1, 1, 25, 50, 75, 100, 125, 150, 175 or 200 µM. The amount of vitamin may be approximately about 0.000010 to 200 µM. In some embodiments, the liquid composition comprises approximately at least 0.001, 100, or 1000 µM of at least one vitamin. In an exemplary embodiment, the vitamin is vitamin C. In one embodiment, the liquid composition comprises at least approximately 1 µM of the vitamin C. The liquid composition may comprise at least approximately 7 µM of the vitamin C. The liquid composition may comprise at least approximately 1, 2, 3, 4, 5, 6, 7, 8, 9, or 10 µM of vitamin C. In an exemplary embodiment, the vitamin is vitamin B. In some embodiments, the liquid composition comprises 0.000005 to 1500 µM of said vitamin B, such as 0.00005, 0.0005, 0.005, 0.05, 0.5, 1, 10, 100, 1000 or 1500 µM. Vitamin B may include biotin, vitamin B1, vitamin B2, vitamin B3, vitamin B5, vitamin B6, vitamin B9, and/or vitamin B12.

In certain embodiments, the liquid composition comprises glutamate. The amount of glutamate may be at least, approximately, or no more than 1, 5, 20, 50, 100, 200, 300, 400, 500, 750, or 1000 µM. The amount of glutamate may be approximately 2-500, 20-400, 75-300, or 100-200 µM. In some embodiments, the amount of glutamate increases glutamate in the blood by at least, approximately or no more than 25, 50, 75, 100, 125, 150, 175, 200, or 300 µM. In certain embodiments, the amount of glutamate increases glutamate in the blood by at least 150 µM.

In certain embodiments, the liquid composition further comprises an essential fatty acid, such as omega-6 and omega-3 fatty acids. In one embodiment, the essential fatty acid is an omega-3 fatty acid. The amount of essential fatty acid may be approximately 100, 150, 200, 250, 300, 350, 400, 450, 500, 600, 700, 800, 900, 1000, 1500, or 2000 mg per liter. In some embodiments, the amount of essential amino acids is 200-350 mg per liter.

In certain embodiments, the liquid composition further comprises at least one mineral. The mineral may be selected from a group consisting of iron, copper, chromium, fluoride, iodine, manganese, molybdenum, selenium, and zinc. In an embodiment, the liquid composition comprises at least 5 nM of the mineral. The amount of at least one of the mineral may be 5 nM-5 µM. In an exemplary embodiment, the liquid composition comprises 1 µM or more.

The liquid composition described herein comprises at least one ion. In certain embodiments, the amount of at least one ion is at least approximately 0.1 mEq/L. The amount of at least one ion may be 0.1-150 mEq/L. The amount of at least one ion may be at least approximately 0.1, 0.5, 1, 5, 10, 15, 20, 50, 75, 100, 125, or 150 mEq/L.

In some embodiments, the liquid composition is substantially free of at least one nonessential amino acid selected from alanine, asparagine, aspartate, cysteine, glycine, proline, glutamine, serine, and tyrosine. The liquid composition may be substantially free of at least 2, 3, 4, 5, 6, 7, 8, or 9 nonessential amino acids. The liquid composition may be free of at least one nonessential amino acid. The liquid composition may be free of at least 2, 3, 4, 5, 6, 7, 8, or 9 nonessential amino acids. The liquid composition may be free of nonessential amino acids other than glutamate. Alternatively, in certain embodiments, the liquid composition further comprises at least one nonessential amino acid. The nonessential amino acid can be selected from a group consisting of alanine, asparagine, aspartate, glutamic acid, glycine, proline, glutamine, serine, and tyrosine. In an embodiment, the liquid composition comprises at least two nonessential amino acids. The liquid composition may comprise at least three nonessential amino acids. The liquid composition may comprise at least four nonessential amino acids. The liquid composition may comprise at least five nonessential amino acids. The liquid composition may comprise at least six nonessential amino acids. The liquid composition may comprise at least seven nonessential amino acids. The liquid composition may comprise at least eight nonessential amino acids. The liquid composition may comprise at least nine nonessential amino acids. In one embodiment, the amount of the nonessential amino acid is at least 5 approximately µM, such as 5, 10, 50, 75, 100, 125, 150, 175, 200, 225, 250, 275, 300, 325, 350, 375, 400, 425, 450, 475, 500, 525, 550, 575, 600, 625, 650, 675, or 700 µM. The amount of the nonessential amino acid may be 5-600 µM.

The liquid composition may comprise less than approximately 5 µM of cysteine and/or cystine. For example, the amount of cysteine and/or cystine may be 0, 0.1, 0.5, 1, 1.5, 2, 2.5, 3, 3.5, 4, 4.5, or 5 µM. In certain embodiments, the liquid composition comprises 0-4 µM of cysteine and/or cystine. The liquid composition may comprise 0-2.5 µM of cysteine and/or cystine, such as 0-1 µM of cysteine and/or cystine. In an exemplary embodiment, the liquid composition is substantially free of cysteine and/or cystine. The liquid composition may be free of cysteine and/or cystine.

In certain embodiments, the liquid composition has a pH of 5.0-6.5. The liquid composition may have a pH of 5.5-6.0. For example, the liquid composition may have a pH of approximately 6.0. The liquid composition may have a pH of approximately 5.5. The liquid composition may have a pH of approximately 5.0.

In certain embodiments, the liquid composition has an osmolarity of 300-500. The liquid composition may have an osmolarity of 300-400. In one embodiment, the liquid composition has an osmolarity of 300-350. The liquid composition may have an osmolarity of 400-500.

The liquid composition contains an aqueous solution that may be a sterile solution or a nonsterile solution. In some embodiments, the aqueous solution is sterile. In other embodiments, the aqueous solution is nonsterile. The liquid composition may be stored in a container that is ready to be used by the subject. The container may comprise a sufficient amount of liquid composition for use in any of the methods described herein. For example, the container may hold approximately 1, 2, or 2.5 liter of liquid composition. The liquid composition may be available as a ready-for-use dialysis solution.

Dry Composition/Concentrated Composition

The present disclosure provides dialysis compositions. The dialysis composition may be in the form of a dry or concentrated composition. In some aspects, the present disclosure provides a dry or concentrated composition comprising glutamate. In some embodiments, the dry or concentrated composition comprises glutamate and at least one essential amino acid. The present disclosure also provides a dialysis composition comprising at least one vitamin. In some embodiments, the dry or concentrated composition comprises at least one vitamin and at least one essential amino acid. In some embodiments, the dry or concentrated composition is substantially free of cysteine and/or cystine.

In some aspects, the present disclosure provides, a dry composition comprising: (a) carbohydrate; (b) at least one vitamin; (c) at least one ion selected from a group consisting of sodium, calcium, magnesium, chloride, and lactate; (d) at least one essential amino acid; and (e) an aqueous solution, wherein the dry composition optionally comprises glutamate, wherein the dry composition comprises 0-5 µM of cysteine and/or cystine. In some aspects, the present disclosure provides, a dry composition comprising: (a) carbohydrate; (b) glutamate; (c) at least one vitamin; (d) at least one ion selected from a group consisting of sodium, calcium, magnesium, chloride, and lactate; and (e) at least one essential amino acid, wherein the dry composition comprises 0-10 mg of cysteine and/or cystine.

In some aspects, the present disclosure provides a dry composition comprising: (a) carbohydrate; (b) at least one vitamin; (c) at least one ion selected from a group consisting of sodium, calcium, magnesium, chloride, and lactate; (d) at least one essential amino acid; and (e) an aqueous solution, wherein the liquid composition optionally comprises glutamate, wherein the dry composition is substantially free of nonessential amino acids selected from alanine, asparagine, aspartate, cysteine, glycine, proline, glutamine, serine, and tyrosine, and wherein the dry composition comprises 0-5 µM of cysteine and/or cystine. In some aspects, the present disclosure provides, a dry composition comprising: (a) carbohydrate; (b) glutamate; (c) at least one ion selected from a group consisting of sodium, calcium, magnesium, chloride, and lactate; and (d) at least one essential amino acid, wherein the dry composition is substantially free of nonessential amino acids other than glutamate, and wherein the dry composition comprises 0-10 mg of cysteine and/or cystine.

In some aspects, the present disclosure provides a dry composition comprising: (a) dextrose; (b) at least one ion selected from a group consisting of sodium, calcium, magnesium, chloride, and lactate; and (c) at least one essential amino acid, wherein the dry composition comprises at least 2 µg essential amino acid, and wherein the dry composition comprises 0-10 µg of cysteine and/or cystine.

In some aspects, the present disclosure provides a dry composition comprising: (a) carbohydrate; (b) at least one essential amino acid, wherein the dry composition comprises 0-10 µg of cysteine and/or cystine.

The dry composition described herein may be advantageous since it may minimize storage space, weight, and transport of water and may also increase the stability and thereby also the shelf-life of the dialysis components. The dry composition may be stable for long term storage and transportation. The dry composition may be available in a container, in which an aqueous solution may be added to the container to reconstitute the contents therein. The container may have the capacity to hold approximately 1, 2, 2.5, 4 or 10 liter of aqueous solution. Aqueous solution may be added to the container prior to the administration of the composition to the subject for dialysis.

In some embodiments, the carbohydrate is selected from a group consisting of dextrose, glucose, sucrose, fructose, and lactose. In an exemplary embodiment, the carbohydrate is dextrose. The amount of dextrose in the dry composition may range from 0.1 g to 75 g. In certain embodiments, the amount of dextrose is approximately 5-75 g. The amount of the dextrose may be approximately 5, 10, 15, 20, 25, 30, 35, 40, 45, 50, 55, 60, 65, 70, or 75 g. The amount of the dextrose may be 10-50 g. In one embodiment, the amount of dextrose is approximately 10 g. In one embodiment, the amount of dextrose is approximately 50 g. In another embodiment, the amount of dextrose is 0.1 g-5 g. The amount of the dextrose may be approximately 0.1, 0.5, 1.0, 1.5, 2.0, 2.5, 3.0, 3.5, 4.0, 4.5 or 5.0 g. The amount of the dextrose may be 0.5-2.5 g. In one embodiment, the amount of dextrose is approximately 0.5 g. In one embodiment, the amount of dextrose is approximately 2 g. In certain embodiments, the amount of dextrose is approximately 10-99.5% of the total composition. For example, the amount of dextrose may be 10, 20, 30, 40, 50, 60, 70, 75, 80, 85, 90, 95, or 99.5% of the total composition. In an exemplary embodiment, the amount of dextrose is 70-95% of the total composition.

In certain embodiments, the dry composition comprises at least one essential amino acid selected from a group consisting of histidine, isoleucine, leucine, lysine, methionine, phenylalanine, threonine, tryptophan, valine, and arginine. In an exemplary embodiment, at least one of the essential amino acid is methionine. In an exemplary embodiment, at least one of the essential amino acid is arginine. In certain embodiments, the amount of each essential amino acid is at least 2 µg. The amount of each essential amino acid may be at least, approximately, or no more than 1, 2, 5, 10, 15, 20, 25, 30, 40, 50, 60, 70, 80, 90, 100, 300, 500, 1000, or 1500 µg. The total amount of the essential amino acids may be at least, approximately, or no more than 100, 150, 200, 250, 300, 500, 1000, 2000, 3000, 5000, 6000, 7000, 7500 or 8000 µg.

In an embodiment, the dry composition comprises at least two essential amino acids. The dry composition may comprise at least three essential amino acids. The dry composition may comprise at least four essential amino acids. The dry composition may comprise at least five essential amino acids. The dry composition may comprise at least six essential amino acids. The dry composition may comprise at least seven essential amino acids. The dry composition may comprise at least eight essential amino acids. The dry composition may comprise at least nine essential amino acids. The dry composition may comprise at least ten essential amino acids.

In certain embodiments, the dry composition comprises at least one vitamin. The vitamin may be selected from a group consisting of vitamin A, vitamin B, vitamin C, vitamin D, vitamin E, vitamin K, and choline. In some embodiments, the amount of vitamin is at least, approximately, or no more than 0.01, 0.05, 0.1, 0.5, 1, 10, 50, 100, 500, 750, 1000, 1250, or 1500 µg. The amount of vitamin may be approximately 0.01-1500 µg. In an exemplary embodiment, the vitamin is vitamin C. The dry composition may comprise at least approximately 1000 µg of vitamin C, such as approximately 1000, 1300, 1400, 1500, 1600, 1700, 1800, 1900, 2000, 2100, 2200, 2300, 2400, 2500, 2600, 2700, 2800, 2900, or 3000 µg of vitamin C. In an embodiment, the dry composition comprises at least approximately 2500 µg of vitamin C. The dry composition may comprise at least, approximately, or no more than 0.01 µg of vitamin B, such as approximately 0.01, 0.05, 0.1, 0.5, 1, 1.5, 5, 10, 50, or 100 µg of vitamin B. Vitamin B may include biotin, vitamin B1, vitamin B2, vitamin B3, vitamin B5, vitamin B6, vitamin B9, and/or vitamin B12.

In certain embodiments, the dry composition comprises at least, approximately, or no more than 0.1 mg of glutamate, such as approximately 0.1, 1, 5, 10, 15, 20, 25, 30, 35, 40, 45 or 50 mg. The amount of glutamate may be 0.1-50 mg, 5-25 mg, or 25-45 mg.

In certain embodiments, the dry composition further comprises an essential fatty acid, such as omega-6 and omega-3 fatty acids. In one embodiment, the essential fatty acid is an omega-3 fatty acid. In one embodiment, the essential fatty acid is an omega-3 fatty acid. The amount of essential fatty acid may be approximately 100, 150, 200, 250, 300, 350, 400, 450, 500, 750, 1000, 1100, 1200, 1300, 1400, 1500, 1600, 1700, 1800, 1900 or 2000 mg per liter. In some embodiments, the amount of essential amino acids is 1200-1600 mg per liter.

In certain embodiments, the dry composition further comprises at least one mineral. The mineral may be selected from a group consisting of iron, copper, chromium, fluoride, iodine, manganese, molybdenum, selenium, and zinc. In an embodiment, the dry composition comprises at least 0.3 µg of the mineral. For example, the dry composition comprises approximately 0.1, 1, 10, 50, 75, 100, 150, 200, 250, 300, 350, 400, 450, 500, 750, 1000, 1250, 1500, 2000, 2500, 3000, 3500, 4000, 4500, 5000 or 7500 µg. In an exemplary embodiment, the dry composition comprises approximately 400 µg. In another embodiment, the dry composition comprises approximately 800 µg.

The dry composition described herein comprises at least one ion. The ion may be, but are not limited to, sodium, calcium, magnesium, chloride, lactate or combinations thereof. In certain embodiments, the amount of at least one of the ion is at least approximately 0.1 µg. In one embodiment, the amount of at least one of the ion is at least approximately 0.5 µg. The amount of the ion may be at least approximately 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or 2.0 µg. In certain embodiments, the amount of the ion is at least approximately 50 µmol. In one embodiment, the amount of ion is at least approximately 100 µmol. The amount of ion may be at least approximately 200 µmol. The amount of ion may be at least approximately 250 µmol. The amount of the ion may be 50-300 µmol, such as 50, 60, 70, 80, 90, 100, 110, 120, 130, 140, 150, 160, 170, 180, 190, 200, 210, 220, 230, 240, 250, 260, 270, 280, 290, or 300 µmol.

In some embodiments, the dry composition is substantially free of at least one nonessential amino acid selected from alanine, asparagine, aspartate, cysteine, glycine, proline, glutamine, serine, and tyrosine. The dry composition may be substantially free of at least 2, 3, 4, 5, 6, 7, 8, or 9 nonessential amino acids. The dry composition may be free of at least one nonessential amino acid. The dry composition may be free of at least 2, 3, 4, 5, 6, 7, 8, or 9 nonessential amino acids. The dry composition may be free of nonessential amino acids other than glutamate. Alternatively, in certain embodiments, the dry composition further comprises at least one nonessential amino acid. The nonessential amino acid can be selected from a group consisting of alanine, asparagine, aspartate, glutamic acid, glycine, proline, glutamine, serine, and tyrosine. In an embodiment, the dry composition comprises at least two nonessential amino acids. The dry composition may comprise at least three nonessential amino acids. The dry composition may comprise at least four nonessential amino acids. The dry composition may comprise at least five nonessential amino acids. The dry composition may comprise at least six nonessential amino acids. The dry composition may comprise at least seven nonessential amino acids. The dry composition may comprise at least eight nonessential amino acids. The dry composition may comprise at least nine nonessential amino acids. In one embodiment, the amount of the nonessential amino acid is at least 1 mg. The amount of the nonessential amino acid may be 1-100 mg. In some embodiments, the amount of nonessential amino acid is 1-300 mg, such as 1, 50, 100, 150, 200, 250, or 300 mg.

The present disclosure provides a dry composition comprising less than 10 mg of cysteine and/or cystine. For example, the dry composition may comprise approximately 0, 0.5, 1, 1.5, 2, 2.5, 3, 3.5, 4, 4.5, 5, 5.5, 6, 6.5, 7, 7.5, 8, 8.5, 9, 9.5 or 10 mg of cysteine and/or cystine. In certain embodiments, the dry composition comprises 0-10 mg of cysteine and/or cystine. In one embodiment, the dry composition comprises 0-2.5 mg of cysteine and/or cystine. In an exemplary embodiment, the dry composition is substantially free of cysteine and/or cystine. The dry composition may be free of cysteine and/or cystine.

In an exemplary embodiment, the liquid composition or dry composition comprises methionine. The molar ratio of dextrose to methionine of the liquid composition or dry composition may be greater or less than approximately 1, 50, 100, 250, 500, 1,000, 2,000, 3,000, 4,000, 5,000, 6,000, 7,000, 8,000, 9,000, 10,000, 10,500, 20,000, 30,000, 40,000, 50,500, 60,000, 70,000, 80,000, 90,000, or 100,000. In an exemplary embodiment, the molar ratio of dextrose to methionine of the liquid composition or dry composition is greater or less than approximately 250, 500, 1,000, 2,000, 3,000, 4,000, 5,000, 6,000, 7,000, 8,000, 9,000, 10,000, or 10,500. In one embodiment, the molar ratio of dextrose to methionine of the compositions is approximately 250. In another embodiment, the molar ratio of dextrose to methionine of the compositions is approximately 10,500.

The molar ratio of cysteine to essential amino acids of the liquid composition or dry composition may be less than 0.01, 0.02, 0.03, 0.04, 0.05, 0.06, 0.08, 0.09, 0.1, 0.2, 0.3, 0.4, 0.5, 0.6, 0.7, 0.8, 0.9, 1, 2, 3, 4, 5, 10, 15, 20, 50, or 100. In one embodiment, the molar ratio of cysteine to methionine is less than 0.01, 0.02, 0.03, 0.04, 0.05, 0.06, 0.08, 0.09, 0.1, 0.2, 0.3, 0.4, 0.5, 0.6, 0.7, 0.8, 0.9, 1, 2, 3, 4, or 5.

The molar ratio of methionine to amino acids of the liquid composition or dry composition may be greater than about 0.01, 0.02, 0.03, 0.04, 0.05, 0.06, 0.08, 0.09, 0.1, 0.2, 0.3, 0.4, 0.5, 0.6, 0.7, 0.8, 0.9, 1, 2, 3, 4, 5, 10, 15, 20, 50, or 100. In some embodiments, the molar ratio of methionine to other amino acids of the liquid composition and dry composition may be greater than about 0.01, 0.02, 0.03, 0.04, 0.05, 0.06, 0.08, 0.09, 0.1, 0.2, 0.3, 0.4, 0.5, 0.6, 0.7, 0.8, 0.9, 1, 2, 3, 4, or 5.

In some embodiments, the molar ratio of methionine to alanine in the liquid composition or dry composition is greater than about 0.06, 0.08, 0.09, 0.1, 0.2, 0.3, 0.4, 0.5, 0.6, 0.7, 0.8, 0.9, 1, 2, 3, 4, or 5. In some embodiments, the molar ratio of methionine to arginine is greater than about 0.3, 0.4, 0.5, 0.6, 0.7, 0.8, 0.9, 1, 2, 3, 4, or 5. In some embodiments, the molar ratio of methionine to asparagine is greater than about 0.3, 0.4, 0.5, 0.6, 0.7, 0.8, 0.9, 1, 2, 3, 4, or 5. In some embodiments, the molar ratio of methionine to aspartic acid is greater than about 2, 3, 4, 5, 10, 15, 20, 50, or 100. In some embodiments, the molar ratio of methionine to β-alanine is greater than about 1, 2, 3, 4, 5, 10, 15, 20, 50, or 100. In some embodiments, the molar ratio of methionine to cystine is greater than about 0.5, 0.6, 0.7, 0.8, 0.9, 1, 2, 3, 4, or 5. In some embodiments, the molar ratio of methionine to glutamic acid is greater than about 0.3, 0.4, 0.5, 0.6, 0.7, 0.8, 0.9, 1, 2, 3, 4, or 5. In some embodiments, the molar ratio of methionine to glutamine is greater than about 0.04, 0.05, 0.06, 0.08, 0.09, 0.1, 0.2, 0.3, 0.4, 0.5, 0.6, 0.7, 0.8, 0.9, 1, 2, 3, 4, or 5. In some embodiments, the molar ratio of methionine to glycine is greater than about 0.1, 0.2, 0.3, 0.4, 0.5, 0.6, 0.7, 0.8, 0.9, 1, 2, 3, 4, or 5. In some embodiments, the molar ratio of methionine to histidine is greater than about 0.2, 0.3, 0.4, 0.5, 0.6, 0.7, 0.8, 0.9, 1, 2, 3, 4, or 5. In some embodiments, the molar ratio of methionine to isoleucine is greater than about 0.2, 0.3, 0.4, 0.5, 0.6, 0.7, 0.8, 0.9, 1, 2, 3, 4, or 5. In some embodiments, the molar ratio of methionine to leucine is greater than about 0.1, 0.2, 0.3, 0.4, 0.5, 0.6, 0.7, 0.8, 0.9, 1, 2, 3, 4, or 5. In some embodiments, the molar ratio of methionine to phenylalanine is greater than about 0.4, 0.5, 0.6, 0.7, 0.8, 0.9, 1, 2, 3, 4, or 5. In some embodiments, the molar ratio of methionine to proline is greater than about 0.1, 0.2, 0.3, 0.4, 0.5, 0.6, 0.7, 0.8, 0.9, 1, 2, 3, 4, or 5. In some embodiments, the molar ratio of methionine to serine is greater than about 0.2, 0.3, 0.4, 0.5, 0.6, 0.7, 0.8, 0.9, 1, 2, 3, 4, or 5. In some embodiments, the molar ratio of methionine to threonine is greater than about 0.1, 0.2, 0.3, 0.4, 0.5, 0.6, 0.7, 0.8, 0.9, 1, 2, 3, 4, or 5. In some embodiments, the molar ratio of methionine to tryptophan is greater than about 0.3, 0.4, 0.5, 0.6, 0.7, 0.8, 0.9, 1, 2, 3, 4, or 5. In some embodiments, the molar ratio of methionine to tyrosine is greater than about 0.3, 0.4, 0.5, 0.6, 0.7, 0.8, 0.9, 1, 2, 3, 4, or 5. In some embodiments, the molar ratio of methionine to valine is greater than about 0.09, 0.1, 0.2, 0.3, 0.4, 0.5, 0.6, 0.7, 0.8, 0.9, 1, 2, 3, 4, or 5.

In certain embodiments, the molar ratio of methionine to minerals in the dry composition or liquid composition, such as iron, copper, chromium, fluoride, iodine, manganese, molybdenum, selenium and zinc, of the liquid composition or dry composition is greater than about 1, 5, 7, 8, 9, 10, 40, 50, 75, 90, 100, 500, 1,000, 1,100, 1,500, 1,900, 2,000, 2,300, 2,500, 2,800, 3,000, 4,000, 5,000, 6,000, 7,000, 8,000, 9,000, or 10,000. The molar ratio of methionine to iron may be greater than about 9, 10, 40, 50, 75, 90, 100, 500, or 1,000. The molar ratio of methionine to copper may be greater than about 90, 100, 500, 1,000, 1,100, 1,500, 1,900, or 2,000. The molar ratio of methionine to chromium may be greater than about 2,300, 2,500, 2,800, 3,000, 4,000, 5,000, 6,000, 7,000, 8,000, 9,000, or 10,000. The molar ratio of methionine to fluoride may be greater than about 7, 8, 9, 10, 40, 50, 75, 90, 100, 500, or 1,000. The molar ratio of methionine to iodide may be greater than about 1,100, 1,500, 1,900, 2,000, 2,300, 2,500, 2,800, 3,000, 4,000, 5,000, 6,000, 7,000, 8,000, 9,000, or 10,000. The molar ratio of methionine to manganese may be greater than about 40, 50, 75, 90, 100, 500, or 1,000. The molar ratio of methionine to molybdenum may be greater than about 2,800, 3,000, 4,000, 5,000, 6,000, 7,000, 8,000, 9,000, or 10,000. The molar ratio of methionine to selenium may be greater than about 1,900, 2,000, 2,300, 2,500, 2,800, 3,000, 4,000, 5,000, 6,000, 7,000, 8,000, 9,000, or 10,000. The molar ratio of methionine to zinc may be greater than about 8, 9, 10, 40, 50, 75, 90, 100, 500, or 1,000.

In some embodiments, the dry composition, concentrated composition or liquid composition comprises one or more components, such as dextrose, ions, buffer, amino acids, vitamins and minerals, in terms of molar ratio (dextrose to component), as depicted in Table 1 below.

TABLE 1

| Dry Composition, Concentrated Composition and Liquid Composition Components | | |
|---|---|---|
| Dextrose (/L) | | mmole |
| Hemodialysis only (HD) | | 5.5-11.0 |
| peritoneal dialysis only (PD) | | 83-236 |
| Osmolarity (mOsmol/L) | | 300-718 |
| pH | | 6.0 (4.0-6.5) |

| Ionic Concentration (/L) | mmole | Molar Ratio Range (dextrose to ion) HD | Molar Ratio Range (dextrose to ion) PD |
|---|---|---|---|
| Sodium | 132 | 0.042-0.083 | 0.63-1.79 |
| Calcium | 1.75 | 3.1-6.3 | 47.4-135 |
| Potassium | 2 | 2.75-5.5 | 41.5-118 |
| Magnesium | 0.25 | 22-44 | 332-944 |
| Chloride | 96 | 0.057-0.11 | 0.86-2.46 |

| Buffer (L) | mmole | Molar Ratio Range (dextrose to buffer) HD | Molar Ratio Range (dextrose to ion) PD |
|---|---|---|---|
| HCO3 | 20-50 | 0.11-0.55 | 1.66-11.8 |
| Acetate | 2.0-5.0 | 1.1-5.5 | 16.6-118 |
| Lactate | 40 | 0.14-0.28 | 2.1-5.9 |

| Amino acid (/L) | micromole | Molar Ratio Range (dextrose to amino acid) HD | Molar Ratio Range (dextrose to ion) PD |
|---|---|---|---|
| Alanine | 347.5 | 16-32 | 239-679 |
| Arginine | 60.25 | 91-183 | 1,378-3,917 |
| Asparagine | 57.5 | 96-191 | 1,443-4,104 |
| Aspartic acid | 8 | 688-1,375 | 10,375-29,500 |
| Beta-alanine | 19.5 | 282-564 | 4,256-12,103 |
| Cystine | 40.25 | 137-273 | 2,062-5,863 |
| Glutamic acid | 72 | 76-153 | 1,153-3,278 |
| Glutamine | 547.5 | 10-20 | 152-431 |
| Glycine | 212.5 | 26-52 | 391-1,111 |
| Histidine | 83.5 | 66-132 | 994-2,826 |
| Isoleucine | 79.75 | 69-138 | 1,041-2,959 |
| Leucine | 119 | 46-92 | 697-1,983 |
| Lysine | 195 | 28-56 | 426-1,210 |
| Methionine | 22.25 | 247-494 | 3,730-10,607 |
| Phenylalanine | 55.25 | 100-199 | 1,502-4,271 |
| Proline | 222.5 | 25-49 | 373-1,061 |

TABLE 1-continued

Dry Composition, Concentrated Composition and Liquid Composition Components

| | | | |
|---|---|---|---|
| Serine | 109.75 | 50-100 | 756-2,150 |
| Threonine | 137.25 | 40-80 | 605-1,719 |
| Tryptophan | 66.5 | 83-165 | 1,248-3,549 |
| Tyrosine | 63.75 | 86-173 | 1,302-3,702 |
| Valine | 242.5 | 23-45 | 342-973 |

| Vitamin (/L) | micromole | Molar Ratio Range (dextrose to vitamin) HD | Molar Ratio Range (dextrose to ion) PD |
|---|---|---|---|
| Vitamin A | 0.052 | 105,769-211,538 | 1,596,154-4,538,462 |
| Vitamin C | 7.57 | 727-1,453 | 10,964-31,176 |
| Vitamin B6 | 1.48 | 3,716-7,432 | 56,081-159,459 |
| Vitamin E | 0.90 | 6,111-12,222 | 92,222-262,222 |
| Folate (Vit B9) | 15.18 | 362-725 | 5,468-15,547 |
| Vitamin D | 0.0044 | 1,250,000-2,500,000 | 18,863,636-53,636,364 |
| Vitamin K | 0.0038 | 1,447,368-2,894,737 | 21,842,105-62,105,263 |
| Thiamine | 0.075 | 73,333-146,667 | 1,106,667-3,146,667 |
| Riboflavin | 0.053 | 103,774-207,547 | 1,566,038-4,452,830 |
| Niacin | 4.71 | 1,168-2,335 | 17,622-50,106 |
| Vitamin B12 | 0.000030 | 183,333,333-366,666,667 | 2,766,666,667-7,866,666,667 |
| Pantothenic acid | 0.38 | 14,474-28,947 | 218,421-621,053 |
| Biotin | 0.0021 | 2,619,048-5,238,095 | 39,523,810-112,380,952 |
| Choline | 79.99 | 69-138 | 1,038-2,950 |
| | | 105,769-211,538 | 1,596,154-4,538,462 |
| Mineral (/L) | | | |
| Iron | 2.3279 | 2-4,725 | 35,654-101,379 |
| Copper | 0.2360 | 23,305-46,610 | 351,695-1,000,000 |
| Chromium | 0.0096 | 572,917-1,145,833 | 8,645,833-24,583,333 |
| Fluoride | 3.1582 | 1,741-3,483 | 26,281-74,726 |
| Iodine | 0.0197 | 279,188-558,376 | 4,213,198-11,979,695 |
| Manganese | 0.5461 | 10,071-20,143 | 151,987-432,155 |
| Molybdenum | 0.0078 | 705,128-1,410,256 | 10,641,026-30,256,410 |
| Selenium | 0.0117 | 470,085-940,171 | 7,094,017-20,170,940 |
| Zinc | 2.6002 | 2,115-4,230 | 31,921-90,762 |

The dry composition may also be available in a concentrated form. In some aspects, the present disclosure provides a concentrated composition comprising a dry composition described herein, and an initial aqueous solution. The concentrated composition described herein may be advantageous since it may minimize storage space, weight, and transport of water and may also increase the stability and thereby also the shelf-life of the dialysis components. The concentrated composition may be stable for long term storage and transportation. The concentrated composition may be available in a container, in which additional aqueous solution may be added to the container to bring the solution to volume, at which point, the concentrated composition may be ready to use by the subject. The container may have the capacity to hold approximately 1, 2, 2.5, 4, or 10 liter of total aqueous solution. The additional aqueous solution may be added to the concentrated composition prior to administration to a subject for dialysis.

Food Composition

In some aspects, the present disclosure provides a food composition comprising: (a) a cysteine devoid protein source; (b) at least one essential amino acid; and (c) at least one nonessential amino acid selected from a group consisting of alanine, asparagine, aspartate, glutamic acid, glycine, and proline, wherein each nonessential amino acid is 0-1% wt/wt of protein of the food composition, wherein the food composition comprises 0-1% wt/wt of cysteine and/or cystine of protein of the food composition, and wherein the food composition comprises at least 6% wt/wt of protein.

In certain embodiments, the amount of each nonessential amino acid, selected from a group consisting of alanine, asparagine, aspartate, glutamic acid, glycine, and proline, is 0-2% wt/wt of the protein in the food composition. The amount of each nonessential amino acid may be approximately 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or 2.0% wt/wt of the protein. The amount of each nonessential amino acid may be 0-1% wt/wt of the protein in the food composition. In one embodiment, the amount of each nonessential amino acid is 0-0.1% wt/wt of the protein in the food composition. In some embodiments, the food composition comprises at least two of the nonessential amino acid selected from a group consisting of alanine, asparagine, aspartate, glutamic acid, glycine, and proline. The food composition may comprise at least three of the nonessential amino acid selected from a group consisting of alanine, asparagine, aspartate, glutamic acid, glycine, and proline. The food composition may comprise at least four of the nonessential amino acid selected from a group consisting of alanine, asparagine, aspartate, glutamic acid, glycine, and proline. The food composition may comprise at least five of the nonessential amino acid selected from a group consisting of alanine, asparagine, aspartate, glutamic acid, glycine, and proline. The food composition may comprise at least six of the nonessential amino acid selected from a group consisting of alanine, asparagine, aspartate, glutamic acid, glycine, and proline. In some embodiments, at least one of the nonessential amino acid is glycine. In some embodiments, at least one of the nonessential amino acid is proline.

In certain embodiments, the amount of the cysteine and/or cystine is 0-2% wt/wt of the protein in the food composition. The amount of the cysteine and/or cystine may be 0-1% wt/wt of the protein in the food composition, such as 0, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, or 1% wt/wt of the protein. In an exemplary embodiment, the amount of cysteine and/or cystine is 0-0.2% wt/wt of the protein in the food composition. In one embodiment, the amount of cysteine and/or cystine is approximately 0-0.1% wt/wt of the protein in the food composition. In another embodiment, the amount of cysteine and/or cysteine is 0-0.04% wt/wt of the food composition, such as approximately 0, 0.01, 0.02, 0.03, or 0.04% wt/wt of the food composition.

In some aspects, the present disclosure provides a food composition comprising: (a) a cysteine devoid protein source; (b) at least one essential amino acid; and (c) at least six nonessential amino acids selected from the group consisting of alanine, asparagine, aspartate, glutamic acid, glycine, proline, glutamine, serine, tyrosine, and cysteine, wherein each nonessential amino acid is 0-1% wt/wt of protein in the food composition, and wherein the food composition comprises at least 6% wt/wt of protein.

In some aspects, the present disclosure provides a food composition comprising: (a) at least one essential amino acid; and (b) glutamate, wherein the food composition is substantially free of nonessential amino acids other than glutamate. In some aspects, the present disclosure provides a food composition comprising: (a) at least one essential amino acid; (b) glutamate; and (c) arginine, wherein the food composition is substantially free of nonessential amino acids other than glutamate.

In certain embodiments, the amount of each nonessential amino acid selected from a group consisting of alanine, asparagine, aspartate, glutamic acid, glycine, proline, glutamine, serine, tyrosine, and cysteine is 0-2% wt/wt of the protein in the food composition. The amount of each nonessential amino acid may be approximately 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or 2.0% wt/wt of the protein. The amount of each nonessential amino acid may be 0-1% wt/wt of the protein in the food composition. In one embodiment, the amount of each nonessential amino acid is 0-0.1% wt/wt of the protein in the food composition.

In some embodiments, the food composition comprises at least seven of the nonessential amino acid selected from a group consisting of alanine, asparagine, aspartate, glutamic acid, glycine, proline, glutamine, serine, tyrosine, and cysteine. The food composition may comprise at least eight of the nonessential amino acid selected from a group consisting of alanine, asparagine, aspartate, glutamic acid, glycine, proline, glutamine, serine, tyrosine, and cysteine. The food composition may comprise at least nine of the nonessential amino acid selected from a group consisting of alanine, asparagine, aspartate, glutamic acid, glycine, proline, glutamine, serine, tyrosine, and cysteine. The food composition may comprise at least ten of the nonessential amino acid selected from a group consisting of alanine, asparagine, aspartate, glutamic acid, glycine, proline, glutamine, serine, tyrosine, and cysteine. The food composition may comprise at least six of the nonessential amino acids are selected from the group consisting of glycine, proline, glutamine, serine, tyrosine, and cysteine. In some embodiments, at least one of the nonessential amino acid is glycine. In some embodiments, at least one of the nonessential amino acid is proline. In an exemplary embodiment, at least one of the nonessential acids is cysteine. When the food composition comprises cysteine, the amount of cysteine and/or cystine is 0-2% wt/wt of protein in the food composition. The amount of the cysteine and/or cystine may be approximately 0-1% wt/wt of the protein in the food composition, such as approximately 0, 0.1, 0.2, 0.3, 0.4, 0.5, 0.6, 0.7, 0.8, 0.9, or 1% wt/wt of the protein. In an exemplary embodiment, the amount of cysteine and/or cystine is 0-0.2% wt/wt of the protein in the food composition. In one embodiment, the amount of cysteine and/or cystine is 0-0.1% wt/wt of the protein in the food composition. In another embodiment, the amount of cysteine and/or cysteine is 0-0.04% wt/wt of the food composition, such as approximately 0, 0.01, 0.02, 0.03, or 0.04% wt/wt of the food composition. In an exemplary embodiment, the food composition is substantially free of cysteine and/or cystine. The food composition may be free of cysteine and/or cystine.

Any food composition as described herein, in certain embodiments, the amount of the cysteine devoid protein source is at least 1% wt/wt of the food composition. The cysteine devoid protein source may be gelatin. The amount of the a cysteine devoid protein source may be 0.1, 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, or 10.0% wt/wt of the food composition. In some embodiments, the amount of the cysteine devoid protein source is 1-5% of the food composition.

Any food composition described herein, in certain embodiments, the amount of protein is at least approximately 5% of the total weight of the food composition. The amount of protein in the food composition may be approximately 5, 6, 7, 8, 9, 10, 11, 12, 13, 14, 15, 16, 17, 18, 19, 20, 21, 22, 23, 24 or 25% of the total weight of the food composition. In one embodiment, the amount of protein is approximately 6% of the total weight of the food composition. In another embodiment, the amount of protein is approximately 16% of the total weight of the food composition.

Any food composition as described herein, in certain embodiments, the essential amino acid is selected from a group consisting of arginine, histidine, isoleucine, leucine, lysine, methionine, phenylalanine, threonine, tryptophan, and valine. In an exemplary embodiment, the essential amino acid is methionine. In an exemplary embodiment, the essential amino acid is arginine. The essential amino acid may be approximately 1, 2, 3, 4, 5, 6, 7, 8, 9, 10, 11, 12, 13, 14, 15, 20, 25, 30, 35, 40, 45, 50, 55, 60, 65, 70, or 75% wt/wt of the food composition. In some embodiments, the essential amino acid is at least approximately 2% wt/wt of the food composition. The amount of the essential amino acid may be 2-30% wt/wt of the food composition. In an exemplary embodiment, the amount of the essential amino acid is approximately 8% wt/wt of the food composition.

In one embodiment, the food composition comprises at least two essential amino acids. The food composition may comprise at least three essential amino acids. The food composition may comprise at least four essential amino acids. The food composition may comprise at least five essential amino acids. The food composition may comprise at least six essential amino acids. The food composition may comprise at least seven essential amino acids. The food composition may comprise at least eight essential amino acids. The food composition may comprise at least nine essential amino acids. The food composition may comprise at least ten essential amino acids.

Any food composition described herein may further comprise at least one vitamin. The vitamin may be selected from a group consisting of vitamin A, vitamin B, vitamin C, vitamin D, vitamin E, vitamin K, and choline. In an exemplary embodiment, the vitamin is vitamin C. In one embodiment, the food composition comprises at least approximately 10 mg of vitamin C per kg of the food composition. The food composition may comprise approximately 10, 15, 20, 25, 30, 40, 45, 50, 55, or 60 mg of vitamin C per kg of the food composition. In an exemplary embodiment, the food composition comprises approximately 40 mg of vitamin C per kg of the food composition.

In certain embodiments, any food compositions described herein further comprises an essential fatty acid, such as omega-6 and omega-3 fatty acids. In one embodiment, the essential fatty acid is an omega-3 fatty acid. The amount of essential fatty acid may be approximately 100, 150, 200, 250, 300, 350, 400, 450, 500, 750, 1000, 1100, 1200, 1300, 1400, 1500, 1600, 1700, 1800, 1900 or 2000 mg per liter. In some embodiments, the amount of essential amino acids is 1200-1600 mg per liter. In some embodiments, the amount of essential amino acids is 100-200 mg per liter.

In certain embodiments, any food compositions described herein further comprises at least one mineral. The mineral may be selected from a group consisting of iron, copper, chromium, fluoride, iodine, manganese, molybdenum, selenium, and zinc. In an embodiment, the food composition comprises at least approximately 1% w/w of mineral, such as 1, 2, 3, 4, or 5% w/w of mineral in the food composition. The amount of at least one of the mineral may be 0.05 mg-20 g per kg of the food composition, such as approximately 0.1, 1, 10, 50, 100, 500, 1,000, 5,000, 10,000 or 20,000 mg of mineral per kg of the food composition.

Any food compositions described herein further comprise at least one ion. In certain embodiments, the amount of at least one ion is at least 0.1% w/w, such as 0.1, 0.5, 1.0, 1.5, 2.0, 2.5, 3.0% w/w of ion in the food composition. The amount of at least one ion may be 0.05-20 g per kg food, such as approximately 0.05, 0.1, 1, 5, 10, 15, or 20 g of ion per kg of the food composition.

Any food compositions described herein further comprise glutamate. In some embodiments, the food composition comprises at least, approximately, or no more than 0.1 mg of glutamate, such as approximately 0.1, 1, 5, 10, 15, 20, 25, 30, 35, 40, 45 or 50 mg. The amount of glutamate may be 0.1-50 mg, 5-25 mg, or 25-45 mg.

In some embodiments, any of the food compositions described herein comprise at least approximately 10% wt/wt of amino acids, such as 10, 11, 12, 13, 14, 15, 16, 17, 18, 19, or 20% w/w or amino acids. In some embodiments, the food composition comprises approximately 14% wt/wt of amino acids. In some embodiments, the food composition comprises approximately 17% wt/wt of amino acids. In some embodiments, the food composition comprises 10-20% w/w of total amino acids. The food composition may comprise 14-17% w/w of total amino acids.

Any food composition as described herein, in certain embodiments, the food composition further comprises a pharmaceutically active agent. The amount of pharmaceutical agent, or any other component used in the food compositions described herein can be used in an amount that is therapeutically effective. The therapeutic amount can be assessed for individual subjects, or for groups of subjects. The group of subjects can be all potential subjects, or subjects having a particular characteristic such as age, weight, race, gender, or physical activity level. The pharmaceutically active agent may include anti-cancer therapeutics, such as mesna. The pharmaceutically active agent provided to the subject may be approximately 5, 10, 50, 100, 500, 1000, 1200, 1500, 2000, 2500, or 3000 mg. In some embodiments, the pharmaceutically active agent provided to the subject is 10-2000 mg. In some embodiments, the mesna is provided to the subject is 200-1200 mg. In some embodiments, the pharmaceutically active agent is an anti-obesity therapeutic.

Methods of Use

The invention provides for methods of treating (including preventing) cancer, metabolic diseases, such as obesity, and/or renal disease in subjects in need thereof. The method can include the reduction, depletion and/or supplementation of certain nutrients to the subject's diet. The method can include administering to the subject a food composition described herein that has no more than certain amounts of pre-selected nutrients. The nutrients that are reduced or depleted can be certain nutrients that are demanded at a higher level or degree by cancerous cells as compared to non-cancerous cells. The subject's diet can be controlled by administering to the subject a food composition wherein the subject does not eat any other foods or nutrients other than those that are part of the food composition, or permitted under the regimen. Therefore, the food composition may consist of all of the foods provided to the subject, and the food composition may have only certain amounts of pre-selected nutrients. The food composition can be designed such that the nutrients provided to or ingested by the subject are evaluated or determined on an hourly, daily, weekly or monthly basis. For any numbers provided herein that are described on a daily basis, the invention provides for proportionally scaled numbers for such amounts on an hourly, weekly or monthly basis. The food composition can be provided to the subject, alone or in combination with the dry composition, concentrated composition or liquid composition, until consistent and significant improvement is seen in the subject, and may be modified at any point of the treatment to fit the needs of the subject.

The methods described herein also include the reduction, depletion and/or supplementation of certain nutrients in the subject's system, such as blood levels, through dialysis. The present disclosure envisions methods of performing dialysis. Dialysis machines for performing dialysis, such as Freedom Cycler (Fresenius Medical Care), HomeChoice PRO™ (Baxter Healthcare Corporation), HomeChoice™ (Baxter Healthcare Corporation), Liberty® Cycler (Fresenius Medical Care), Newton™ IQ Cycler System (Fresenius Medical Care), 2008K@Home™ (Fresenius Medical Care), NxStage® System One™ with PureFlow™ SL (NxStage Medical, Inc.), Quanta SC+ (Quanta Dialysis Technologies) and the like are known in the art, and may be used to carry out the methods described herein. The methods can include administering to the subject a liquid composition, concentrated composition, or dry composition described herein that has no more than certain pre-selected nutrients, which can be used alone or in combination with a diet that administers a food composition. In a preferred embodiment, the methods comprise placing a subject in need thereof on a nutritional diet with any of the food compositions disclosed herein and on dialysis with a dialysate composition (liquid composition, dry composition, or concentrated composition). In some embodiments, the subject is placed on a nutritional diet before, during, and/or after dialysis treatment. The nutrients that are reduced or depleted can be certain nutrients that are demanded at a higher level or degree by cancerous cells as compared to non-cancerous cells. The levels of these nutrients can be controlled by administering to the subject a dry composition, concentrated composition, or liquid composition and periodically monitoring the subject. For example, the methods may involve administering the composition to draw waste, fluid, and/or certain nutrients, such as cysteine and/or cystine, from the subject's blood. The dry composition, concentrated composition, or liquid composition may consist of a substantial amount of nutrients necessary for the subject, such as one or more essential amino acids, arginine, and glutamate. The methods may also involve administering the composition to provide the subject with necessary nutrients. The dialysate composition may be in the subject body as long necessary for the composition to exchange waste, fluids, and/or nutrients with the body. The exchange (drain and refill) may be facilitated by the subject or with the assistance of a machine. In some embodiments, the exchange takes at least 15, 20, 25, 30, 35, 40, 45, 50, 55, or 60 minutes.

The dry composition, concentrated composition or liquid composition can be designed such that the nutrients provided to the subject are evaluated or determined on an hourly, daily, weekly or monthly basis. For any numbers provided herein that are described on a daily basis, the invention provides for proportionally scaled numbers for such amounts on an hourly, weekly or monthly basis. The dry composition, concentrated composition, or liquid composition, alone or in combination with a food composition, can be provided to the subject until consistent and significant improvement is seen in the subject, and may be modified at any point of the treatment to fit the needs of the subject.

In some embodiments, the subject undergoes peritoneal dialysis. Peritoneal dialysis may involve the insertion of a flexible tube, such as a catheter, into the subject. The catheter may go inside the subject's abdomen or chest to outside the subject's body through an incision in the subject's skin. The catheter can fill the abdomen with dialysate FIG. 14 illustrates an exemplary dialysis system.

In some embodiments, the subject undergoes hemodialysis.

Treating Cancer

The methods described herein may comprise providing a composition described herein. In some aspects, the present disclosure provides a method for treating cancer in a subject in need thereof, the method comprising administering to the subject any food composition described herein, and administering to the subject a liquid composition described herein, a dry composition described herein, or a concentrated composition described herein.

In some aspects, the present disclosure provides a method for treating cancer in a subject in need thereof, the method comprising administering to the subject a liquid composition described herein, a dry composition described herein, or a concentrated composition described herein.

In some aspects, the present disclosure provides a method for treating cancer in a subject in need thereof, the method comprising administering to the subject any food composition described herein.

In certain embodiments, treating cancer is characterized by a reduction in tumor size. The tumor size may be reduced by at least 10, 15, 20, 25, 30, 35, 40, 45, 50, 55, 60, 65, 70, 75, 80, 85, 90, 95, or 100% of the initial tumor size prior to treatment. The tumor may be reduced by at least 30%. The tumor may be reduced by at least 50%. The tumor may be reduced by at least 80%. The reduction of tumor size may be 10-100%. The reduction of tumor size may be 30-100%.

In certain embodiments, treating cancer is characterized by a reduction in circulated cancer cell counts. The circulated cancer cell count may be reduced by at least 10, 15, 20, 25, 30, 35, 40, 45, 50, 55, 60, 65, 70, 75, 80, 85, 90, 95, or 100% of the initial circulated cancer cell count prior to treatment. The circulated cancer cell count may be reduced by at least 30%. The circulated cancer cell count may be reduced by at least 50%. The circulated cancer cell count may be reduced by at least 80%. The reduction of circulated cancer cell count may be 10-100%. The reduction of circulated cancer cell count may be 30-100%.

The methods of the present disclosure include monitoring levels of cysteine and/or cystine in the subject's blood. Monitoring cysteine and/or cystine may be used to modify the existing treatment in order to reduce the levels of cysteine and/or cystine to therapeutic levels.

In certain embodiments, treating cancer is characterized by decreased levels of plasma cysteine. The levels of plasma cysteine may be reduced by at least 10, 15, 20, 25, 30, 35, 40, 45, 50, 55, 60, 65, 70, 75, 80, 85, 90, 95, or 100% of the initial levels of plasma cysteine prior to treatment. The levels of plasma cysteine may be reduced by at least 30%. The levels of plasma cysteine may be reduced by at least 50%. The levels of plasma cysteine may be reduced by at least 80%. The levels of plasma cysteine may be reduced by at least 90%. The levels of plasma cysteine may be reduced by at least 95%. The levels of plasma cysteine may be 30-100%.

Administering a composition described herein may result in a reduction of blood levels of cysteine and/or cystine. The composition may be administered in therapeutic amounts. Subsequent to the administration of a composition described herein, the level of cysteine in the subject's blood may be reduced to less than average levels of cysteine, such as less than approximately 10 μM of cysteine. In certain embodiments, the level of cysteine in the subject's blood is less than approximately 9 μM, 8 μM, 7 μM, 6 μM, 5 μM, 4 μM, 3 μM, 2 μM, or 1 μM. In an exemplary embodiment, the level of cysteine in the subject's blood is approximately less than 1 μM. Subsequent to the administration of a composition described herein, the level of cystine in the subject's blood may be reduced to less than average levels of cystine, such as less than approximately 40 μM of cystine. In certain embodiments, the level of cystine in the subject's blood may be reduced to less than approximately 39 μM, 38 μM, 37 μM, 36 μM, 35 μM, 34 μM, 33 μM, 32 μM, 31 μM, 30 μM, 29 μM, 28 μM, 27 μM, 26 μM, 25 μM, 24 μM, 23 μM, 22 μM, 21 μM, 20 μM, 19 μM, 18 μM, 17 μM, 16 μM, 15 μM, 14 μM, 13 μM, 12 μM, 11 μM, 10 μM, 9 μM, 8 μM, 7 μM, 6 μM, 5 μM, 4 μM, 3 μM, 2 μM, or 1 μM. In an exemplary embodiment, the level of cystine in the subject's blood is approximately less than 5 μM.

Reducing Tumor Size

In some aspects, the present disclosure provides a method for reducing tumor size and/or circulated cancer cell counts in a subject in need thereof, the method comprising administering to the subject any food composition described herein, and administering to the subject a liquid composition described herein, a dry composition described herein, or a concentrated composition described herein.

In some aspects, the present disclosure provides a method for reducing tumor size and/or circulated cancer cell counts in a subject in need thereof, the method comprising administering to the subject a liquid composition of claim 1, a dry composition described herein, or a concentrated composition described herein.

In some aspects, the present disclosure provides a method for reducing tumor size and/or circulated cancer cell counts in a subject in need thereof, the method comprising administering to the subject any food composition described herein.

Methods of the disclosure may result in suppressing tumor growth in a subject. In certain embodiments, the subject's tumor size does not increase by greater than 0-100%, such as approximately 0, 10, 20, 30, 40, 50, 60, 70, 80, 90 or 100%, as measured before and 6 weeks after the initial administration of any food composition described herein, and administering to the subject a liquid composition described herein, a dry composition described herein, or a concentrated composition described herein. The subject's tumor size may not increase by greater than approximately 100%, as measured before and 6 weeks after the initial administration of any food composition described herein, and administering to the subject a liquid composition described herein, a dry composition described herein, or a concentrated composition described herein. The subject's tumor size may not increase by greater than approximately 70%, as measured before and 6 weeks after the initial administration. The subject's tumor size may not increase by greater than approximately 60%, as measured before and 6 weeks after the initial administration. The subject's tumor size may not increase by greater than approximately 40%, as measured before and 6 weeks after the initial administration. The subject's tumor size may not increase by greater than approximately 20%, as measured before and 6 weeks after the initial administration. The subject's tumor size may not increase by greater than approximately 0%, as measured before and 6 weeks after the initial administration.

In certain embodiments, the subject's tumor size decreases by at least 10%, as measured before and 6 weeks after the initial administration of any food composition described herein, and administering to the subject a liquid composition described herein, a dry composition described herein, or a concentrated composition described herein. The subject's tumor size may decrease by at least 20%, as measured before and 6 weeks after the initial administration. The subject's tumor size may decrease by at least 30%, as measured before and 6 weeks after the initial administration. The subject's tumor size may decrease by at least 40%, as measured before and 6 weeks after the initial administration. The subject's tumor size may decrease by at least 50%, as measured before and 6 weeks after the initial administration.

Methods of the disclosure may result in a reduction in circulated cancer cell counts. The circulated cancer cell count may be reduced by at least 10, 15, 20, 25, 30, 35, 40, 45, 50, 55, 60, 65, 70, 75, 80, 85, 90, 95, or 100% of the initial circulated cancer cell count prior to treatment. The circulated cancer cell count may be reduced by at least 30%. The circulated cancer cell count may be reduced by at least 50%. The circulated cancer cell count may be reduced by at least 80%. The reduction of circulated cancer cell count may be 10-100%. The reduction of circulated cancer cell count may be 30-100%.

Treating Obesity

In some aspects, the present disclosure provides a method for treating obesity in a subject in need thereof, the method comprising administering to the subject any food composition described herein.

Treating obesity may characterized by weight loss in a subject. The subject may experience of at least or approximately 5, 10, 15, 20, 25, 30, 35, 40, 45 or 50% weight loss from the start of the nutritional diet with the food compositions disclosed herein. In certain embodiments, the subject's weight loss is greater than 5%, as measured before and 6 weeks after commencement of the controlled diet. A controlled diet comprises administering a food composition described herein to a subject in need thereof. The subject's weight loss may be greater than 10%, as measured before and 6 weeks after commencement of the controlled diet. The subject's weight loss may be greater than 15%, as measured before and 6 weeks after commencement of the controlled diet. The subject's weight loss may be greater than 20%, as measured before and 6 weeks after commencement of the controlled diet. The subject's weight loss may be greater than 25%, as measured before and 6 weeks after commencement of the controlled diet. The subject's weight loss may be greater than 30%, as measured before and 6 weeks after commencement of the controlled diet.

Treating Renal Disease

In some aspects, the present disclosure provides a method for treating renal disease in a subject in need thereof, the method comprising administering to the subject a liquid composition described herein, a dry composition described herein, or a concentrated composition. The methods of the present disclosure may provide or deplete certain nutrients to the subject. The subject may be experiencing malnutrition, nutrition deficiency or other side effects from dialysis, and administration of a liquid composition, dry composition, or concentrated composition may prevent, alleviate, reduce, or eliminate such side effects. Other side effects may include, but are not limited to, low blood pressure, nausea, vomiting, dry and itchy skin, restless leg syndrome, muscle cramping, or combinations thereof. For the methods described herein administering a liquid composition or dry composition, in certain embodiments, the methods further comprise utilizing a membrane. The membrane may comprise modified cellulose diacetate or polysulfone. In an exemplary embodiment, the membrane is a low-flux membrane that permits small molecule exchange. In some embodiments, the low-flux membrane comprises a plurality of pores, in which the plurality of pores comprises a first end and a second end. In some embodiments, the low-flux membrane comprises a plurality of pores. The plurality of pores may have an average pore diameter of approximately 1.8 nm. In some embodiments, the low-flux membrane permits approximately 50% or higher of a molecule weighing approximately 500 Daltons or less to move through the plurality of pores, from the first end to the second end. The low-flux membrane may permit approximately 75% or higher of a molecule weighing approximately 500 Daltons or less to move through the plurality of pores, from the first end to the second end. In some embodiments, the low-flux membrane permits approximately 90% or higher of a molecule weighing approximately 500 Daltons or less to move through the plurality of pores, from the first end to the second end. The low-flux membrane may permit approximately 95% or higher of a molecule weighing approximately 500 Daltons or less to move through the plurality of pores, from the first end to the second end. In some embodiments, approximately 20% of a molecule of at least 1000 Daltons passes through the plurality of pores, from the first end to the second end. Approximately 10% of a molecule of at least 1000 Daltons may pass from the first side to the second side. Approximately 1% of a molecule of at least 1000 Daltons may pass from the first side to the second side.

For any method described herein, the method can further comprise administering a pharmaceutically active agent. The pharmaceutically active agent may be an anti-cancer therapeutic. Examples of anti-cancer drugs include Herceptin®, Avastin®, Erbitux®, Rituxan®, Taxol®, Arimidex®, Taxotere®, ABVD, AVICINE, Abagovomab, Acridine carboxamide, Adecatumumab, 17-N-Allylamino-17-demethoxygeldanamycin, Alpharadin, Alvocidib, 3-Aminopyridine-2-carboxaldehyde thiosemicarbazone, Amonafide, Anthracenedione, Anti-CD22 immunotoxins, Antineoplastic, Antitumorigenic herbs, Apaziquone, Atiprimod, Azathioprine, Belotecan, Bendamustine, BMW 2992, Biricodar, Brostallicin, Bryostatin, Buthionine sulfoximine, CBV (chemotherapy), Calyculin, cell-cycle nonspecific antineoplastic agents, Dichloroacetic acid, Discodermolide, Elsamitrucin, Enocitabine, Epothilone, Eribulin, Everolimus, Exatecan, Exisulind, Ferruginol, Forodesine, Fosfestrol, ICE chemotherapy regimen, IT-101, Imexon, Imiquimod, Indolocarbazole, Irofulven, Laniquidar, Larotaxel, Lenalidomide, Lucanthone, Lurtotecan, Mafosfamide, Mitozolomide, Nafoxidine, Nedaplatin, Olaparib, Ortataxel, PAC-1, Pawpaw, Pixantrone, Proteasome inhibitor, Rebeccamycin, Resiquimod, Rubitecan, SN-38, Salinosporamide A, Sapacitabine, Stanford V, Swainsonine, Talaporfin, Tariquidar, Tegafur-uracil, Temodar, Tesetaxel, Triplatin tetranitrate, Tris(2-chloroethyl)amine, Troxacitabine, Uramustine, Vadimezan, Vinflunine, ZD6126 or Zosuquidar. The pharmaceutically active agent may be an anti-obesity therapeutic. Examples of anti-obesity therapeutic agents include lipase inhibitors (such as Orlistat), dopaminergic, noradrenergic, and serotoninergic compounds, cannabinoid receptor antagonists (such as rimonabant), exenatide, pramlintide, and CNS agents (such as topimerate). These examples are provided for discussion purposes only, and are intended to demonstrate the broad scope of applicability of the invention to a wide variety of drugs. It is not meant to limit the scope of the invention in any way.

In one embodiment, the pharmaceutically active agent is provided in a subtherapeutic amount. The amount of pharmaceutical agent, or any other component used in a combination composition described herein, can be used in an amount that is subtherapeutic. In some embodiments, using sub-therapeutic amounts of an agent or component can reduce the side effects of the agent. Use of subtherapeutic amounts can still be effective, particularly when used in synergy with other agents or components. A subtherapeutic amount of the agent or component can be such that it is an amount below which would be considered therapeutic. For example, FDA guidelines can suggest a specified level of dosing to treat a particular condition, and a subtherapeutic amount would be any level that is below the FDA suggested dosing level. The subtherapeutic amount can be about 1, 5, 10, 15, 20, 25, 30, 35, 50, 75, 90, or 95% less than the amount that is considered to be a therapeutic amount. The therapeutic amount can be assessed for individual subjects, or for groups of subjects. The group of subjects can be all potential subjects, or subjects having a particular characteristic such as age, weight, race, gender, or physical activity level.

For any method described herein, in certain embodiments, the methods can further comprise administering a nutritional supplement. In some embodiments, the nutritional supplement comprises one or more nutrients, which may include vitamins, minerals, water, carbohydrates, fats, proteins, and combinations thereof. Nutritional supplements may be packaged as vitamins, minerals, herbs, meal supplements, sports nutrition products, natural food supplements, and fortified food products. The nutritional supplement may comprise at least one amino acid selected from a group consisting of arginine, histidine, isoleucine, lysine, methionine, phenylalanine, threonine, tryptophan, and valine. The nutritional supplement may provide the subject with nutrients at levels in accordance with the Dietary Reference Intake (DRI), the Reference Daily Intake (RDI), the World Health Organization (WHO) guidelines, Recommended Dietary Allowances (RDAs), Adequate Intakes (Ais), and/or Daily Value (DV). The required levels of nutrients may be the same or different for adults, children, men, and women. In certain embodiments, the nutritional supplement comprises one or more nutrients selected from a group consisting of vitamin A, thiamine, riboflavin, niacin, pantothenic acid, vitamin B6, biotin, folate, cyanocobalamin, vitamin C, vitamin D, vitamin E, vitamin K, and choline. In certain embodiments, the nutritional supplement comprises one or more nutrients selected from a group consisting of calcium, chloride, chromium, copper, fluoride, iodine, iron, magnesium, manganese, molybdenum, phosphorus, potassium, selenium, sodium and zinc. In certain embodiments, the nutritional supplement comprises one or more nutrients selected from a group consisting of water, carbohydrates, protein, fiber, fat, cholesterol, and fatty acids.

Dosing, Treatment Regimen, and Administration

Dialysis Only

The present disclosure provides methods of providing dialysis therapies to subjects in need thereof. For the methods described herein administering a liquid composition, dry composition or concentrated composition described herein, the liquid composition, dry composition, or concentrated composition may be administered via traditional dialysis methods. For example, the compositions may be administered by hemodialysis, peritoneal dialysis, hemofiltration, hemodiafiltration, and intestinal dialysis. In an exemplary embodiment, the compositions are administered by hemodialysis or peritoneal dialysis (such as continuous ambulatory PD (CAPD) and continuous cycler-assisted PD (CCPD). The dialysis treatment may be used in combination with other conventional methods for treating cancer, obesity and renal disease, such as surgery, radiation therapy, immunotherapy, anti-cancer therapeutics, anti-obesity therapeutics, or renal disease therapeutics.

For the methods described herein administering a liquid composition, dry composition, or concentrated composition described herein, in certain embodiments, the composition is administered to the subject at least once a week. The composition may be administered to the subject at least three times a week. The composition may be administered to the subject at least five times a week. In some embodiments, the composition is administered to the subject over the course of at least one week. The composition may be administered to the subject over the course of at least four weeks. The composition may be administered to the subject over the course of at least 2 months. The composition may be administered to the subject over the course of at least 3 months.

In some embodiments, the dialysis may be provided to a subject in need thereof in a dialysis center, a hospital, a clinic, health care facility, at home, or any place that is clean and dry.

Diet Only

For the methods described herein any food composition described herein may be administered multiple times a week, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more times a week. In certain embodiments, the food composition is administered to the subject at least once a week. The food composition may be administered to the subject at least three times a week. The food composition may be administered to the subject at least five times a week. In an embodiment, the food composition may be administered to the subject at least twenty-one times a week. In some embodiments, the food composition may be administered to the subject over the course of at least one week. The food composition may be administered to the subject over the course of at least four weeks. The food composition may be administered to the subject over the course of at least 2 months. The food composition may be administered to the subject over the course of at least 3 months.

Dialysis and Diet

In any of the methods described herein, in certain embodiments, the liquid composition, the dry composition or concentrated composition described herein is administered to the subject sequentially with any food composition described herein. In another embodiment, the liquid composition, the dry composition or concentrated composition described herein is administered to the subject simultaneously with any food composition described herein. In some embodiments, the food composition, and the liquid composition, dry composition or concentrated composition are administered to the subject at least once a week. The food composition, and the liquid composition, dry composition or concentrated composition may be administered to the subject at least three times a week. The food composition, and the liquid composition, dry composition or concentrated composition may be administered to the subject over the course of at least one week. The food composition, and the liquid composition, dry composition or concentrated composition may be administered to the subject over the course of at least four weeks.

Pharmaceutical Compositions and Formulations

Diet

Any food composition described herein may have a pre-selected caloric value. For example the food composition may comprise at least 10, 20, 50, 100, 200, 300, 400, 500, 600, 700, 800, 900, 1000, or 1500 kcal. The food composition may have a caloric value 0-100, 0-200, 200-400, 400-600, 600-800, 800-1000 or 500-1000 kcal. The food composition may have a mass that is at least 5, 10, 50, 100, 200, 300, 400, 500, 600, 700, or 1000 grams. The food composition may have a mass that is 0-100, 100-200, 200-400, 400-600, or 100-500 grams.

Any food composition as described herein may be sold to a subject in a packaged container. In certain embodiments, the food composition is packaged as a solid food, semi-solid food, or beverage. The food composition may be a concoction of nutrient ingredients, an instant quick meal mix, a microwaveable frozen paste, a bake- or roast-ready dough, or a customizable mixture of several nutrient modules with flavor varieties. In some embodiments, the food compositions may be cooked, partially cooked, or uncooked. For example, the food composition may be baby formula, a soft drink, pulp-free juice, a nutritional shake, a granola bar, a dessert, or candy. In some embodiments, the food composition is fortified with vitamins, minerals, herbs, nutrients, and combinations thereof. The food composition may be packaged as a food product selected from a group consisting of a snack bar, cereal product, bakery product, and dairy product. For example, the food composition may be baby formula or baby food. The food composition may be a soft drink. The food composition may be a nutritional shake or nutritional snack, such as a granola bar. The food composition may be meal replacement drink or snack. The food composition may have a palatability enhancer. The palatability enhancer may be can be MSG, or some other form of glutamate, salt.

In some embodiments, the food composition is a pet food. The pet food can be a wet or dry pet food. The pet food can be formed as a kibble which may be coated. The coating may be a polymer coating that is applied to the kibble after the kibble is formed.

In any of the methods administering any food composition described herein, in certain embodiments, further comprises additives, fillers or excipients. Additives, fillers and excipients may be added to beverages, solid food, semi-solid food, and other consumable substances in the any food composition. Additives, fillers, and excipients may include acidulents, acidity regulators, anticaking agents, antifoaming and foaming agents, antioxidants, bulking agents, food coloring, color retention agents, emulsifiers, flavors, flavor enhancers, four treatment agents, glazing agents, humectants, tracer gas, preservatives, stabilizers, sweeteners, and thickeners. In an exemplary embodiment, additives, fillers and excipients include one or more corn starch, maltodextrin 10, cellulose, mineral mix S10001, sodium bicarbonate, vitamin mix V10001, and choline bitrartrate. In some embodiments, the additives are food coloring. Food coloring may include FD&C blue #1, FD&C blue #2, FD&C citrus red #2, FD&C green #3, FD&C red #3, FD&C red #40, FD&C yellow #5, and FD&C yellow #6. In an exemplary embodiment, dyes in the food composition include one or more FD&C red #40, FD&C blue #1, and FD&C yellow dye #5.

In any of the methods administering any food composition described herein, in certain embodiments, the methods further comprises preservatives. Preservatives may be added to beverages, solid food, semi-solid food, and other consumable substances in the food composition. Preservatives may include natural food preservatives, chemical food preservatives, or artificial preservatives. For example, preservatives may include acetic acid, ascorbic acid, calcium ascorbate, erythrobic acid, isoascorbic acid, potassium nitrate, potassium nitrite, sodium ascorbate, sodium erythorbate, sodium isoascorbate, sodium nitrate, sodium nitrite, wood smoke, benzoic acid, calcium sorbate, *carnobacterium divergens* M35, *Carnobacterium maltaromaticum* CB1, ethyl lauroyl arginate, 4-hexylresorcinol, *leuconostoc carnosum* 4010, methyl-p-hydroxy benzoate, methyl paraben, potassium acetate, potassium benzoate, potassium bisulphite, potassium diacetate, potassium lactate, potassium metabisulphite, potassium sorbate, propyl-p-hydroxy benzoate, propyl paraben, sodium acetate, sodium benzoate, sodium bisulphite, sodium diacetate, sodium lactate, sodium metabisulphite, sodium salt of methyl-p-hydroxy benzoic acid, sodium salt of propyl-p-hydroxy benzoic acid, sodium sorbate, sodium sulphite, sodium dithionite, sorbic acid, *sulphurous* acid, calcium propionate, calcium sorbate, dimethyl dicarbonate, natamycin, potassium sorbate, propionic acid, sodium diacetate, sodium proprionate, socium sorbate, sorbic acid, ascorbic acid, ascorbyl palmitate, ascorbyl stearate, butylate hydroxyanisole, butylated hydroxytoluene, citric acid esters of mono- and di-glycerides, gum guaiacum, lecithin, lecithin citrate, monoglyceride citrate, monoisopropyl citrate, propyl gallate, sodium metabisulphite, tartaric acid, tertiary butyl hydroquinone, and tocopherols. In one embodiment, preservatives are selected from a group consisting of sulfites, vitamin E, vitamin C, and butylated hydroxytoluene. In certain embodiments, preservation of beverages, solid food, semi-solid food, and other consumable substances may be accomplished through physical preservation, such as through freezing, boiling, smoking, and dehydration.

Dialysis

In certain embodiments, the liquid composition is stored in a container. For example, the container may be a dialysis bag. In one embodiment, the dialysis bag is intended for single-use. The container may hold about 1500 to 5000 mL of liquid composition. In one embodiment, approximately 2000 mL of liquid composition is a single unit. In another embodiment, approximately 2500 mL of liquid composition is a single unit.

In certain embodiments, the dry composition or concentrated composition is stored in a container. For example, the container may be a dialysis bag. In one embodiment, the dialysis bag is intended for single-use. In some embodiments, the dry composition or concentrated composition further comprises an aqueous solution in the container, thereby producing a mixture. The aqueous solution may be a sterile or nonsterile fluid. In one embodiment, the container comprises approximately 2000 mL of aqueous solution. In another embodiment, the container comprises approximately 2500 mL of aqueous solution. In certain embodiments, the mixture has a pH of approximately 4.0-6.5. In certain embodiments, the mixture has an osmolarity of approximately 300-720 mOsmol/L.

Applications

Cancer

In any of the methods described herein for treating cancer, in certain embodiments, the present disclosure provides a method for treating cancer and preventing cancer with the food compositions and/or dialysis compositions disclosed herein. In some embodiments, the method relates to the treatment of cancer such as acute myeloid leukemia, cancer in adolescents, adrenocortical carcinoma childhood, AIDS-related cancers (e.g., Lymphoma and Kaposi's Sarcoma), anal cancer, appendix cancer, astrocytomas, atypical teratoid, basal cell carcinoma, bile duct cancer, bladder cancer, bone cancer, brain stem glioma, brain tumor, breast cancer, bronchial tumors, burkitt lymphoma, carcinoid tumor, atypical teratoid, embryonal tumors, germ cell tumor, primary lymphoma, cervical cancer, childhood cancers, chordoma, cardiac tumors, chronic lymphocytic leukemia (CLL), chronic myelogenous leukemia (CML), chronic myleoproliferative disorders, colon cancer, colorectal cancer, craniopharyngioma, cutaneous T-cell lymphoma, extrahepatic ductal carcinoma in situ (DCIS), embryonal tumors, CNS cancer, endometrial cancer, ependymoma, esophageal cancer, esthesioneuroblastoma, ewing sarcoma, extracranial germ cell tumor, extragonadal germ cell tumor, eye cancer, fibrous histiocytoma of bone, gall bladder cancer, gastric cancer, gastrointestinal carcinoid tumor, gastrointestinal stromal tumors (GIST), germ cell tumor, gestational trophoblastic tumor, hairy cell leukemia, head and neck cancer, heart cancer, liver cancer, hodgkin lymphoma, hypopharyngeal cancer, intraocular melanoma, islet cell tumors, pancreatic neuroendocrine tumors, kidney cancer, laryngeal cancer, lip and oral cavity cancer, liver cancer, lobular carcinoma in situ (LCIS), lung cancer, lymphoma, metastatic squamous neck cancer with occult primary, midline tract carcinoma, mouth cancer multiple endocrine neoplasia syndromes, multiple myeloma/plasma cell neoplasm, mycosis fungoides, myelodysplastic syndromes, myelodysplastic/myeloproliferative neoplasms, multiple myeloma, merkel cell carcinoma, malignant mesothelioma, malignant fibrous histiocytoma of bone and osteosarcoma, nasal cavity and paranasal sinus cancer, nasopharyngeal cancer, neuroblastoma, non-hodgkin lymphoma, non-small cell lung cancer (NSCLC), oral cancer, lip and oral cavity cancer, oropharyngeal cancer, ovarian cancer, pancreatic cancer, papillomatosis, paraganglioma, paranasal sinus and nasal cavity cancer, parathyroid cancer, penile cancer, pharyngeal cancer, pleuropulmonary blastoma, primary central nervous system (CNS) lymphoma, prostate cancer, rectal cancer, transitional cell cancer, retinoblastoma, rhabdomyosarcoma, salivary gland cancer, skin cancer, stomach (gastric) cancer, small cell lung cancer, small intestine cancer, soft tissue sarcoma, T-Cell lymphoma, testicular cancer, throat cancer, thymoma and thymic carcinoma, thyroid cancer, transitional cell cancer of the renal pelvis and ureter, trophoblastic tumor, unusual cancers of childhood, urethral cancer, uterine sarcoma, vaginal cancer, vulvar cancer, or Viral-Induced cancer. In some embodiments, the cancer is selected from a group consisting of leukemia, hematologic malignancy, solid tumor cancer, prostate cancer, breast cancer, liver cancer, or brain tumor. In an exemplary embodiment, the cancer is selected from a group consisting of lung cancer, liver cancer, breast cancer, prostate cancer, colon cancer, lymphoma, and leukemia.

In some aspects, the present disclosure provides a method of treating cancer in a subject that has been placed on a low-cysteine diet, comprising: placing the subject under dialysis, wherein the dialysis reduces or depletes cysteine from the subject's body.

In some aspects, the present disclosure provides a method of depleting cysteine in a subject that has been placed on a low-cysteine diet, comprising: placing the subject under dialysis, wherein the dialysis reduces or depletes cysteine from the subject's body.

In some aspects, the present disclosure provides a method of treating cancer in a subject that has been placed on a dialysis procedure to reduce cysteine in the blood, comprising: placing the subject on a low-cysteine diet.

In some embodiments, the dialysis comprises administering a liquid composition disclosed herein, a concentrated composition disclosed herein or a dry composition disclosed herein. In some embodiments, the low-cysteine diet is a food composition disclosed herein.

Obesity

In any of the methods described herein for treating obesity, in certain embodiments, the present disclosure provides a method for treating obesity and preventing obesity. In some embodiments, the method relates to the treatment or prevention of disorders that may result in obesity or be the cause of obesity such as overeating and bulimia, polycystic ovarian disease, craniopharyngioma, the Prader-Willi Syndrome, Frohlich's syndrome, Type II diabetics, GH-deficient subjects, normal variant short stature, Turner's syndrome, and other pathological conditions showing reduced metabolic activity or a decrease in resting energy expenditure as a percentage of total fat-free mass, e.g., children with acute lymphoblastic leukemia. In some embodiments, the method relates to treating at least one obesity-related health condition, including, not limited to, cardiovascular diseases, type 2 diabetes, obstructive sleep apnea, cancer, osteoarthritis, and depression.

Renal Disease

In any of the methods described herein for treating renal disease, in certain embodiments, the present disclosure provides a method for treating renal disease and preventing renal disease. In exemplary embodiments, renal disease is chronic renal disease. In some embodiments, the method relates to treating a subject diagnosed with renal disorders as identified by medical history, physical findings and laboratory tests. For example, the subject may be diagnosed with acute or chronic renal failure, resulting from diabetes, ischemia, drug induced toxicity, post-transplantation rejection with or without the need for dialysis; glomerulonephritis; glomerulosclerosis; interstitial nephritis; and acute tubular necrosis. Subjects may have physical findings such as anuria, lethargy, coma and decreased general growth rate. Subject may have increased plasma levels of creatinine, urea and uric acid (BUN), proteinuria, decreased GFR, RPF and renal size as determined by urogram, altered acid/base balance and changes in urine specific gravity.

Subject

Cancer

In any of the methods described herein for treating cancer and/or reducing tumor size, in certain embodiments, the subject is a human. For example, the human subject may be an adult, a child, or an infant. In an exemplary embodiment, the human subject is a human adult. The human subject may be a human adult 18 years old or older. The human subject may be between the ages 18 and 90 years old. In a certain embodiment, the human subject is between 40 and 85 years old. In an exemplary embodiment, the human subject is between 65 and 80 years old.

In any of the methods described herein for treating cancer and/or reducing tumor size, in certain embodiments, the subject is an animal. The animal subject may be a domesticated animal, such as a dog or cat. The animal subject may be a mouse or rat. The animal subject may be a mouse or rat at least 7 weeks old. The animal subject may be a mouse or rat between 7 and 15 weeks old. The animal subject may be a mouse or rat between 10 and 11 weeks old.

Subjects that can be treated with a food composition, liquid composition, concentrated composition, and/or dry composition of the present disclosure include subjects that have been diagnosed as having acute myeloid leukemia, acute myeloid leukemia, cancer in adolescents, adrenocortical carcinoma childhood, AIDS-related cancers (e.g., Lymphoma and Kaposi's Sarcoma), anal cancer, appendix cancer, astrocytomas, atypical teratoid, basal cell carcinoma, bile duct cancer, bladder cancer, bone cancer, brain stem glioma, brain tumor, breast cancer, bronchial tumors, burkitt lymphoma, carcinoid tumor, atypical teratoid, embryonal tumors, germ cell tumor, primary lymphoma, cervical cancer, childhood cancers, chordoma, cardiac tumors, chronic lymphocytic leukemia (CLL), chronic myelogenous leukemia (CML), chronic myleoproliferative disorders colon cancer, colorectal cancer, craniopharyngioma, cutaneous T-cell lymphoma, extrahepatic ductal carcinoma in situ (DCIS), embryonal tumors, CNS cancer, endometrial cancer, ependymoma, esophageal cancer, esthesioneuroblastoma, ewing sarcoma, extracranial germ cell tumor, extragonadal germ cell tumor, eye cancer, fibrous histiocytoma of bone, gall bladder cancer, gastric cancer, gastrointestinal carcinoid tumor, gastrointestinal stromal tumors (GIST), germ cell tumor, gestational trophoblastic tumor, hairy cell leukemia, head and neck cancer, heart cancer, liver cancer, hodgkin lymphoma, hypopharyngeal cancer, intraocular melanoma, islet cell tumors, pancreatic neuroendocrine tumors, kidney cancer, laryngeal cancer, lip and oral cavity cancer, liver cancer, lobular carcinoma in situ (LCIS), lung cancer, lymphoma, metastatic squamous neck cancer with occult primary, midline tract carcinoma, mouth cancer multiple endocrine neoplasia syndromes, multiple myeloma/plasma cell neoplasm, mycosis fungoides, myelodysplastic syndromes, myelodysplastic/myeloproliferative neoplasms, multiple myeloma, merkel cell carcinoma, malignant mesothelioma, malignant fibrous histiocytoma of bone and osteosarcoma, nasal cavity and paranasal sinus cancer, nasopharyngeal cancer, neuroblastoma, non-hodgkin lymphoma, non-small cell lung cancer (NSCLC), oral cancer, lip and oral cavity cancer, oropharyngeal cancer, ovarian cancer, pancreatic cancer, papillomatosis, paraganglioma, paranasal sinus and nasal cavity cancer, parathyroid cancer, penile cancer, pharyngeal cancer, pleuropulmonary blastoma, primary central nervous system (CNS) lymphoma, prostate cancer, rectal cancer, transitional cell cancer, retinoblastoma, rhabdomyosarcoma, salivary gland cancer, skin cancer, stomach (gastric) cancer, small cell lung cancer, small intestine cancer, soft tissue sarcoma, T-Cell lymphoma, testicular cancer, throat cancer, thymoma and thymic carcinoma, thyroid cancer, transitional cell cancer of the renal pelvis and ureter, trophoblastic tumor, unusual cancers of childhood, urethral cancer, uterine sarcoma, vaginal cancer, vulvar cancer, Viral-Induced cancer, leukemia, hematologic malignancy, solid tumor cancer, prostate cancer, castration-resistant prostate cancer, breast cancer, Ewing's sarcoma, bone sarcoma, primary bone sarcoma, T-cell prolymphocyte leukemia, glioma, glioblastoma, hepatocellular carcinoma, liver cancer, or diabetes, related conditions, and combinations thereof. In some embodiments, the subjects treated with a food composition, liquid composition, and/or dry composition of the present disclosure include subjects that have been diagnosed as having a non-cancerous hyperproliferative disorder such as benign hyperplasia of the skin (e.g., psoriasis), restenosis, and prostate (e.g., benign prostatic hypertrophy (BPH).

In certain embodiments, the human subject has been diagnosed with leukemia, lung cancer, liver cancer, breast cancer, colon cancer, prostate cancer, stomach cancer, cervix uteri, esophagus, bladder, non-hodgkin lymphoma, and combinations thereof. In certain embodiments, the animal subject has been diagnosed with malignant lymphoma, skin cancer, mammary gland tumors, breast cancer, soft tissue sarcoma, bone cancer, and combinations thereof.

In certain embodiments, the subject has a genetic predisposition for cancer.

In certain embodiments, the subject has elevated cysteine biosynthetic gene expression levels.

Obesity

As used herein, the term "obesity" refers to a condition in which individuals are considered "overweight," or "obese." The term "obese" or "obesity" includes "extreme obesity," "severe obesity," and "super obesity."

In any of the methods described herein for treating obesity, in certain embodiments, the subject is a human. For example, the human subject may be an adult or a child. In certain embodiments, the human subject is a human child. For example, a human child may be between the ages of 2 and 5 years old, the ages of 6 and 11 years old, and the ages of 12 and 17 years old. In certain embodiments, the human subject is a human adult. The human subject may be a human adult 18 years old or older. The human subject may be 18-90 years old. In a certain embodiment, the human subject is 30-80 years old. In an exemplary embodiment, the human subject is 45-65 years old.

In certain embodiments, the subject is an animal. The animal subject may be a domesticated animal, such as a dog or cat. The animal subject may be a mouse or rat. The animal subject may be a mouse or rat at least 7 weeks old. The animal subject may be a mouse or rat that is 7-15 weeks old. The animal subject may be a mouse or rat that is 10-11 weeks old.

Subjects that can be treated with a food composition, liquid composition, concentrated composition, and/or dry composition of the present disclosure include subjects that have been diagnosed as being overweight or obese and/or having a body mass index (BMI) of at least 25 kg/m$^2$. Obesity in a subject can be assessed using a body mass index (BMI) measurement. A subject's BMI can be calculated by dividing the subject's body weight (in kg) by the square of the subject's height (m$^2$). A subject can be considered obese if the subject exhibits a BMI that is over 25 kg/m$^2$, over 26 kg/m$^2$, over 27 kg/m$^2$, over 28 kg/m$^2$, over 29 kg/m$^2$, over 30 kg/m$^2$, over 31 kg/m$^2$, over 32 kg/m$^2$, over 33 kg/m$^2$, over 34 kg/m$^2$, over 35 kg/m$^2$, over 36 kg/m$^2$, over 37 kg/m$^2$, over 38 kg/m$^2$, over 39 kg/m$^2$, over 40 kg/m$^2$, over 41 kg/m$^2$, over 42 kg/m$^2$, over 43 kg/m$^2$, over 44 kg/m$^2$, over 45 kg/m$^2$, over 46 kg/m$^2$, over 47 kg/m$^2$, over 48 kg/m$^2$, over 49 kg/m$^2$, or over 50 kg/m$^2$. The subject may be diagnosed with class I obesity, class II obesity, class III obesity, or an equivalent thereof. The subject may have a BMI of at least 30 kg/m$^2$, at least 35 kg/m$^2$, at least 40 kg/m², at least 45 kg/m² or at least 50 kg/m². The subject may have a BMI between 25 kg/m² and 50 kg/m². The subject may experience at least one obesity-related health condition, including, not limited to, cardiovascular diseases, type 2 diabetes, obstructive sleep apnea, cancer, osteoarthritis, and depression. A subject can also be considered to exhibit a propensity to develop NASH or hepatic steatosis if the subject exhibits abdominal obesity. Abdominal obesity can be assessed by measuring the circumference of the subject's waist. For example, if the subject is an adult male, the subject can be considered to exhibit abdominal obesity if the subject exhibits a waist circumference of 102 cm or greater. For other example, if the subject is an adult female, the subject can be considered to exhibit abdominal obesity if the subject exhibits a waist circumference of 88 cm or greater.

In certain embodiments, the subject habitually consumes an excessive amount of food, has a genetic predisposition for obesity, routinely lacks physical activity, has an adverse reaction to medication, has a mental disorder, has an endocrine disorder, and combinations thereof. In certain embodiments, the subject has a genetic predisposition for obesity. In certain embodiments, obesity in the subject is due to polymorphisms in one or more genes. In certain embodiments, the subject habitually consumes an excessive amount of food.

In certain embodiments, treating obesity is characterized by the subject losing at least 5, 10, 15, 20, 25, 30, 35, 40, 45, or 50% of the subject's initial body weight. Treating obesity may be characterized by the subject losing at least 10% of the subject's initial body weight. Treating obesity may be characterized by the subject losing at least 20% of the subject's initial body weight. Treating obesity may be characterized by the subject losing at least 30% of the subject's initial body weight.

Renal Disease

As used herein, the term "renal disease" includes, but is not limited to, kidney disease, nephropathy, nephritis, nephrosis, chronic kidney disease, chronic renal failure, acute renal disease and acute kidney injury.

In any of the methods described herein for treating renal disease, in certain embodiments, the subject is a human. For example, the human subject may be an adult or a child. In certain embodiments, the human subject is a human child. In certain embodiments, the human subject is a human adult. The human subject may be a human adult 18 years old or older. In certain embodiments, the human subject is at least 30, 35, 40, 45, 50, 55, 60, 65, 70, 75, or 80 years old. The human subject may be at least 60 years old. The human subject may be between the ages 18 and 90 years old. In an exemplary embodiment, the human subject is between 55 and 75 years old.

In certain embodiments, the subject is an animal. The animal subject may be a domesticated animal, such as a dog or cat. The animal subject may be a mouse or rat. The animal subject may be a mouse or rat at least 7 weeks old. The animal subject may be a mouse or rat between 7 and 15 weeks old. The animal subject may be a mouse or rat that is 10-11 weeks old.

Subjects that can be treated with a food composition, liquid composition, and/or dry composition of the present disclosure include subjects that have been diagnosed with renal disease and/or a related condition. In certain embodiments, the subject has been previously or concurrently diagnosed with high blood pressure and/or diabetes, has an adverse reaction to medication, has a genetic predisposition for renal disease, experiences blockage to the urinary system, experiences inflammation (such as glomerulonephritis), and/or experiences infections (such as pyelonephritis).

Facilities

In some aspects, the present disclosure provides a facility comprising a plurality of liquid compositions. In certain embodiments, the facility manufactures the liquid composition described herein or components thereof. In one embodiment, the facility is a pharmaceutical manufacturing site. In certain embodiments, the facility distributes the liquid composition described herein or components thereof. For example, the facility may be a distribution center. In certain embodiments, the facility administers the liquid composition described herein or components thereof. In one embodiment, the facility is a hospital, dialysis center, home or clinic. The facility may administer the liquid composition to a subject through dialysis.

In some aspects, the present disclosure provides a facility comprising a plurality of dry compositions or concentrated compositions. In certain embodiments, the facility manufactures the dry composition or concentrated composition described herein or components thereof. In one embodiment, the facility is a pharmaceutical manufacturing site. In certain embodiments, the facility distributes the dry composition or concentrated composition described herein or components thereof. For example, the facility may be a distribution center. In certain embodiments, the facility administers the dry composition or concentrated composition described herein or components thereof. In one embodiment, the facility is a hospital or clinic. The facility may administer the dry composition or concentrated composition to a subject through dialysis.

In some aspects, the present disclosure provides a facility comprising a plurality of food compositions. In certain embodiments, the facility manufactures the food compositions described herein or components thereof. In one embodiment, the facility is a food manufacturing site. In certain embodiments, the facility distributes the food compositions described herein or components thereof. For example, the facility may be a distribution center. In certain embodiments, the facility provides the food compositions described herein and components thereof to the subject. In one embodiment, the facility may sell the food composition to the subject. In another embodiment, the facility may prepare the food composition. In another embodiment, the facility may administer the food composition to the subject. For example, the facility may be a distribution center, a commercial kitchen, a restaurant, an eating facility, or a medical facility. In some embodiments, the facility is a location that provides catering or food delivery service to hospitals, clinic or patients. The facility may be located in or within the vicinity of a hospital or clinic, such as within 0.1, 0.5, 1, or 5 miles of a hospital or clinic.

Kits

Diet

The invention also provides kits. In some aspects, the present disclosure provides a kit comprising: (a) a pre-packaged food composition as described herein; and (b) instructions for using the pre-packaged food composition. The kits include one or more food compositions described herein, in suitable packaging, and can further comprise written material that can include instructions for use, discussion of clinical studies, listing of side effects, and the like. The instructions may comprise an informational package describing the use and attendant benefits of the food composition in treating cancer, obesity or renal disease. Such kits can also include information, such as scientific literature references, package insert materials, clinical trial results, and/or summaries of these and the like, which indicate or establish the activities and/or advantages of the food composition, and/or which describe dosing, administration, the dieting regimen, side effects, drug interactions, or other information useful to the health care provider. Such information can be based on the results of various studies, for example, studies using experimental animals involving in vivo models and studies based on human clinical trials. A kit can comprise one or more complete meals and/or snacks of the food composition described herein. In some embodiments, a kit comprises about, less than about, or more than about 1, 2, 3, 4, 5, 6, 7, 8, 9, 10, 11, 12, 13, 14, 15, 16, 17, 18, 19, 20, 30, 31, 60, 90, 120, 150, 180, 210, or more complete meals and/or snacks of the food composition. The kits may provide complete meals and/or snacks for exactly or at least 1, 2, 3, 4, 5, 6, 7, 8, 9, 10, 11, 12, 13, 14, 15, 16, 17, 18, 19, 20, 30, 31, 60, 90, 120, or more days. Instructions for use can comprise diet regimen instructions, such as instructions to take 1, 2, 3, 4, 5, 6, 7, 8, 9, 10, or more complete meals and/or snacks 1, 2, 3, 4, 5, 6, 7, 8, 9, 10, or more times per day. For example, a kit can comprise a complete meal and/or snack of the food composition supplied as a food product, with each food product packaged separately, multiples of a food product packaged separately according to the number of complete meals and/or snacks of the food composition per administration (e.g. pairs of components), or all food products packaged together (e.g. in a container). As a further example, a kit can comprise a complete meal and/or snack of the food composition as a bottled drink, the kit comprising 1, 2, 3, 4, 5, 6, 7, 8, 9, 10, 11, 12, 13, 14, 24, 28, 36, 48, 72, or more bottles. In an alternative example, a kit can comprise a complete meal and/or snack of the food composition as a nutritional bar, the kit comprising 1, 2, 3, 4, 5, 6, 7, 8, 9, 10, 11, 12, 13, 14, 24, 28, 36, 48, 72, or more nutritional bar. The kit may comprise components of the food composition provided or packaged as separate compositions in separate containers within the kit. In some embodiments, the kit may comprise components of the food composition provided or packaged as a single composition within a container of the kit.

The kit can further contain another agent. In some embodiments, the food composition or component thereof, and the agent are provided or packaged as separate compositions in separate containers within the kit. In some embodiments, the food composition or component thereof, and the agent are provided or packaged as a single composition within a container in the kit. Suitable packaging and additional articles for use (e.g., measuring cup for liquid preparations, foil wrapping to minimize exposure to air, and the like) are known in the art and can be included in the kit. Kits described herein can be provided, marketed and/or promoted to health providers, including physicians, nurses, pharmacists, formulary officials, and the like. Kits can also, in some embodiments, be marketed directly to the consumer.

The kit can further contain a pre-packaged liquid composition, pre-packaged concentrated composition, or a pre-packaged dry composition described herein. The kit can comprise instructions directing the administration of the pre-packaged liquid composition, or pre-packaged concentrated composition, or dry composition. In some embodiments, a kit comprises about, less than about, or more than about 1, 2, 3, 4, 5, 6, 7, 8, 9, 10, 11, 12, 13, 14, 15, 16, 17, 18, 19, 20, 30, 31, 60, 90, 120, 150, 180, 210, or more pre-packaged liquid compositions, pre-packaged concentrated compositions or pre-packaged dry compositions.

In some embodiments, a kit can comprise a multi-day supply of complete meals and/or snacks of the food composition as described herein. The kit can comprise instructions directing the administration of the multi-day supply of complete meals and/or snacks of the food composition over a period of multiple days. The multi-day supply can be a one-month supply, a two-month supply, or a multi-week supply. The multi-day supply can be a 90-day, 180-day, 3-month or 6-month supply. The kit can include packaged daily complete meals and/or snacks of the food composition, such as packages of 1, 2, 3, 4, or 5 complete meals and/or snacks of the food composition. The kit can be packaged with other dietary supplements, vitamins, and/or meal replacement bars, mixes, and beverages.

Dialysis

In some aspects, the present disclosure provides a kit comprising: (a) a pre-packaged liquid composition as described herein; and (b) instructions for using the pre-packaged liquid composition. In some aspects, the present disclosure provides a kit comprising: (a) a pre-packaged dry composition or concentrated composition as described herein; and (b) instructions for using the pre-packaged dry composition. The kits include one or more liquid compositions, concentrated compositions, or dry compositions described herein, in suitable packaging, and can further comprise written material that can include instructions for use, discussion of clinical studies, listing of side effects, and the like. The instructions may comprise an informational package describing the use and attendant benefits of the liquid composition or dry composition in treating cancer, obesity or renal disease. Such kits can also include information, such as scientific literature references, package insert materials, clinical trial results, and/or summaries of these and the like, which indicate or establish the activities and/or advantages of the liquid composition, concentrated composition, or dry composition, and/or which describe dosing, administration, side effects, drug interactions, or other information useful to the health care provider. Such information can be based on the results of various studies, for example, studies using experimental animals involving in vivo models and studies based on human clinical trials. A kit can comprise one or more dialysis bags containing the liquid composition, concentrated composition, or dry composition described herein. In some embodiments, a kit comprises about, less than about, or more than about 1, 2, 3, 4, 5, 6, 7, 8, 9, 10, 11, 12, 13, 14, 15, 16, 17, 18, 19, 20, 30, 31, 60, 90, 120, 150, 180, 210, or more dialysis bags containing the liquid composition, concentrated composition, or dry composition. The kits may provide dialysis bags containing the liquid composition, concentrated composition, or dry composition for exactly or at least 1, 2, 3, 4, 5, 6, 7, 8, 9, 10, 11, 12, 13, 14, 15, 16, 17, 18, 19, 20, 30, 31, 60, 90, 120, or more days. Instructions for use can comprise dialysis regimen instructions, such as instructions to use 1, 2, 3, 4, 5, 6, 7, 8, 9, 10, or more dialysis bags containing the liquid composition, concentrated composition, or dry composition 1, 2, 3, 4, 5, 6, 7, 8, 9, 10, or more times per day. For example, a kit can comprise a dialysis bag containing the liquid composition, concentrated composition, or dry composition supplied as a single-use dialysis bag, with each single-use dialysis bag packaged separately, multiples of a single-use dialysis bag packaged separately according to the number of dialysis bags containing the liquid composition, concentrated composition, or dry composition per administration (e.g. pairs of single-use dialysis bag), or all single-use dialysis bag packaged together (e.g. in a container). The kit may comprise components of the dialysis bag containing the liquid composition, concentrated composition, or dry composition provided or packaged as separate compositions in separate containers within the kit. In some embodiments, the kit may comprise components of the dialysis bag containing the liquid composition, concentrated composition, or dry composition provided or packaged as a single composition within a container of the kit.

The kit can further contain another agent. In some embodiments, the dialysis bag containing the liquid composition, concentrated composition, or dry composition or component thereof, and the agent are provided or packaged as separate compositions in separate containers within the kit. In some embodiments, the liquid composition, concentrated composition, dry composition, or component thereof, and the agent are provided or packaged as a single composition within a container in the kit. Suitable packaging and additional articles for use (e.g., aqueous solution for reconstituting the dry composition or concentrated composition, measuring cup for liquid preparations, wrapping to minimize exposure to air, and the like) are known in the art and can be included in the kit. Kits described herein can be provided, marketed and/or promoted to health providers, including physicians, nurses, pharmacists, formulary officials, and the like. Kits can also, in some embodiments, be marketed directly to the consumer.

The kit can further contain a pre-packaged liquid composition, pre-packaged concentrated composition, or a pre-packaged dry composition described herein. The kit can comprise instructions directing the administration of the pre-packaged liquid composition, pre-packaged concentrated composition or pre-packaged dry composition. In some embodiments, a kit comprises about, less than about, or more than about 1, 2, 3, 4, 5, 6, 7, 8, 9, 10, 11, 12, 13, 14, 15, 16, 17, 18, 19, 20, 30, 31, 60, 90, 120, 150, 180, 210, or more pre-packaged liquid compositions, pre-packaged concentrated compositions or pre-packaged dry compositions.

In some embodiments, a kit can comprise a multi-day supply of dialysis bags containing the liquid composition, concentrated composition, or dry composition as described herein. The kit can comprise instructions directing the administration of the multi-day supply of dialysis bags containing the liquid composition, concentrated composition, or dry composition over a period of multiple days. The multi-day supply can be a one-month supply, a two-month supply, or a multi-week supply. The multi-day supply can be a 90-day, 180-day, 3-month or 6-month supply. The kit can include packaged dialysis bags containing the liquid composition, concentrated composition, or dry composition, such as packages of 1, 2, 3, 4, or 5 dialysis bags containing the liquid composition, concentrated composition, or dry composition. The kit can be packaged with a food composition described herein, dietary supplements, vitamins, and/or meal replacement bars, mixes, and beverages.

Systems

The present disclosure provides a system for placing a subject under dialysis and/or a nutritional diet with a composition disclosed herein to aid in the treatment or prevention of a disease. The system may carry out any of the methods disclosed herein and may use any of the compositions disclosed herein.

The dialysis systems of the present disclosure can be controlled and modified to provide various dialysis therapies, as desired. The dialysis systems may be modified (e.g. increase/decrease the number of exchanges, increase/decrease the amount of dialysate used during each exchange, and/or use an adjusted dialysate formulation) to adjust to a subject's medical progress. The dialysis systems may facilitate peritoneal dialysis, hemodialysis and other forms of dialysis. The dialysis systems may comprise (a) a dialysis container comprising a composition disclosed herein, (b) tubing, and (c) a collection container. In some embodiments, the dialysis systems further comprise a machine for facilitating and/or automating fluid exchange. In some aspects, the present disclosure provides a dialysis system, comprising: a dialysis container comprising a liquid composition disclosed herein, a concentrated composition disclosed herein or a dry composition disclosed herein, and a dialysis machine configured to administer the liquid composition, the concentrated composition or the dry composition. In some embodiments, the dialysis machine comprises a pump, a pressure monitor, air trap, air detector, a clamp, and/or a filter. In some aspects, the present disclosure provides a dialysis system, comprising: a dialysis container comprising a liquid composition disclosed herein, a concentrated composition disclosed herein or a dry composition disclosed herein.

Peritoneal Dialysis.

Peritoneal dialysis (PD) is a treatment that uses the lining of a subject's abdomen, i.e. the peritoneum, and a dialysate to clean the subject's blood. Any of the liquid compositions, concentrated compositions, and dry compositions may be used as a dialysate in PD. Dialysate absorbs waste and fluid from the blood, using the peritoneum as a filter. In some embodiments, the dialysis system involves continuous ambulatory PD (CAPD) or continuous cycler-assisted PD (CCPD).

Figure 14A:
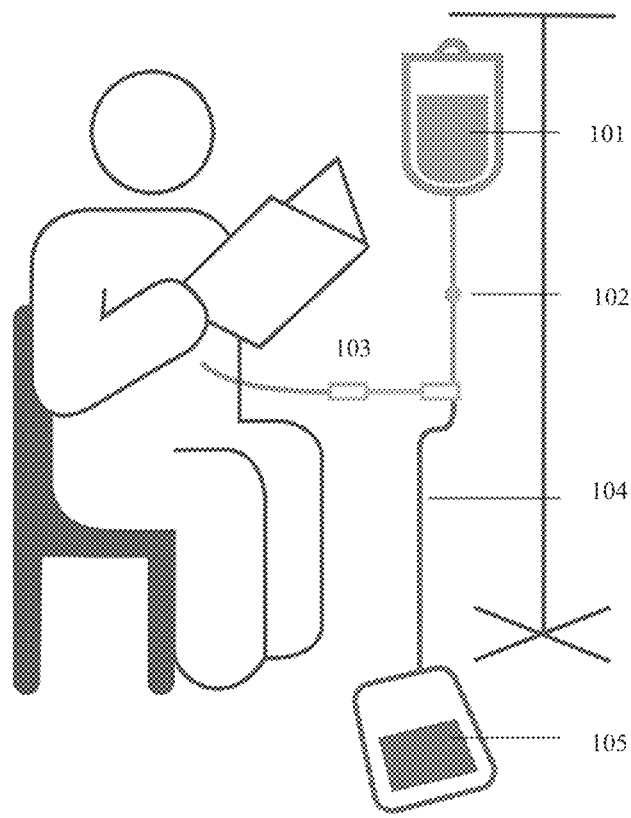
FIG. 14A and FIG. 14B show exemplary dialysis systems, CAPD and CCPD respectively, that is configured to use administer the compositions described herein.

CAPD is "continuous," machine-free and can be done at any time. The treatment may involve placing about two quarts of cleansing fluid into the subject's abdomen and later draining it. In some embodiments, CAPD can be done by hooking up a plastic bag of cleansing fluid to the tube in the peritoneum. The subject may raise the dialysis bag to approximately shoulder level to pull the dialysis fluid into the peritoneum. When empty, the dialysis bag is removed and discarded. When an exchange (putting in and taking out the fluid) is finished, the fluid is drained from the subject's abdomen. In some embodiments, this process is performed several times in a 24-hour period, such as 1, 2, 3, 4, 5, 6 or 7 times, or as needed. Each exchange may take about 30 minutes, 45 minutes, 1 hour, 2 hours, 3 hours, 4 hours, 5 hours, or 6 hours. FIG. 14A shows an exemplary CAPD process (source: https://www.niddk.nih.gov/health-information/kidney-disease/kidney-failure/peritoneal-dialysis). As shown in FIG. 14A, a patient undergoing CAPD may hooked up to a dialysis bag 101 and waste container 105 by a catheter placed in the patient's peritoneum and connecting tubes 104. The transfer set 103 connects the catheter to the dialysis bag 101 to perform dialysis exchange and can be designed to reduce the risk of infection. The transfer set may be "Y-shaped," and one branch of the Y-tube may connect to the waste container 105, while the other branch may connect to a dialysis bag 101 containing a dialysis solution as described herein. In some embodiments, the dialysis solution is warmed prior to use by the subject. The dialysis bag 101 is placed above the patient's peritoneum in a way to allow the fluid in the dialysis bag to enter into the patient, such as on a pole as illustrated in FIG. 14A.

Figure 14B:
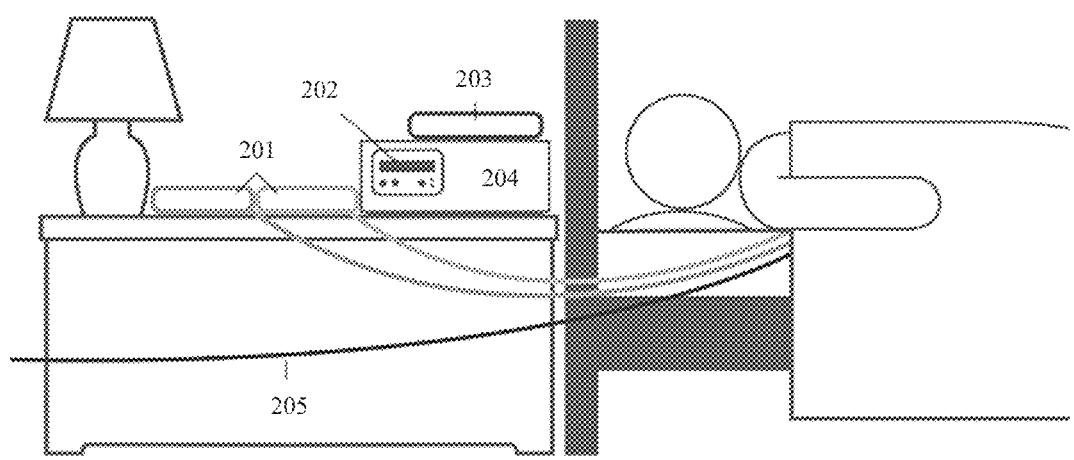

CCPD, also known as automated peritoneal dialysis (APD), differs from CAPD in that a machine (cycler) delivers and then drains the cleansing fluid for the subject. The treatment may be performed at any time, especially at night. The dialysis system automatically performs dialysis therapy on a patient, for example, during nighttime while the patient sleeps. The subject may be attached to the machine for an extended period of time, such as 8, 9, 10, 11, or 12 hours per day. FIG. 14B shows an exemplary CCPD process (source: https://www.niddk.nih.gov/health-information/kidney-disease/kidney-failure/peritoneal-dialysis). As shown in FIG. 14B, a patient undergoing CCPD may hooked up to a supply of dialysis solution disclosed herein 201 and waste line 205. The dialysis may be facilitated by a dialysis machine 204 (also known as a cycler). The dialysis machine may further comprise a heater 203. The flow of dialysis solution may be monitored by a fluid meter 202. The fluid meter 202 may measure and record how much solution the cycler 204 removes. In some embodiments, the cycler 204 compares the amount of dialysis solution that was put into the subject with the amount of fluid that drains out. The cycler 204 may to fill and empty the subject's peritoneum several times a night, such as three to five times, while the subject sleeps.

Hemodialysis.

Figure 15:
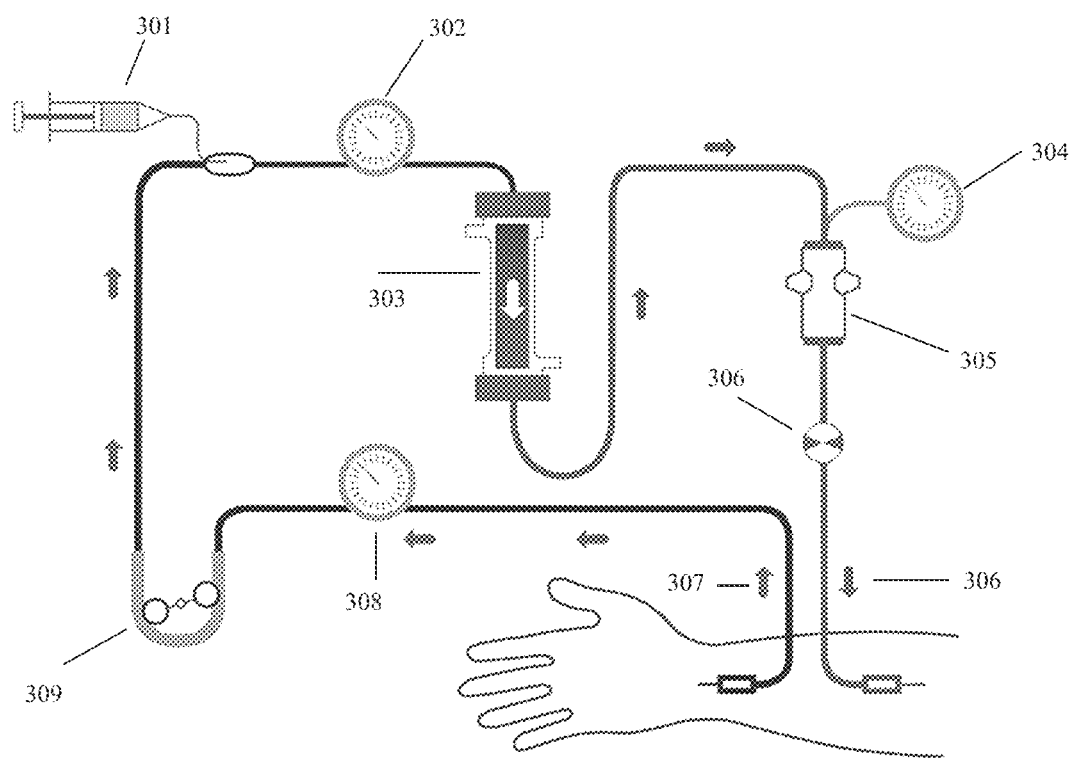
FIG. 15 shows and exemplary dialysis system for hemodialysis that is configured to use administer the compositions described herein.
Figure 16:
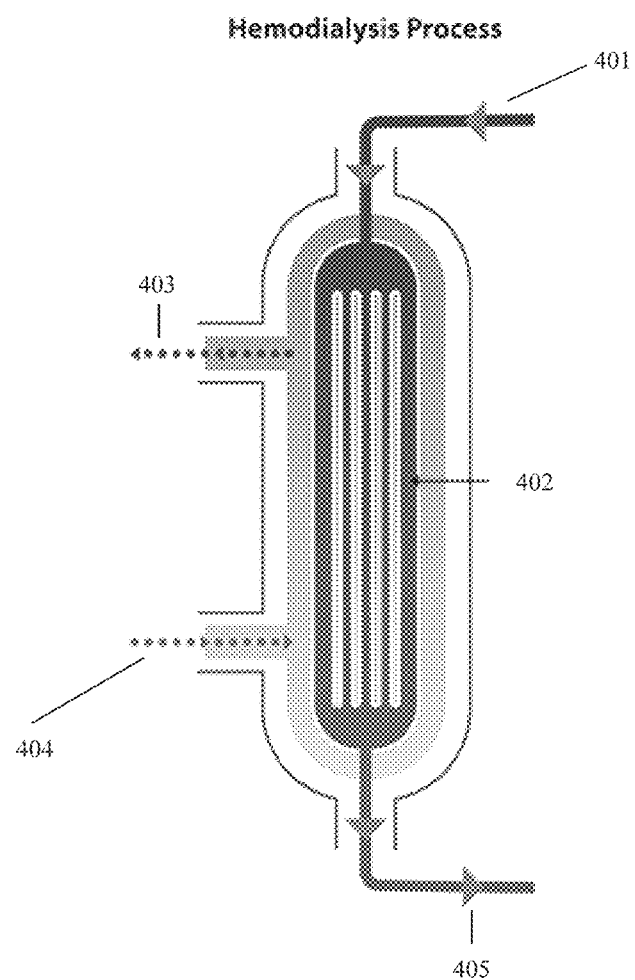
FIG. 16 depicts the typical hemodialysis process.

Hemodialysis is a treatment to filter wastes and water from your blood. In hemodialysis, a dialysis machine and a special filter called an "artificial kidney," or a "dialyzer," are used to clean a subject's blood. The blood goes through the dialyzer, which is located outside of the subject's body. FIG. 15 is an exemplary schematic representation of hemodialysis (source: https://www.niddk.nih.gov/health-information/kidney-disease/kidney-failure/hemodialysis). FIG. 16 provides an overview of the filtering process in hemodialysis (source: https://www.niddk.nih.gov/health-information/kidney-disease/kidney-failure/hemodialysis). As shown in FIG. 15, a patient undergoing hemodialysis may be connected to a dialysis machine by inserting two needles in the subject's arm. Each needle is attached to a soft tube connected to the dialysis machine. The dialysis machine pumps blood through the filter and returns the blood to the patient. Through one of the needles, blood is removed for dialysis 307. At various stages of dialysis, the unfiltered and filtered blood is monitored with an arterial pressure monitor 308, dialyzer inflow pressure monitor 302, and venous pressure monitor 304. An anticoagulant 301 may be used to prevent blood clotting. The dialysis machine pumps the blood through a filter 303 (also known as a dialyzer) with a pump 309. The dialyzer 303 has two parts, one for your blood and one for a washing fluid called dialysate. A thin membrane separates these two parts. Once the blood enters the filter 303 at one end of the filter 401, the blood is forced into many, very thin, hollow fibers 402. As blood passes through the hollow fibers, dialysis solution 404 as disclosed herein passes in the opposite direction on the outside of the fibers. Waste products from the blood move into the dialysis solution and out of the filter 403. Filtered blood remains in the hollow fibers and returns to the body. Some nutrients from the dialysis solution may also return to the body with the filtered blood.

In some embodiments, hemodialysis is performed about 1, 2, 3, 4, 5, 6 or 7 times per week for about 1, 2, 3, 4, 5 or 6 hours at a time, or as needed.

EXAMPLES

Example 1: Cancer Therapy Process

A cancer therapy regimen is provided to a patient previously identified as having a form of cancer. The patient is diagnosed with a tumor, solid or liquid, in the primary or metastatic stage. The regimen involves utilizing a combination of a nutritionally modified diet and dialysis with compositions disclosed here. The regimen involves metabolic intervention therapy that can be tailored to the needs of the individual patient. As depicted in FIG. 1, a metabolic cancer therapy can be provided to a patient diagnosed with cancer. The cancer patient is treated with dialysis and/or a nutritional diet in order to deplete targeted nutrient(s)

The patient is primed with any food composition described herein, i.e. a depleting diet, for approximately 3 days ("the priming stage"). During the priming stage, the patient's entire diet comprises any food composition described herein, with the exception of food and beverages approved by the regimen. The patient's plasma amino acid levels are measured and profiled by targeted LC-MS assay before and after the priming stage.

On approximately day 4 of the regimen, the patient continues to consume a depleting diet, and begins dialysis treatment—e.g. hemodialysis or peritoneal dialysis. The patient may undergo hemodialysis or peritoneal dialysis alone, or undergo either form dialysis serially or interchangeably within the therapy. A patient undergoing hemodialysis undergoes dialysis with a liquid composition, concentrated composition, or dry composition described herein ("dialysis solution") at a facility described herein. The patient receives the dialysis solution for approximately 4 hours during the day or overnight. The patient receives dialysis treatment at least 3 times a week, for approximately 4 hours for each dialysis treatment. After each dialysis treatment, the patient's plasma amino acid profile is analyzed for monitoring treatment effect progression. A patient undergoing peritoneal dialysis undergoes dialysis with a liquid composition, concentrated composition, or dry composition described herein ("dialysis solution") at a facility described herein, at the patient's home, or a convenient location. The patient receives the dialysis solution for approximately 8-12 hours per day or 24 hours continuously. For continuous peritoneal dialysis, the patient carries a portable device that administers the dialysis solution. The patient's plasma amino acid profile is analyzed approximately every 3 days for monitoring treatment effect progression.

For a typical dialysis treatment with a single-time/single-day clearance of 30% or higher, the patient's amino acid profile achieves therapeutic depletion levels after no more than approximately 8 weeks, as determined by the LC-MS assay. At this point, the patient discontinues dialysis treatment, but continues to take depleting diets until complete remission is achieved. Once the patient reaches complete remission, the patient remains on the depleting diet for approximately 2 weeks to stabilize complete remission, in which the patient is tested throughout.

Throughout the cancer therapy regimen, the patient's disease progression is monitored by companion test. Any serious complications that arise may be conveniently stopped or limited by allowing the patient to resume a normal diet. The cancer therapy regimen is resumed once the patient's condition is stabilized. The patient is permitted to continue to take painkillers or other cancer medicines as long as it does not interfere with the metabolic intervention treatment.

Example 2: Obesity Therapy Process

For a compatibility primer test, dietary intervention may be administrated for 1-4 weeks with companion plasma nutrient test to indicate the safety and potential efficacy in an individual patient. As described in Example 1, during the test, the patient will only eat and drink the prescribed food composition. For long term use, the diet regimen may be administrated as long as the subject remains obese.

Example 3: Renal Disease Therapy Process

With technical improvement on safety and clearance efficiency in our dialysis procedure, the renal disease patient may solely rely on dialysis for normal nutrient nourishment through the administration of the dry composition, concentrated composition, or liquid composition described herein. The dialysis procedure, as set forth in Example 1, is followed. For long term use, dialysis may be administrated as long as the subject's renal function remains impaired or lost.

Example 4: Cancer Therapy Process: Diet Only

For a compatibility primer test, dietary intervention may be administrated for 1-4 weeks with companion cancer progression test and plasma nutrient test to indicate the safety and potential efficacy in an individual patient. As described in Example 1, during the test, the patient will only eat and drink the prescribed food. For long term use, the patient on the diet regimen may be administrated to the subject as long as the tumor is not completely cured.

Example 5: Cancer Therapy Process: Dialysis Only

With technical improvement on safety and clearance efficiency in our dialysis procedure, the cancer patient may solely rely on dialysis both for targeted depletion of cancer-addicted nutrients in plasma and for normal nutrient nourishment through the administration of the dry composition, concentrated composition, or liquid composition described herein. A dialysis only treatment is particularly applicable to late-stage gastrointestinal cancer because patients usually lose the ability to eat and rely solely on nutrient infusion. For long term use, dialysis may be administrated to the subject as long as the tumor is not completely cured.

Example 6: Dialysis Fluid Composition

Table 2 as presented below provides an exemplary formulation of the dialysis fluid—dry composition, concentrated composition, or liquid composition—described herein.

TABLE 2

| Dialysis fluid composition | | |
|---|---|---|
| Dextrose (/L) | mmole | |
| Hemodialysis only | 5.5-11.0 | |
| peritoneal dialysis only | 83-236 | |
| Osmolarity (mOsmol/L) | 300-718 | |
| pH | 6.0 (4.0-6.5) | |
| | mmole | mEq |
| Ionic Concentration (/L) | | |
| Sodium | 132 | 132 |
| Calcium | 1.75 | 3.5 |
| Potassium | 2 | 2 |
| Magnesium | 0.25 | 0.5 |
| Chloride | 96 | 96 |

TABLE 2-continued

| Dialysis fluid composition | | |
|---|---|---|
| Buffer (L) | | |
| HCO3 | 20-50 | 20-50 |
| Acetate | 2.0-5.0 | 2.0-5.0 |
| Lactate | 40 | 40 |
| Amino acid (/L) | micromole | MW | microgram |
| Alanine | 347.5 | 89.0935 | 30.96 |
| Arginine | 60.25 | 174.2017 | 10.50 |
| Asparagine | 57.5 | 132.1184 | 7.60 |
| Aspartic acid | 8 | 133.1032 | 1.06 |
| Beta-alanine | 19.5 | 89.0935 | 1.74 |
| Cystine | 40.25 | 240.3 | 9.67 |
| Glutamic acid | 72 | 147.1299 | 10.59 |
| Glutamine | 547.5 | 146.1451 | 80.01 |
| Glycine | 212.5 | 75.0669 | 15.95 |
| Histidine | 83.5 | 155.1552 | 12.96 |
| Isoleucine | 79.75 | 131.1736 | 10.46 |
| Leucine | 119 | 131.1736 | 15.61 |
| Lysine | 195 | 146.1882 | 28.51 |
| Methionine | 22.25 | 149.2124 | 3.32 |
| Phenylalanine | 55.25 | 165.19 | 9.13 |
| Proline | 222.5 | 115.131 | 25.62 |
| Serine | 109.75 | 105.093 | 11.53 |
| Threonine | 137.25 | 119.1197 | 16.35 |
| Tryptophan | 66.5 | 204.2262 | 13.58 |
| Tyrosine | 63.75 | 181.1894 | 11.55 |
| Valine | 242.5 | 117.1469 | 28.41 |
| Vitamin (/L) | micromole | Average RDI | |
| Vitamin A | 0.052 | 50 IU | |
| Vitamin C | 7.57 | 1333 mcg | |
| Vitamin B6 | 1.48 | 250 mcg | |
| Vitamin E | 0.90 | 0.43 IU | |
| Folate (Vit B9) | 15.18 | 6.7 mcg | |
| Vitamin D | 0.0044 | 67 IU | |
| Vitamin K | 0.0038 | 1.7 mcg | |
| Thiamine | 0.075 | 20 mcg | |
| Riboflavin | 0.053 | 20 mcg | |
| Niacin | 4.71 | 580 mcg | |
| Vitamin B12 | 0.000030 | 0.04 mcg | |
| Pantothenic acid | 0.38 | 83 mcg | |
| Biotin | 0.0021 | 0.50 mcg | |
| Choline | 79.99 | 8333 mcg | |
| Mineral (/L) | micromole | MW | microgram |
| Iron | 2.3279 | 55.845 | 130.00 |
| Copper | 0.2360 | 63.546 | 15.00 |
| Chromium | 0.0096 | 51.9961 | 0.50 |
| Fluoride | 3.1582 | 18.9984 | 60.00 |
| Iodine | 0.0197 | 126.90447 | 2.50 |
| Manganese | 0.5461 | 54.938044 | 30.00 |
| Molybdenum | 0.0078 | 95.94 | 0.75 |
| Selenium | 0.0117 | 78.96 | 0.92 |
| Zinc | 2.6002 | 65.38 | 170.00 |

Example 7: Food Composition

Table 3 as presented below provides an exemplary formulation of the food composition described herein.

TABLE 3

| Food composition | | |
|---|---|---|
| | gm % | kcal % |
| Protein | 17 | 17.6 |
| Carbohydrate | 68.6 | 69.8 |

TABLE 3-continued

| Food composition | | |
|---|---|---|
| Fat | 5 | 11.6 |
| kcal/gm | | 3.87 |
| Ingredient (gm) | gm | kcal |
| Gelatin | 131 | 524 |
| Essential amino acids | | |
| L-Arginine# | 0 | 0 |
| L-Histidine-HCl-H2O | 3 | 13 |
| L-Isoleucine | 6 | 22 |
| L-Leucine | 7 | 28 |
| L-Lysine-HCl | 3 | 14 |
| L-Methionine | 5 | 19 |
| L-Phenylalanine | 4 | 18 |
| L-Threonine | 5 | 19 |
| L-Tryptophan | 2 | 8 |
| L-Valine | 4 | 16 |
| Nonessential amino acids | | |
| L-Alanine | | |
| L-Asparagine-H2O | | |
| L-Aspartate | | |
| L-Cystine | | |
| L-Glutamic Acid | | |
| L-Glutamine | | |
| Glycine | | |
| L-Proline | | |
| L-Serine | | |
| L-Tyrosine | | |
| Total L-Amino Acids | | |
| Corn Starch | 550.5 | 2202 |
| Maltodextrin 10 | 125 | 500 |
| Cellulose | 50 | 0 |
| Corn Oil | 50 | 450 |
| Mineral Mix(including calcium, chloride, chromium, cupric, ferric, iodate, magnesium, manganous, phosphate, potassium, selenite, sodium, sulfate, zinc) | 35 | 0 |
| Sodium Bicarbonate | 7.5 | 0 |
| Vitamin Mix (vitamin A, C, D, E and B family) | 10 | 40 |
| Choline Bitrartrate | 2 | 0 |
| Total | 1000.1 | 3872 |

Example 8: Effect of Diet Only on Cancer

The effect of nutritional diet was tested in colon, breast, prostate and pancreatic cancer. The mice in the studies were placed one of the diets shown in FIG. 2. FIG. 3 shows an overview of the diet compositions used in the studies of the present disclosure and Table 5 of Example 14 further describes the diets. In the studies shown in FIG. 4 to FIG. 13B, the "complete diet" was the "designed control" of FIG. 3. In FIG. 2, MEAD201 and MEAD203 were depleted in 5 and 9 non-essential amino acids, respectively. MEAD202 was lacking 3 non-essential amino acids and insufficient 1 non-essential amino acid. Protein Y is natural protein casein, a common food ingredient to provide protein. Protein Z is soy protein. Protein X is collagen (gelatin).

Colon Cancer

Procedure. Athymic nude mice were implanted with HCT116 cells by subcutaneous injection. The mice were approximately 5-6 week old. The study had two groups: mice administered with a complete diet and mice administered with MEAD202. Each group had 5 mice. The mice were placed on the respective diet on day 7. The mice were fed ad libitum. The complete diet and MEAD 202 compositions are described in Table 5 of Example 14. The tumor sizes were monitored 3 times weekly. Tumor tissues and plasma samples were collected. Significance is shown: * for $P<0.05$,  for $P<0.01$, * for $P<0.001$.

Results.

Figure 4:
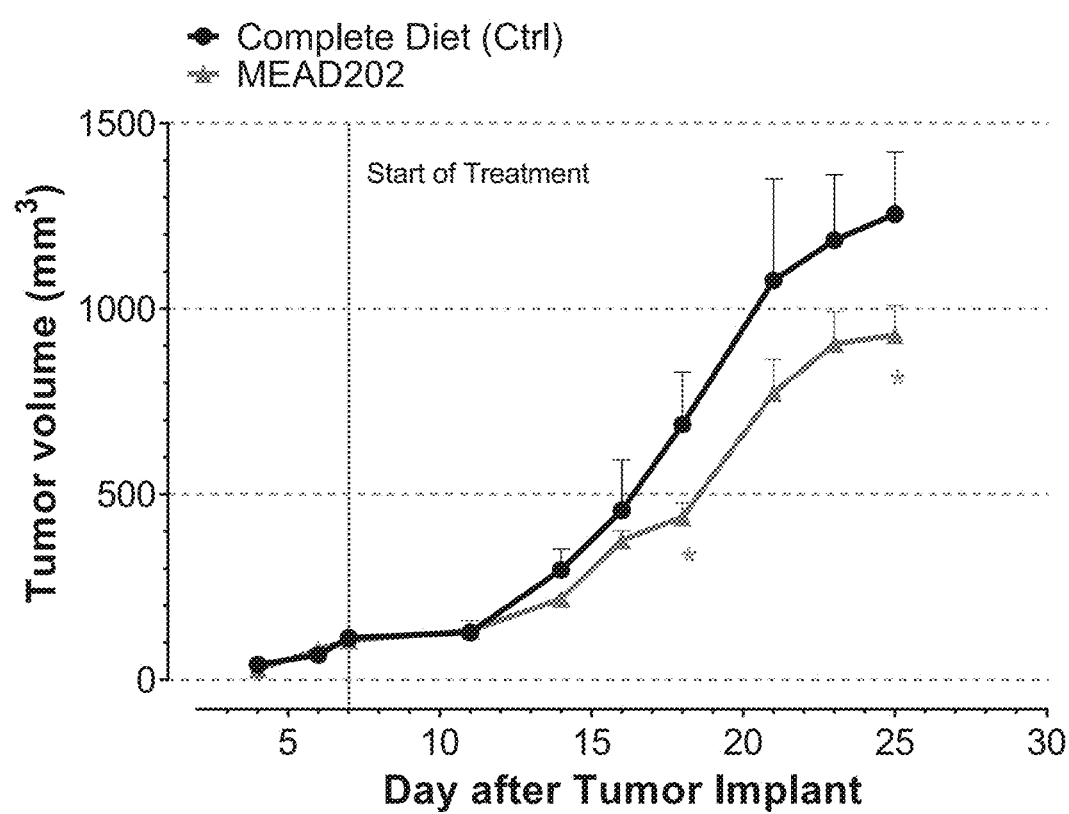
FIG. 4 depicts a graph showing the effects of a complete diet and MEAD202 on tumor volume ($mm^3$) in colon cancer (HCT116). Mice with implanted HCT116 cells were on diet treatment on day 7. The tumor sizes were monitored 3 times weekly. Each group had 5 mice. Significance is shown: * for $P<0.05$,  for $P<0.01$, * for $P<0.001$.

As shown in FIG. 4, the mice that were treated with MEAD202 exhibited a significant decrease in tumor volume in comparison to the mice that were treated with a complete diet. During the study, the mice treated with MEAD202 consistently had a lower tumor volume than the mice treated the complete diet. By day 25, the tumor volume for the MEAD202 mice were over 25% lower than the complete diet mice.

Triple Negative Breast Cancer

Procedure.

Figure 5A:
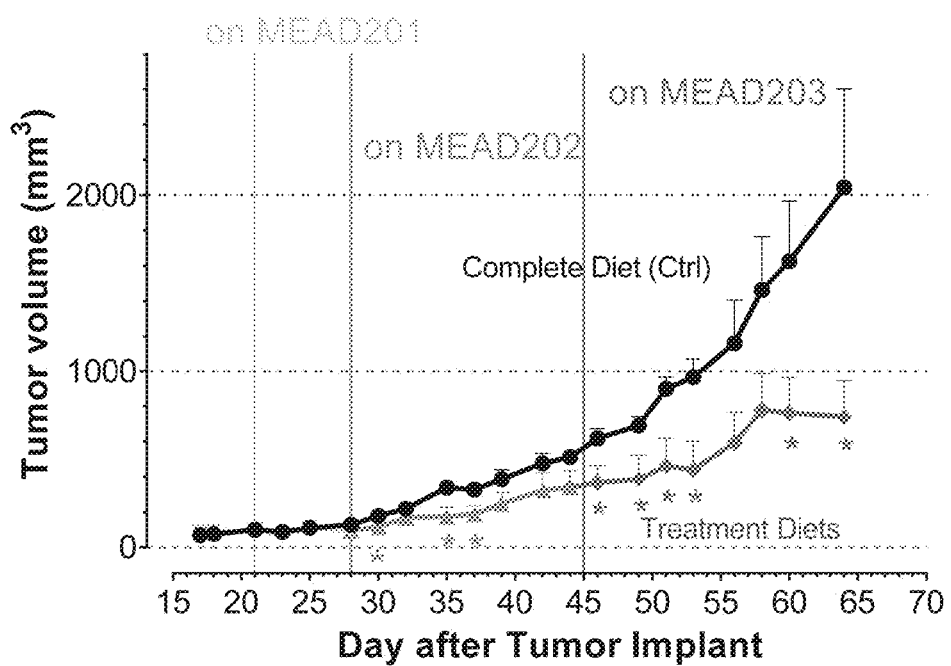
FIG. 5A depicts a graph showing the effects of a complete diet (Ctrl) and treatment diets on tumor volume ($mm^3$) over time (days after tumor implant) in triple negative breast cancer (MDA-MDB-231). Mice with implanted MDA-MDB-231 cells were on diet treatment on day 20. The tumor sizes were monitored 3 times weekly. Each group had 5 mice. Significance is shown: * for $P<0.05$,  for $P<0.01$, * for $P<0.001$.
Figure 5B:
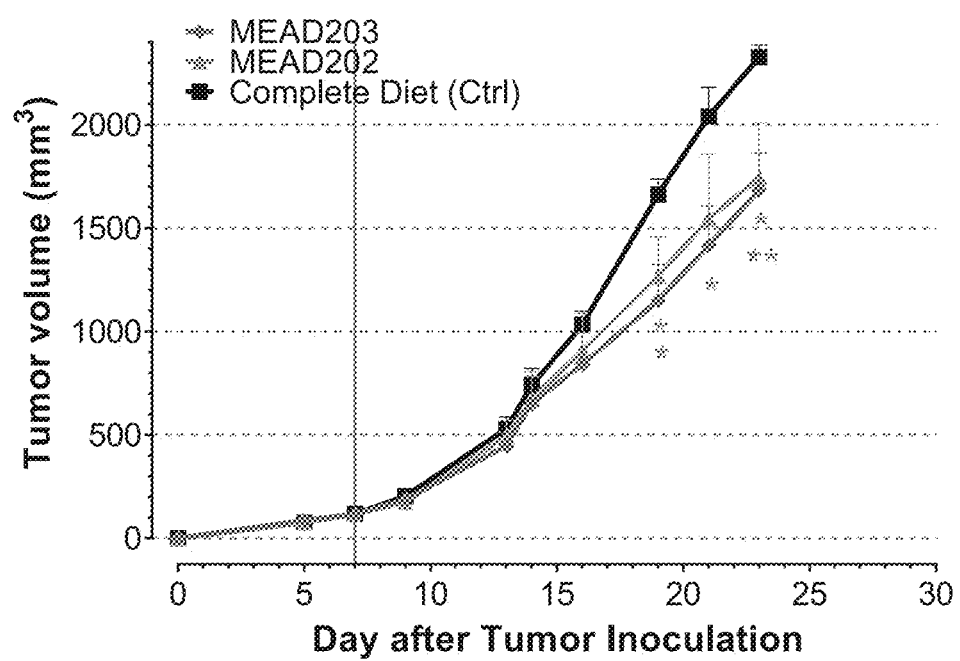
FIG. 5B depicts a graph showing the effects of a complete diet (Ctrl), MEAD202 and MEAD203 on tumor volume ($mm^3$) over time (days after tumor inoculation) in triple negative breast cancer (MDA-MDB-231). Mice with implanted MDA-MDB-231 cells were on diet treatment on day 7. The tumor sizes were monitored 3 times weekly. Each group had 5 mice. Significance is shown: * for $P<0.05$,  for $P<0.01$, * for $P<0.001$.

In FIG. 5A, NOD-SCID mice were implanted with MDA-MDB-231 cells by subcutaneous injection. The mice were 5-6 weeks old. The study in FIG. 5A had two groups: mice administered with a complete diet and mice administered with treatment diets [MEAD202 (day 28-45) and MEAD203 (after day 45)], and the mice were placed on the respective diet on day 20. In FIG. 5B, athymic nude mice were implanted with MDA-MDB-231 cells by subcutaneous injection. The mice were 5-6 weeks old. The study in FIG. 5B had 3 groups: mice administered with a complete diet, mice administered with MEAD202, and mice administered with MEAD203, and the mice were place on the respective diet on day 7. Each group had 5 mice. The complete diet and treatment diet compositions are described in Table 5 of Example 14. The mice were fed ad libitum. The tumor sizes were monitored 3 times weekly. Tumor tissues and plasma samples were collected. Significance is shown: * for $P<0.05$,  for $P<0.01$, * for $P<0.001$.

Results.

As shown in FIG. 5A and FIG. 5B, the mice that were treated with a nutritional diet exhibited a significant decrease in tumor volume than the mice treated with a complete diet. In the study in FIG. 5A, the mice treated with the treatment diets consistently had a lower tumor volume than the mice treated the complete diet. By day 65, the tumor volume for the treatment diets mice were approximately 60% lower than the complete diet mice. In the study in FIG. 5B, the mice treated with MEAD203 and MEAD202 consistently had a lower tumor volume than the mice treated the complete diet. By day 23, the tumor volume for both the MEAD203 and MEAD202 mice were over 25% lower than the complete diet mice.

Prostate Cancer

Procedure.

Athymic nude mice were implanted with PC-3 cells by subcutaneous injection. The mice were 5-6 weeks old. The study had two groups: mice administered with a complete diet and mice administered with MEAD203. Each group had 5 mice. The mice were placed on the respective diet treatment on day 5. The mice were fed ad libitum. The complete diet and MEAD 203 compositions are described in Table 5 of Example 14. The tumor sizes were monitored 3 times weekly. Tumor tissues and plasma samples were collected. Significance is shown: * for $P<0.05$,  for $P<0.01$, * for $P<0.001$.

Results.

Figure 6:
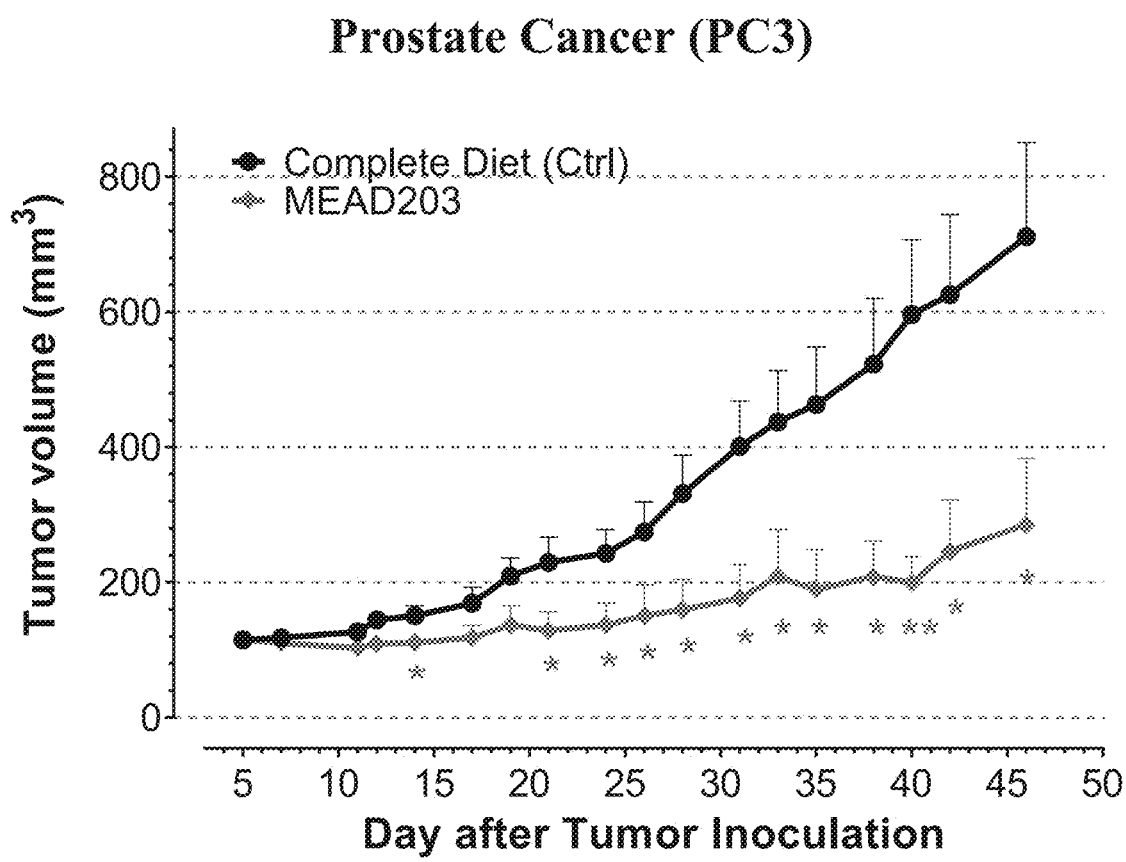
FIG. 6 depicts a graph showing the effects of a complete diet (Ctrl) and MEAD203 on tumor volume ($mm^3$) over time (days after tumor inoculation) in prostate cancer (PC3). Mice with implanted PC-3 cells were on diet treatment on day 5. The tumor sizes were monitored 3 times weekly. Each group had 5 mice. Significance is shown: * for $P<0.05$,  for $P<0.01$, * for $P<0.001$.

As shown in FIG. 6, the mice that were treated with MEAD203 exhibited a significant decrease in tumor volume in comparison to the mice that were treated with a complete diet. During the study, the mice treated with MEAD203 consistently had a lower tumor volume than the mice treated the complete diet. By day 46, the tumor volume for the MEAD203 mice were approximately 60% lower than the complete diet mice.

Pancreatic Cancer

Procedure.

Athymic nude mice were implanted with MIAPaCa-2 cells by subcutaneous injection. The mice were 6-8 weeks old. The study had two groups: mice administered with a complete diet and mice administered with treatment diets [MEAD201 (day 0-24), MEAD202 (day 25-39) and MEAD203 (after day 39)]. Each group had 5 mice. The mice were placed on the respective diet on day 0. The mice were implanted 7 days before being placed on the respective diet. The complete diet and MEAD 202 compositions are described in Table 5 of Example 14. The mice were fed ad libitum. The tumor sizes were monitored 2 times weekly.

Example 9: Diet and Dialysis

The effect of nutritional diet and dialysis was tested in glioblastoma. The mice in the studies were placed on one of the diets shown in FIG. 2 and/or placed on dialysis with one of the compositions shown in FIG. 8. In MEAD102, MEAD103 and MEAD104, an 8-component vitamin cocktail, 10-component vitamin cocktail and 10-component vitamin cocktail were used, respectively. For MEAD102, the vitamin cocktail comprised: vitamin B6, folate (Vit B9), thiamine, riboflavin, vitamin B12, biotin, choline, and inositol. For MEAD103, the vitamin cocktail comprised the MEAD102 cocktail, and niacinamide and pantothenic-Calcium. The compositions for MEAD101, MEAD102, MEAD103 and MEAD104 are described below in Table 8.

TABLE 8

Dialysis compositions

|  | MEAD101 | MEAD102 | MEAD103 | MEAD104 |
| --- | --- | --- | --- | --- |
| Dextrose | 236 mM | 236 mM | 236 mM | 236 mM |
| Sodium chloride | 132 mM | 132 mM | 132 mM | 132 mM |
| Sodium lactate | 40 mM | 40 mM | 40 mM | 40 mM |
| Calcium chloride | 1.75 mM | 1.75 mM | 1.75 mM | 1.75 mM |
| Magnesium chloride | 0.25 mM | 0.25 mM | 0.25 mM | 0.25 mM |
|  | μmole | μmole | μmole | μmol |
| Essential + Arg/Glu Amino acid (/L) | | | | |
| Arginine | — | 60.25 | 60.25 | 60.25 |
| Glutamate | — | 140 | 140 | 140 |
| Histidine | — | 83.5 | 83.5 | 83.5 |
| Isoleucine | — | 79.75 | 79.75 | 79.75 |
| Leucine | — | 119 | 119 | 119 |
| Lysine | — | 195 | 195 | 195 |
| Methionine | — | 22.25 | 22.25 | 22.25 |
| Phenylalanine | — | 55.25 | 55.25 | 55.25 |
| Threonine | — | 137.25 | 137.25 | 137.25 |
| Tryptophan | — | 204.23 | 204.23 | 204.23 |
| Valine | — | 242.5 | 242.5 | 242.5 |
| Vitamin (/L) | | | | |
| Vitamin A | — | 0.052 | 0.052 | 0.052 |
| Vitamin C | — | 7.57 | 7.57 | 7.57 |
| Vitamin B6 | — | 1.48 | 1.48 | 1.48 |
| Vitamin E | — | 0.90 | 0.90 | 0.90 |
| Folate (Vit B9) | — | 15.18 | 15.18 | 15.18 |
| Vitamin D | — | 0.0044 | 0.0044 | 0.0044 |
| Vitamin K | — | 0.0038 | 0.0038 | 0.0038 |
| Thiamine | — | 0.075 | 0.075 | 0.075 |
| Riboflavin | — | 0.053 | 0.053 | 2.65 |
| Niacinamide | — | — | 4.71 | 4.71 |
| Vitamin B12 | — | 0.000030 | 0.000030 | 0.000030 |
| Pantothenic-Ca | — | — | 0.38 | 0.38 |
| Biotin | — | 0.0020 | 0.0020 | 0.0020 |
| Choline | — | 79.99 | 79.99 | 79.99 |

Tumor tissues and plasma samples were collected. Significance is shown: * for P<0.05,  for P<0.01, * for P<0.001.

Results.

Figure 7:
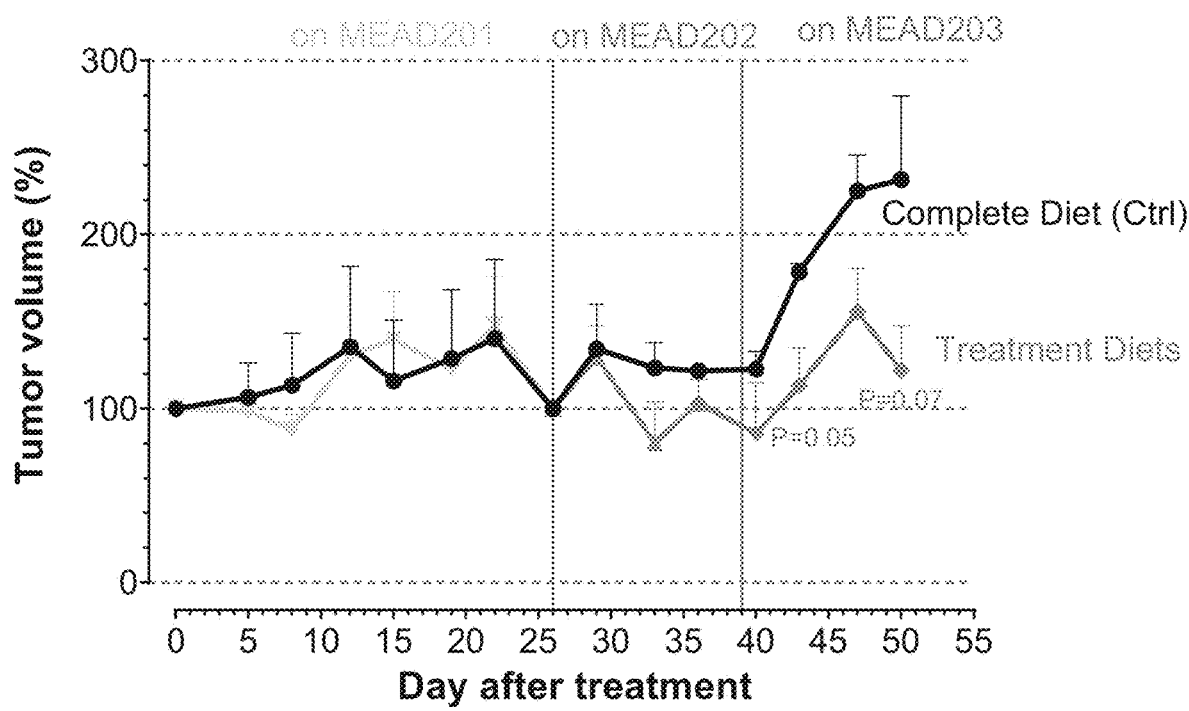
FIG. 7 depicts a graph showing the effects of a complete diet (Ctrl) and treatment diets on tumor volume ($mm^3$) over time (days after treatment) in pancreatic cancer (MIAPaCa-2). Mice with implanted MIAPaCa-2 cells were on diet treatment on day 0. The tumor sizes were monitored 2 times weekly. Each group had 5 mice. Significance is shown: * for $P<0.05$,  for $P<0.01$, * for $P<0.001$.

As shown in FIG. 7, the mice that were treated with the treatment diets exhibited a significant decrease in tumor volume in comparison to the mice that were treated with a complete diet. During the study, the mice treated with the treatment diets on average had a lower tumor volume than the mice treated the complete diet. By day 50, the tumor volume for the treatment diet mice were over 40% lower than the complete diet mice.

Procedure.

Athymic nude mice were implanted with U87MG cells by subcutaneous injection. The mice were 6-8 weeks old. The study in FIG. 9 had 3 groups: mice administered with a complete diet, mice administered with MEAD203, and mice administered with MEAD 203 and placed on dialysis with MEAD101, MEAD102 and MEAD103 at various time points. Each treatment group had 1 mouse. The mice were placed on the respective treatment on day 5. The mice were implanted 7 days before being placed on the respective diet. The mice were fed ad libitum. For dialysis session, approximately 2 mL of dialysis solution was injected in the peritoneal space, and drawn out approximately 2 hours later. The tumor sizes were monitored daily. Arrows indicate the day and type of dialysis fluid were used. The study in FIG. 10 had 4 groups: mice administered a complete diet, mice administered with diet only, mice administered with dialysis only, and mice administered with diet and dialysis. Each group had 6 mice. The mice were placed on the respective treatment on day 1. Diet MEAD203 was used as the treatment diet. Designed Control was used as the control diet. The mice were implanted 22 days before being placed on the respective diets. The mice were fed ad libitum. MEAD103 was used for the dialysis. For each dialysis session, approximately 2 mL of fluid was injected in the peritoneal space, and drawn out approximately 2 hours later. Dialysis was performed on every week day. Mice were monitored every weekday.

Results.

Figure 9:
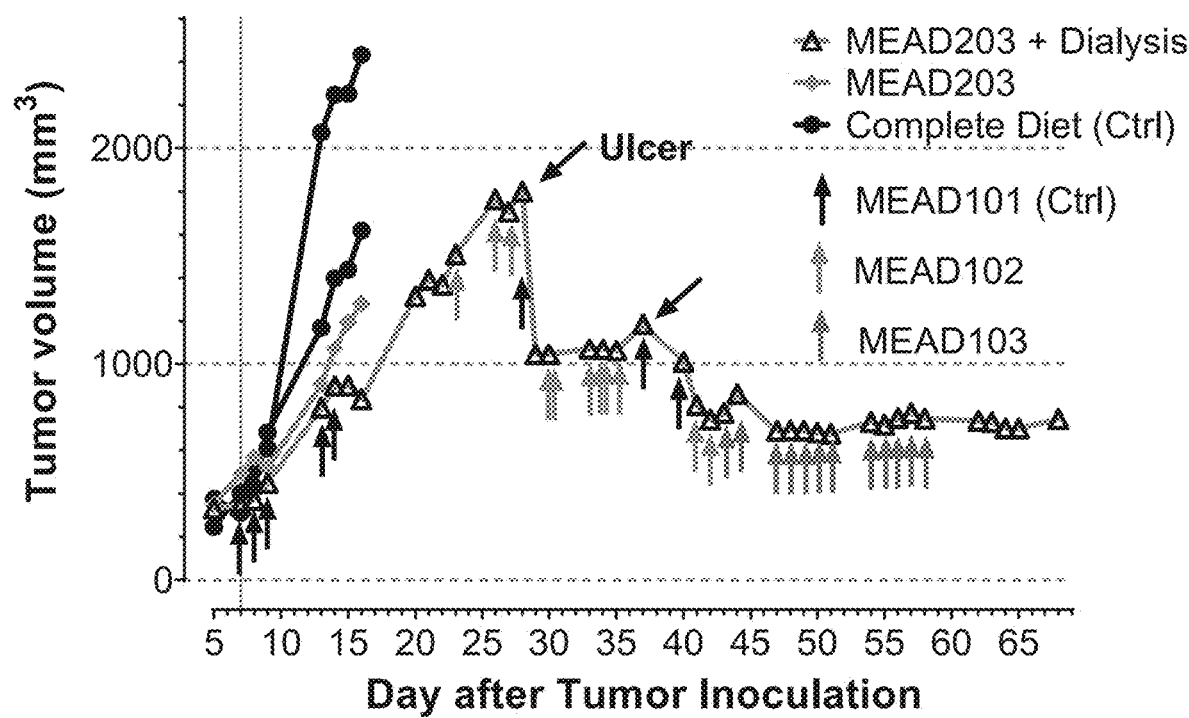
FIG. 9 depicts a graph showing the effects of a complete diet (Ctrl), MEAD203+dialysis, MEAD203 on tumor volume ($mm^3$) over time (days after tumor inoculation) in glioblastoma (U87MG, single mouse study). Mice with implanted U87MG cells were on diet treatment on day 5. The tumor sizes were monitored daily. Each treatment group had 1 mouse. The dialysis fluid was MEAD101 (Ctrl) at day 7, 8, 9, 13, 14, 28, 37, and 40. The dialysis fluid was MEAD102 at day 23, 26, 27, 30, 31, 33, 34, 35, 36, 41, and 42. The dialysis fluid was MEAD103 at 43, 44, 47, 48, 49, 50, 51, 54, 55, 56, 57 and 58.
Figure 10:
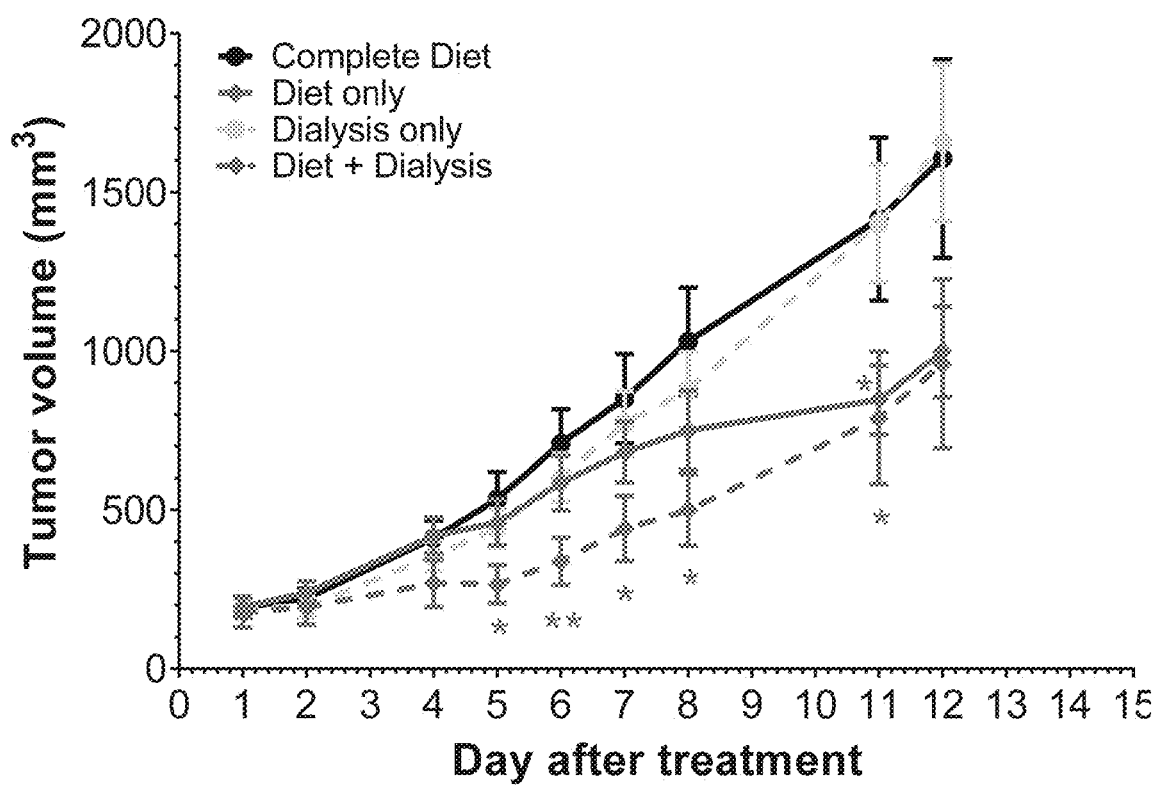
FIG. 10 depicts a graph showing the effects of a complete diet, diet only, dialysis only, and diet+dialysis on tumor volume ($mm^3$) over time (days after treatment) in glioblastoma (U87MG). Mice with implanted U87MG cells were on diet treatment on day 1. The tumor sizes were monitored daily. Each group had 6 mice. Significance is shown: * for $P<0.05$,  for $P<0.01$, * for $P<0.001$.

In FIG. 9, the mouse on the MEAD203 diet and dialysis experienced a reduction in tumor volume. The mice on the complete diet were euthanized at day 16 because the tumor volume was over 2000 mm3 for 3 consecutive measurements. Additionally, the mice were euthanized due to concerns of over ulceration and infection between mice. As shown in FIG. 10, the mice that were administered a treatment of diet+dialysis and the mice treated with diet only exhibited a reduction in tumor volume as compared to the mice on a complete diet and the mice on dialysis only. During the study, the diet+dialysis mice consistently had the lowest tumor volume in comparison to the other treatment groups. By day 12, the mice that were administered a treatment of diet+dialysis and the mice treated with diet only exhibited approximately a 40% reduction in tumor volume as compared to the mice on a complete diet and the mice on dialysis only.

Example 10: Body Weight

Procedure.

Figure 11A:
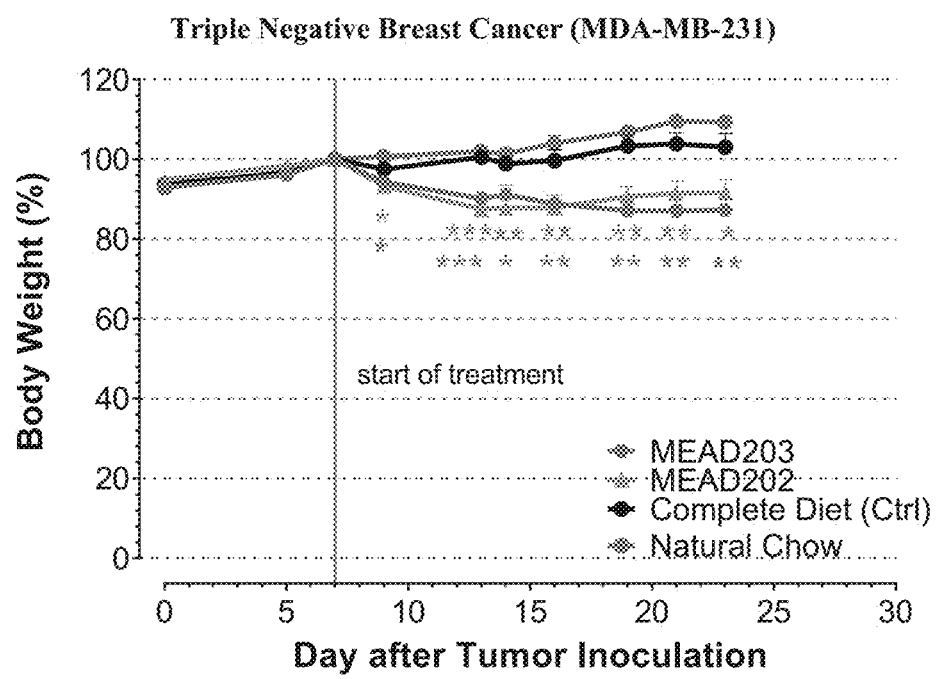
FIG. 11A depicts a graph showing the effects of a complete diet (Ctrl), MEAD203, MEAD202, and natural chow on body weight (%) over time (days after tumor inoculation) in triple negative breast cancer (MDA-MB-231). Mice with implanted MDA-MDB-231 cells were on diet treatment on day 20. The tumor sizes were monitored 3 times weekly. Each group had 5 mice. Significance is shown: * for $P<0.05$,  for $P<0.01$, * for $P<0.001$.
Figure 11B:
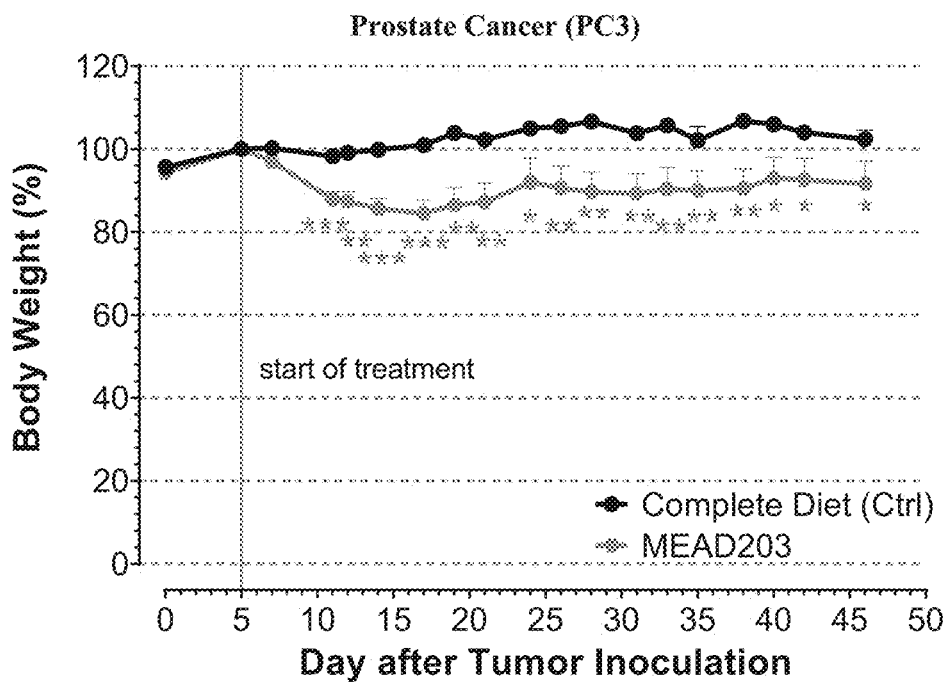
FIG. 11B depicts a graph showing the effects of a complete diet (Ctrl), and MEAD203 on body weight (%) over time (days after tumor inoculation) in prostate cancer (PC3). Mice with implanted PC-3 cells were on diet treatment on day 5. The tumor sizes were monitored 3 times weekly. Each group had 5 mice. Significance is shown: * for P<0.05,  for P<0.01, * for P<0.001

In FIG. 11A athymic nude mice were implanted with MDA-MDB-231 cells by subcutaneous injection. The mice were 5-6 weeks old. The study had 4 groups: mice administered with MEAD203, mice administered with MEAD202, mice administered with complete diet, and mice administered with natural chow. Natural chow is described in Example 16. Each group had 5 mice. The mice were placed on respective diets on day 20. The complete diet and treatment diet compositions are described in Table 5 of Example 14. The mice were fed ad libitum. The body weights were monitored 3 times weekly. Tumor tissues and plasma samples were collected, and only plasma samples were analyzed for glucose and beta-keto body measurement. Significance is shown: * for P<0.05,  for P<0.01, * for P<0.001. In FIG. 11B, athymic nude mice were implanted with PC-3 cells by subcutaneous injection. mice that were implanted with implanted PC-3 cells by subcutaneous injection. The mice were 5-6 weeks old. The study had 2 groups: mice administered with MEAD203, and mice administered with complete diet. Each group had 5 mice. The mice were placed on respective diets on day 5. The mice were fed ad libitum. The complete diet and MEAD 202 compositions are described in Table 5 of Example 14. The body weights were monitored 3 times weekly. Tumor tissues and plasma samples were collected, and only plasma samples were analyzed for glucose and beta-keto body measurement. Significance is shown: * for P<0.05,  for P<0.01, * for P<0.001.

Results. As shown in FIG. 11, the mice that were administered a treatment of MEAD203 and the mice treated with MEAD202 exhibited a reduction in body weight as compared to the mice on a complete diet and the mice on natural chow. By day 23, the mice that were administered MEAD203 and the mice treated with MEAD202 exhibited approximately a 15% reduction in body weight as compared to the mice on a complete diet and the mice on dialysis only. Body weight loss were relatively stabilize for the treatment diets.

Example 11: Blood Sugar

Figure 12A:
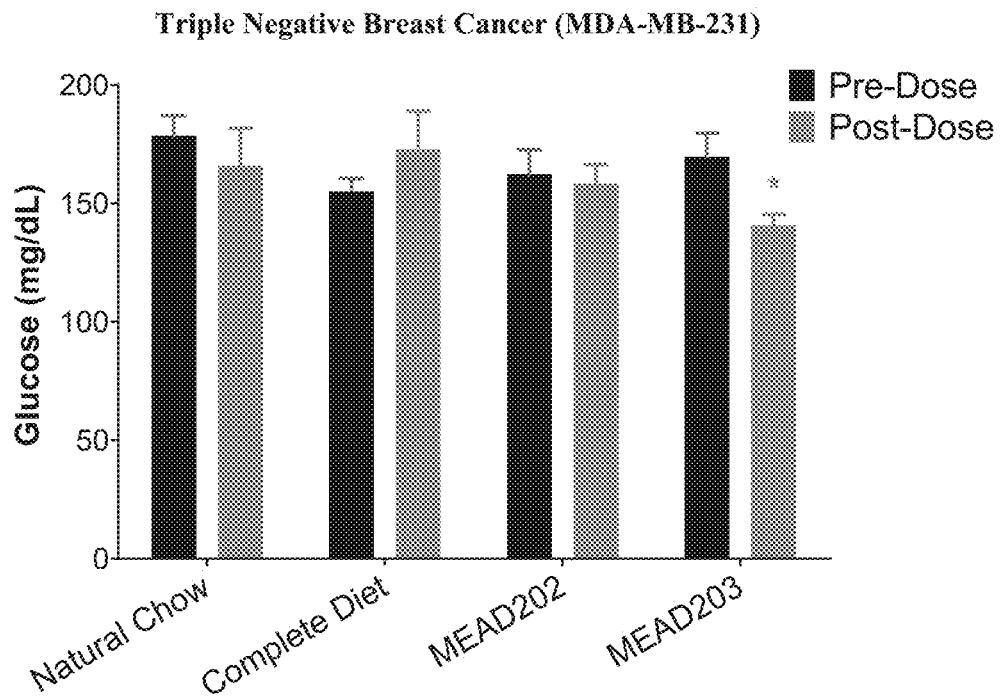
FIG. 12A depicts a graph showing the effects of natural chow, complete diet, MEAD202, MEAD203 on glucose (mg/dL) in triple negative breast cancer (MDA-MB-231). Glucose in plasma was measured with Nova Max Glucose Test Strips. Mice with implanted MDA-MDB-231 cells were on diet treatment on day 20. The plasma samples were collected before treatment started and after treatment completed. Each group had 5 mice. Significance is shown: * for P<0.05,  for P<0.01, * for P<0.001.
Figure 12B:
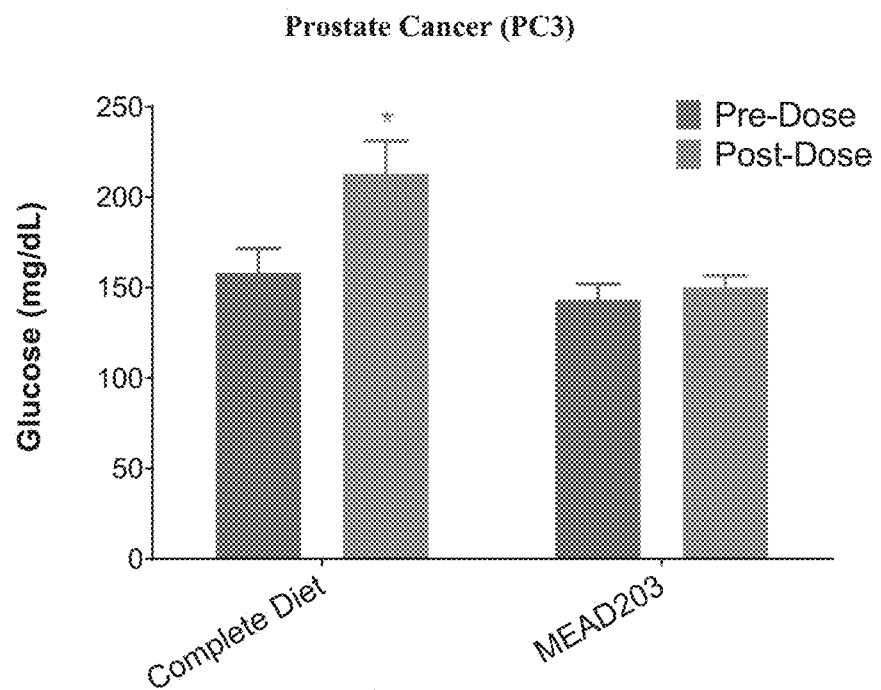
FIG. 12B depicts a graph showing the effects of complete diet and MEAD203 on glucose (mg/dL) in prostate cancer (PC3). Glucose in plasma was measured with Nova Max Glucose Test Strips. Mice with implanted PC-3 cells were on diet treatment on day 5. The plasma samples were collected before treatment started and after treatment completed. Each group had 5 mice. Significance is shown: * for P<0.05,  for P<0.01, * for P<0.001.

Procedure. In FIG. 12A athymic nude mice were implanted with MDA-MDB-231 cells by subcutaneous injection. The mice were 5-6 weeks old. The study had 4 groups: mice administered with MEAD203, mice administered with MEAD202, mice administered with complete diet, and mice administered with natural chow. Natural chow is described in Example 16. Each group had 5 mice. The mice were placed on the respective diet on day 20. The complete diet and treatment diet compositions are described in Table 5 of Example 14. The mice were fed ad libitum. The plasma samples were collected before treatment started and after treatment completed. Significance is shown: * for P<0.05,  for P<0.01, * for P<0.001. In FIG. 12B, athymic nude mice were implanted with PC-3 cells by subcutaneous injection. The mice were 5-6 weeks old. The study had 2 groups: mice administered with MEAD203, and mice administered with complete diet. Each group had 5 mice. The mice were placed on the respective diet on day 5. The mice were fed ad libitum. The complete diet and MEAD 203 compositions are described in Table 5 of Example 14. The plasma samples were collected before treatment started and after treatment completed. Tumor tissues and plasma samples were collected, and only plasma samples were analyzed for glucose and beta-keto body measurement. Significance is shown: * for P<0.05,  for P<0.01, * for P<0.001. Glucose in plasma was measured with Nova Max Glucose Test Strips.

Results.

As shown in FIG. 12A and FIG. 12B, blood sugar is not increased in the treatment groups. In FIG. 12A, the post-dose glucose levels of the MEAD202 mice and MED203 mice were similar or lower than the pre-dose levels. In FIG. 12B, the post-dose glucose levels of the MEAD203 mice were similar to its pre-dose levels.

Example 12: Ketosis

Procedure.

Figure 13A:
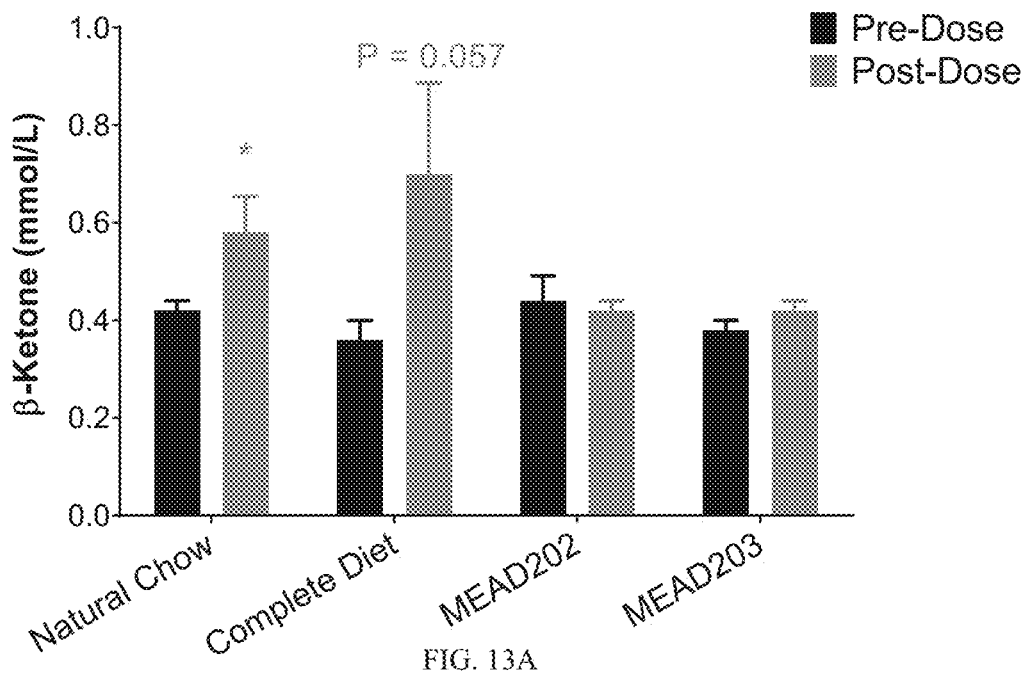
FIG. 13A depicts a graph showing the effects of natural chow, complete diet, MEAD202, MEAD203 on β-Ketone (mmol/L) in triple negative breast cancer (MDA-MB-231). Beta-ketone body in plasma was measured with Nova Max Ketone Test Strips. Mice with implanted MDA-MDB-231 cells were on diet treatment on day 20. The plasma samples were collected before treatment started and after treatment completed. Each group had 5 mice. Significance is shown: * for P<0.05,  for P<0.01, * for P<0.001.
Figure 13B:
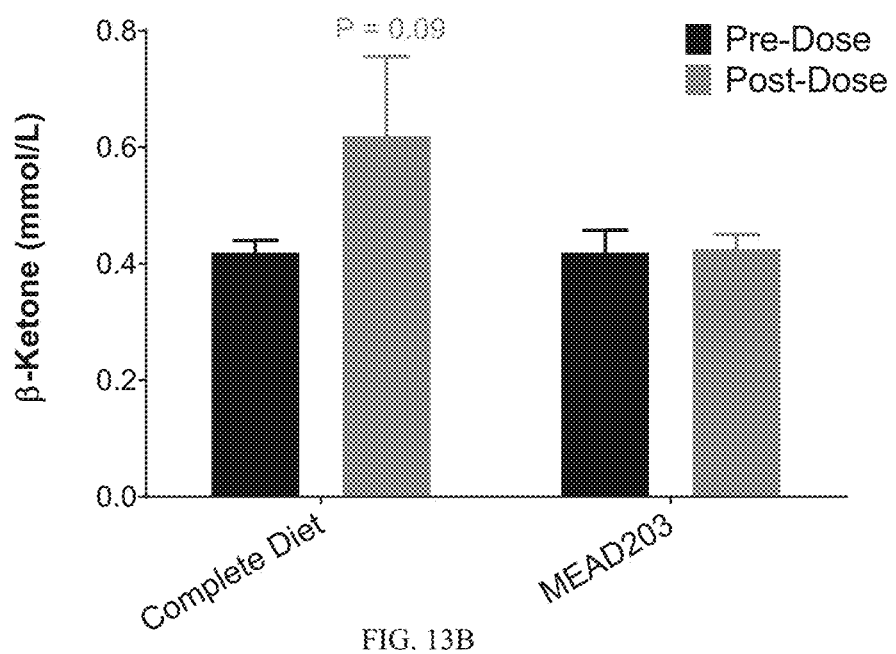
FIG. 13B depicts a graph showing the effects of complete diet and MEAD203 on β-Ketone (mmol/L) in prostate cancer. Beta-ketone body in plasma was measured with Nova Max Ketone Test Strips. Mice with implanted PC-3 cells were on diet treatment on day 5. The plasma samples were collected before treatment started and after treatment completed. Each group had 5 mice. Significance is shown: * for P<0.05,  for P<0.01, * for P<0.001.

In FIG. 13A, athymic nude mice were implanted with MDA-MDB-231 cells by subcutaneous injection. The mice were 5-6 weeks old. The study had 4 groups: mice administered with MEAD203, mice administered with MEAD202, mice administered with complete diet, and mice administered with natural chow. Natural chow is described in Example 16. Each group had 5 mice. The mice were placed on the respective diet on day 20. The complete diet and treatment diet compositions are described in Table 5 of Example 14. The mice were fed ad libitum. The plasma samples were collected before treatment started and after treatment completed. Tumor tissues and plasma samples were collected, and only plasma samples were analyzed for glucose and beta-keto body measurement. Significance is shown: * for P<0.05,  for P<0.01, * for P<0.001. In FIG. 13B, athymic nude mice were implanted with PC-3 cells by subcutaneous injection. The mice were 5-6 weeks old. The study had 2 groups: mice administered with MEAD203, and mice administered with complete diet. Each group had 5 mice. The mice were placed on the respective diet on day 5. The mice were placed on the respective diets 5 days after implantation. The mice were fed ad libitum. The complete diet and MEAD 203 compositions are described in Table 5 of Example 14. The plasma samples were collected before treatment started and after treatment completed. Tumor tissues and plasma samples were collected, and only plasma samples were analyzed for glucose and beta-keto body measurement. Significance is shown: * for P<0.05,  for P<0.01, * for P<0.001. Beta-ketone body in plasma was measured with Nova Max Ketone Test Strips.

Results.

As shown in FIG. 13A and FIG. 13B, ketosis is not triggered by the administration of the treatment diets. In FIG. 13A, the post-dose β-ketone levels of the MEAD202 mice and MED203 mice were similar to the pre-dose levels. In FIG. 13B, the post-dose β-ketone levels of the MEAD203 mice were similar to its pre-dose levels.

Example 13: Dialysis Fluid Composition

Table 4 as presented below provides an exemplary formulation of the dialysis fluid—dry composition, concentrated composition, or liquid composition—described herein.

TABLE 4

| Dialysis fluid composition | |
|---|---|
| Dextrose | 236 mM |
| Sodium chloride | 132 mM |
| Sodium lactate | 40 mM |
| Calcium chloride | 1.75 mM |
| Magnesium chloride | 0.25 mM |

| | μmole |
|---|---|
| Essential + Arg/Glu Amino acid (/L) | |
| Arginine | 60.25 |
| Glutamate | 140 |
| Histidine | 83.5 |
| Isoleucine | 79.75 |
| Leucine | 119 |
| Lysine | 195 |
| Methionine | 22.25 |
| Phenylalanine | 55.25 |
| Threonine | 137.25 |
| Tryptophan | 204.23 |
| Valine | 242.5 |
| Vitamin (/L) | |
| Vitamin A | 0.052 |
| Vitamin C | 7.57 |
| Vitamin B6 | 1.48 |
| Vitamin E | 0.90 |
| Folate (Vit B9) | 15.18 |
| Vitamin D | 0.0044 |
| Vitamin K | 0.0038 |
| Thiamine | 0.075 |
| Riboflavin | 0.053 |
| Niacinamide | 4.71 |
| Vitamin B12 | 0.000030 |
| Pantothenic-Ca | 0.38 |
| Biotin | 0.0020 |
| Choline | 79.99 |
| Mineral (/L) | |
| Iron | 2.33 |
| Copper | 0.24 |
| Chromium | 0.010 |
| Fluoride | 3.16 |
| Iodine | 0.020 |
| Manganese | 0.55 |
| Molybdenum | 0.0078 |
| Selenium | 0.012 |
| Zinc | 2.60 |

Example 14: Food Composition

Table 5 as presented below provides an exemplary formulation of a food composition described herein. The food compositions below were the diets used in studies above.

TABLE 5

| Dietary Components | MEAD201 (gm/kg) Amount and Calories | | MEAD203 (gm/kg) Amount and Calories | | MEAD204 (gm/kg) Amount and Calories | | MEAD205 (gm/kg) Amount and Calories | | Complete Diet (gm/kg) Amount and Calories | |
|---|---|---|---|---|---|---|---|---|---|---|
| | gm % | kcal % | gm % | kcal % | gm % | kcal % | gm % | kcal % | gm % | kcal % |
| Protein | 17.0 | 17.7 | 17.0 | 17.7 | 17.0 | 17.7 | 17.0 | 17.7 | 17.0 | 17.7 |
| Carbohydrate | 70.3 | 73.0 | 70.3 | 73.0 | 70.3 | 73.0 | 70.3 | 73.0 | 70.3 | 73.0 |
| Fat | 5 | 11.7 | 5 | 11.7 | 5 | 11.7 | 5 | 11.7 | 5 | 11.7 |
| overall kcal/gm | | 3.9 | | 3.9 | | 3.9 | | 3.9 | | 3.9 |
| Ingredient (gm) | gm | kcal | gm | kcal | gm | kcal | gm | kcal | gm | kcal |
| Gelatin Essential amino acids | 0 | 0 | 0 | 0 | 0 | 0 | 0 | 0 | 0 | 0 |
| L-Arginine | 10.7 | 43 | 15.4 | 62 | 12.3 | 49 | 0.0 | 0 | 10.0 | 40 |
| L-Histidine-HCl—H2O | 6.4 | 26 | 9.2 | 37 | 7.4 | 30 | 8.2 | 33 | 6.0 | 24 |
| L-Isoleucine | 8.6 | 34 | 12.3 | 49 | 9.9 | 39 | 11.0 | 44 | 8.0 | 32 |
| L-Leucine | 12.9 | 51.4 | 18.5 | 74.0 | 14.8 | 59.1 | 16.4 | 65.7 | 12.0 | 48 |
| L-Lysine-HCl | 15.0 | 60.0 | 21.6 | 86.3 | 17.2 | 69.0 | 19.2 | 76.7 | 14.0 | 56 |
| L-Methionine | 10.0 | 40.0 | 10.0 | 40.0 | 10.0 | 40.0 | 10.0 | 40.0 | 6.0 | 24 |
| L-Phenylalanine | 12.5 | 49.9 | 18.0 | 71.8 | 14.3 | 57.4 | 16.0 | 63.8 | 8.0 | 32 |
| L-Threonine | 8.6 | 34.3 | 12.3 | 49.3 | 9.9 | 39.4 | 11.0 | 43.8 | 8.0 | 32 |
| L-Tryptophan | 2.1 | 8.6 | 3.1 | 12.3 | 2.5 | 9.9 | 2.7 | 11.0 | 2.0 | 8 |
| L-Valine | 8.6 | 34.3 | 12.3 | 49.3 | 9.9 | 39.4 | 11.0 | 43.8 | 8.0 | 32 |

TABLE 5-continued

Food composition

| Nonessential amino acids | | | | | | | | | | |
|---|---|---|---|---|---|---|---|---|---|---|
| L-Alanine | 10.7 | 42.8 | 0.0 | 0.0 | 12.3 | 49.3 | 13.7 | 54.8 | 10.0 | 40 |
| L-Asparagine-H2O | 5.4 | 21.4 | 0.0 | 0.0 | 0.0 | 0.0 | 0.0 | 0.0 | 5.0 | 20 |
| L-Aspartate | 10.7 | 42.8 | 0.0 | 0.0 | 0.0 | 0.0 | 0.0 | 0.0 | 10.0 | 40 |
| L-Cystine | 0.0 | 0.0 | 0.0 | 0.0 | 0.0 | 0.0 | 0.0 | 0.0 | 4.0 | 16 |
| L-Glutamic Acid | 37.2 | 148.9 | 37.2 | 148.9 | 37.2 | 148.9 | 37.2 | 148.9 | 30.0 | 120 |
| L-Glutamine | 0.0 | 0.0 | 0.0 | 0.0 | 0.0 | 0.0 | 0.0 | 0.0 | 5.0 | 20 |
| Glycine | 10.7 | 42.8 | 0.0 | 0.0 | 12.3 | 49.3 | 13.7 | 54.8 | 10.0 | 40 |
| L-Proline | 0.0 | 0.0 | 0.0 | 0.0 | 0.0 | 0.0 | 0.0 | 0.0 | 5.0 | 20 |
| L-Serine | 0.0 | 0.0 | 0.0 | 0.0 | 0.0 | 0.0 | 0.0 | 0.0 | 5.0 | 20 |
| L-Tyrosine | 0.0 | 0.0 | 0.0 | 0.0 | 0.0 | 0.0 | 0.0 | 0.0 | 4.0 | 16 |
| Total L-Amino Acids | 170.0 | 680.0 | 170.0 | 680.0 | 170.0 | 680.0 | 170.0 | 680.0 | 170.0 | 680.0 |
| Corn Starch | 468 | 1872 | 468 | 1872 | 468 | 1872 | 468 | 1872 | 468 | 1872 |
| Maltodextrin 10 | 125 | 500 | 125 | 500 | 125 | 500 | 125 | 500 | 125.0 | 500 |
| Sucrose | 100 | 400 | 100 | 400 | 100 | 400 | 100 | 400 | 100.0 | 400 |
| Cellulose | 50 | 0 | 50 | 0 | 50 | 0 | 50 | 0 | 50.0 | 0 |
| Soybean oil | 40 | 360 | 40 | 360 | 40 | 360 | 40 | 360 | 40.0 | 360 |
| t-Butylhydroquinone | 0.008 | 0 | 0.008 | 0 | 0.008 | 0 | 0.008 | 0 | 0.008 | 0 |
| Mineral Mix S10022M | 35 | 0 | 35 | 0 | 35 | 0 | 35 | 0 | 35 | 0 |
| Vitamin Mix V10037 | 10 | 40 | 10 | 40 | 10 | 40 | 10 | 40 | 10 | 40 |
| Choline Bitartrate | 2.5 | 0 | 2.5 | 0 | 2.5 | 0 | 2.5 | 0 | 2.5 | 0 |
| Total | 1000.5 | 3852.0 | 1000.5 | 3852.0 | 1000.5 | 3852.0 | 1000.5 | 3852.0 | 1000.5 | 3852.0 |

Example 15: Reduction of Cysteine Uptake with Glutamate and Vitamins

The studies of the present disclosure showed that plasma glutamate was increased by about 80-100% in mice when on MEAD treatment diets. The increase in plasma glutamate may result in a reduction of cysteine update due to the effects on the xCT transporter. This could theoretically halve all cells' capability of cysteine uptake.

The studies of the present disclosure show that vitamins have an important function in the reduction of cysteine. Vitamins (especially vitamin B family) are important for dialysis and the nutritional diet disclosed herein. The vitamins may maintain appropriate physiology in normal cells. Vitamins are important for neural health and metabolism. Vitamins may also help normal cells synthesize the target nutrients when these nutrients are not provided through diet or depleted through dialysis. Vitamin C was not included for mouse studies because vitamin C (ascorbic acid) is not vitamin for mice because they can make it internatively. Vitamin C is expected to be important in treating humans. Table 6 below provides a few exemplary vitamins for use in the compositions described herein.

TABLE 6

| Vitamins | |
|---|---|
| Vitamin (/L) | μmol |
| Vitamin A | 0.052 |
| Vitamin C | 7.57 |
| Vitamin B6 | 1.48 |
| Vitamin E | 0.90 |
| Folate (Vit B9) | 15.18 |
| Vitamin D | 0.0044 |
| Vitamin K | 0.0038 |
| Thiamine | 0.075 |
| Riboflavin | 0.053 |
| Niacinamide | 4.71 |
| Vitamin B12 | 0.000030 |

TABLE 6-continued

| Vitamins | |
|---|---|
| Vitamin (/L) | μmol |
| Pantothenic-Ca | 0.38 |
| Biotin | 0.0020 |
| Choline | 79.99 |

Example 16: Natural Chow Composition

TABLE 7

| Natural chow composition | |
|---|---|
| Nutrients[2] | |
| Protein, % | 21.0 |
| Arginine, % | 1.29 |
| Cystine, % | 0.36 |
| Glycine, % | 0.97 |
| Histidine, % | 0.53 |
| Isoleucine, % | 0.86 |
| Leucine, % | 1.57 |
| Lysine, % | 1.18 |
| Methionine, % | 0.62 |
| Phenylalanine, % | 0.91 |
| Tyrosine, % | 0.60 |
| Threonine, % | 0.78 |
| Tryptophan, % | 0.24 |
| Valine, % | 0.97 |
| Serine, % | 0.98 |
| Aspartic Acid, % | 2.19 |
| Glutamic Acid, % | 4.18 |
| Alanine, % | 1.19 |
| Proline, % | 1.31 |
| Taurine, % | 0.03 |
| Fat (ether extract), % | 5.0 |
| Fat (acid hydrolysis), % | 6.3 |
| Cholesterol, ppm | 142 |
| Linoleic Acid, % | 2.12 |
| Linolenic Acid, % | 0.27 |

TABLE 7-continued

Natural chow composition

| | |
|---|---|
| Arachidonic Acid, % | 0.01 |
| Omega-3 Fatty Acids, % | 0.45 |
| Total Saturated Fatty Acids, % | 0.78 |
| Total Monounsaturated Fatty Acids, % | 0.96 |
| Fiber (Crude), % | 4.6 |
| Neutral Detergent Fiber[3], % | 16.0 |
| Acid Detergent Fiber[4], % | 5.8 |
| Nitrogen-Free Extract (by difference), % | 53.4 |
| Starch, % | 28.2 |
| Glucose, % | 0.19 |
| Fructose, % | 0.24 |
| Sucrose, % | 3.25 |
| Lactose, % | 1.34 |
| Total Digestible Nutrients, % | 75.1 |
| Gross Energy, kcal/gm | 4.11 |
| Physiological Fuel Value[5], kcal/gm | 3.43 |
| Metabolizable Energy, kcal/gm | 3.03 |
| Minerals Ash, % | 5.9 |
| Calcium, % | 0.81 |
| Phosphorus, % | 0.64 |
| Phosphorus (non-phytate), % | 0.34 |
| Potassium, % | 1.10 |
| Magnesium, % | 0.22 |
| Sulfur, % | 0.33 |
| Sodium, % | 0.30 |
| Chloride, % | 0.52 |
| Fluorine, ppm | 9.3 |
| Iron, ppm | 185 |
| Zinc, ppm | 89 |
| Manganese, ppm | 84 |
| Copper, ppm | 14 |
| Cobalt, ppm | 0.71 |
| Iodine, ppm | 0.97 |
| Chromium (added), ppm | 0.01 |
| Selenium, ppm | 0.37 |
| Vitamins | |
| Carotene, ppm | 1.5 |
| Vitamin K, ppm | 3.3 |
| Thiamin, ppm | 17 |
| Riboflavin, ppm | 8.0 |
| Niacin, ppm | 85 |
| Pantothenic Acid, ppm | 17 |
| Choline Chloride, ppm | 2000 |
| Folic Acid, ppm | 3.0 |
| Pyridoxine, ppm | 9.6 |
| Biotin, ppm | 0.30 |
| $B_{12}$, mcg/kg | 51 |
| Vitamin A, IU/gm | 15 |
| Vitamin $D_3$ (added), IU/gm | 2.3 |
| Vitamin E, IU/kg | 99 |
| Ascorbic Acid, mg/gm | 0.00 |
| Calories provided by: | |
| Protein, % | 24.517 |
| Fat (ether extract), % | 13.134 |
| Carbohydrates, % | 62.349 |
| Vitamins | |
| Carotene, ppm | 1.5 |
| Vitamin K, ppm | 3.3 |
| Thiamin, ppm | 17 |
| Riboflavin, ppm | 8.0 |
| Niacin, ppm | 85 |
| Pantothenic Acid, ppm | 17 |
| Choline Chloride, ppm | 2000 |
| Folic Acid, ppm | 3.0 |
| Pyridoxine, ppm | 9.6 |
| Biotin, ppm | 0.30 |
| $B_{12}$, mcg/kg | 51 |
| Vitamin A, IU/gm | 15 |
| Vitamin $D_3$ (added), IU/gm | 2.3 |
| Vitamin E, IU/kg | 99 |
| Ascorbic Acid, mg/gm | 0.00 |
| Calories provided by: | |
| Protein, % | 24.517 |
| Fat (ether extract), % | 13.134 |
| Carbohydrates, % | 62.349 |

*Product Code
1. Formulation based on calculated values from the latest ingredient analysis information. Since nutrient composition of natural ingredients varies and some nutrient loss will occur due to manufacturing processes, analysis will differ accordingly.
[2]Nutrients expressed as percent of ration except where otherwise indicated. Moisture content is assumed to be 10.0% for the purpose of calculations.
[3]NDF = approximately cellulose, hemi-cellulose and lignin.
[4]ADF = approximately cellulose and lignin.
[5]Physiological Fuel Value (kcal/gm) = Sum of decimal fractions of protein, fat and carbo-hydrate (use Nitrogen Free Extract) × 4, 9, 4 kcal/gm respectively.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A liquid composition comprising:
   (a) dextrose at an amount of at least 1.0% w/v;
   (b) at least one vitamin selected from a group consisting of vitamin A, vitamin B, vitamin C, vitamin D, vitamin E, vitamin K, and choline;
   (c) at least one ion selected from a group consisting of sodium, calcium, magnesium, chloride, and lactate;
   (d) at least one essential amino acid selected from a group consisting of histidine, isoleucine, leucine, lysine, methionine, phenylalanine, threonine, tryptophan, valine, and arginine; and
   (e) an aqueous solution,
   wherein the liquid composition is characterized in that
   (i) it is substantially free of cysteine and/or cystine,
   (ii) it has a molar ratio of cysteine to essential amino acid(s) less than 0.1;
   (iii) it has a pH of 4.0-6.5, and
   (iv) it has an osmolarity of 300-720 milliosmolar (mOsmol/L), and
   wherein the liquid composition is substantially free of nonessential amino acids selected from alanine, asparagine, aspartate, cysteine, glycine, proline, glutamine, serine, and tyrosine.

2. The liquid composition of claim 1, wherein the liquid composition comprises methionine or arginine.

3. The liquid composition of claim 1, wherein each of said at least one vitamin is present at an amount of at least 0.000010 µM.

4. The liquid composition of claim 1, wherein the at least one vitamin comprises vitamin C or vitamin B.

5. The liquid composition of claim 1, wherein the liquid composition comprises vitamin B at an amount of at least 0.00005 µM.

6. The liquid composition of claim 1, wherein the liquid composition comprises glutamate.

7. The liquid composition of claim 6, wherein said glutamate is present at an amount of at least 1 µM.

8. The liquid composition of claim 6, wherein the liquid composition is free of nonessential amino acids other than glutamate.

9. The liquid composition of claim 1, wherein each of said at least one ion is present at an amount of at least 0.1 milliequivalents per liter (mEq/L).

10. The liquid composition of claim 1, further comprising at least one nonessential amino acid.

11. The liquid composition of claim 1, wherein the liquid composition is a dialysis solution.

12. The liquid composition of claim 1, comprising essential amino acids including histidine, isoleucine, leucine, lysine, methionine, phenylalanine, threonine, tryptophan, and valine, wherein each of said at least one essential amino acid is present at an amount of at least 10 µM.

13. The liquid composition of claim 1, wherein the composition is configured for reducing or depleting cysteine and/or cystine from a subject to whom the composition is administered.

14. A dry composition comprising:
(a) dextrose at an amount of at least 0.1 grams;
(b) at least one vitamin selected from a group consisting of vitamin A, vitamin B, vitamin C, vitamin D, vitamin E, vitamin K, and choline;
(c) at least one ion selected from a group consisting of sodium, calcium, magnesium, chloride, and lactate; and
(d) at least one essential amino acid selected from a group consisting of histidine, isoleucine, leucine, lysine, methionine, phenylalanine, threonine, tryptophan, valine, and arginine,
wherein the dry composition (i) is substantially free of cysteine and/or cystine and (ii) has a molar ratio of cysteine to essential amino acids less than 0.1, and
wherein the dry composition is substantially free of nonessential amino acids selected from alanine, asparagine, aspartate, cysteine, glycine, proline, glutamine, serine, and tyrosine.

15. The dry composition of claim 14, wherein said dry composition comprises methionine or arginine.

16. The dry composition of claim 14, wherein said at least one vitamin is present at an amount of at least 0.01 µg.

17. The dry composition of claim 14, wherein the at least one vitamin comprises vitamin C or vitamin B.

18. The dry composition of claim 14, wherein the dry composition comprises glutamate.

19. The dry composition of claim 18, wherein said glutamate is present at an amount of at least 0.1 mg.

20. The dry composition of claim 14, further comprising at least one nonessential amino acid.

21. The dry composition of claim 18, wherein the dry composition is free of nonessential amino acids other than glutamate.

22. The dry composition of claim 14, wherein the dry composition is a dialysis mixture.

23. A concentrated composition comprising a dry composition of claim 14, and an initial aqueous solution, wherein the dry composition is dissolved in the initial aqueous solution.

24. The dry composition of claim 14, comprising essential amino acids including histidine, isoleucine, leucine, lysine, methionine, phenylalanine, threonine, tryptophan, and valine, wherein each of said at least one essential amino acid is present at an amount of at least 2 µg.

25. The dry composition of claim 14, wherein the composition is configured for reducing or depleting cysteine and/or cystine from a subject to whom the composition is administered.

26. The dry composition of claim 14, wherein the composition is stored in a container.

* * * * *